United States Patent [19]
Cai et al.

[11] Patent Number: 6,147,075
[45] Date of Patent: Nov. 14, 2000

[54] ALKYL, AZIDO, ALKOXY AND FLUORO-SUBSTITUTED AND FUSED QUINOXALINEDIONES AND THE USE THEREOF AS GLYCINE RECEPTOR ANTAGONIST

[75] Inventors: Sui Xiong Cai, Irvine; Eckard Weber, Laguna Beach, both of Calif.; John F. W. Keana; Sunil Kher, both of Eugene, Oreg.

[73] Assignees: CoCensys, Inc., Irvine, Calif.; State of Oregon, Acting by and Through the Oregon State Board of Higher Education, Acting for and on Behalf of the Oregon Health Sciences University and the University of Oregon, Eugene Oregon, Eugene, Oreg.; The Regents of the University of California, Oakland, Calif.

[21] Appl. No.: 09/376,536

[22] Filed: Aug. 18, 1999

Related U.S. Application Data

[62] Division of application No. 08/792,872, Jan. 31, 1997, Pat. No. 5,977,107, which is a division of application No. 08/289,603, Aug. 11, 1994, Pat. No. 5,631,373, which is a continuation-in-part of application No. 08/208,878, Mar. 11, 1994, abandoned, which is a continuation-in-part of application No. 08/148,268, Nov. 5, 1993, abandoned, and a continuation-in-part of application No. 08/148,259, Nov. 5, 1993, Pat. No. 5,514,680.

[51] Int. Cl.[7] .......................... A61K 31/495; A61K 31/44
[52] U.S. Cl. .......................... 514/249; 514/250; 514/255; 514/289
[58] Field of Search .................................... 514/249, 255, 514/250, 289

[56] References Cited

U.S. PATENT DOCUMENTS

| | | | |
|---|---|---|---|
| 3,962,440 | 6/1976 | St. Clair et al. | 424/250 |
| 3,992,378 | 11/1976 | St. Clair et al. | 260/250 Q |
| 4,659,713 | 4/1987 | Hass | 514/249 |

(List continued on next page.)

FOREIGN PATENT DOCUMENTS

| | | |
|---|---|---|
| 0 374 534 A1 | 6/1990 | European Pat. Off. . |
| 0 377 112 A1 | 7/1990 | European Pat. Off. . |
| 0 511 152 A2 | 10/1992 | European Pat. Off. . |

(List continued on next page.)

OTHER PUBLICATIONS

Andreasen, M., et al., "Effects of New Non–N–Methyl–D–Aspartate Antagonists on Synaptic Transmission in the in vitro Rat Hippocampus," *J. Physiol.* 414:317–336 (1989).

Allison, C.G., et al., "Polyfluoroheterocyclic Compounds Part XX. Preparation and Nucleophilic Substitution of Hexafluoroquinoxaline," *J. Fluorine Chem.* 1(1):59–67 (1971).

Bigge, C.F., "Structural Requirements for the Development of Potent N–Methyl–D–Aspartic Acid (NMDA) Receptor Antagonists," *Biochem. Pharm.* 45(8):1547–1561 (Apr. 1993).

(List continued on next page.)

*Primary Examiner*—Deborah C. Lambkin
*Attorney, Agent, or Firm*—Sterne, Kessler, Goldstein & Fox, P.L.L.C.

[57] ABSTRACT

Methods of treating or preventing neuronal loss associated with stroke, ischemia, CNS trauma, hypoglycemia, and surgery, as well as treating neurodegenerative diseases including Alzheimer's disease, amyotrophic lateral sclerosis, Huntington's disease, and Down's syndrome, treating or preventing the adverse consequences of the hyperactivity of the excitatory amino acids, as well as treating anxiety, chronic pain, convulsions, and inducing anesthesia are disclosed by administering to an animal in need of such treatment an alkyl or azido-substituted 1,4-dihydroquinoxaline-2,3-dione or pharmaceutically acceptable salts thereof, which have high binding to the glycine receptor.

14 Claims, 9 Drawing Sheets

U.S. PATENT DOCUMENTS

| | | | |
|---|---|---|---|
| 4,803,270 | 2/1989 | Takemoto | 544/105 |
| 4,812,458 | 3/1989 | Honore et al. | 514/249 |
| 4,889,855 | 12/1989 | Jacobsen et al. | 514/250 |
| 4,948,794 | 8/1990 | Honore et al. | 514/249 |
| 4,975,430 | 12/1990 | Jahr et al. | 514/255 |
| 4,977,155 | 12/1990 | Jacobsen et al. | 514/250 |
| 5,026,704 | 6/1991 | Honore et al. | 514/250 |
| 5,055,465 | 10/1991 | Davey | 514/228.2 |
| 5,057,516 | 10/1991 | Jacobsen et al. | 514/250 |
| 5,061,706 | 10/1991 | Honoreé et al. | 514/249 |
| 5,081,123 | 1/1992 | Honoréet al. | 514/250 |
| 5,166,155 | 11/1992 | Jorgensen et al. | 514/249 |
| 5,196,421 | 3/1993 | McQuaid et al. | 514/250 |
| 5,268,378 | 12/1993 | Baker et al. | 514/312 |
| 5,283,244 | 2/1994 | Sakamoto et al. | 514/250 |
| 5,308,845 | 5/1994 | Honoréet al. | 514/250 |
| 5,352,683 | 10/1994 | Mayer et al. | 514/289 |
| 5,514,680 | 5/1996 | Weber et al. | 514/249 |
| 5,620,979 | 4/1997 | Weber et al. | 514/249 |
| 5,622,952 | 4/1997 | Weber et al. | 514/255 |
| 5,631,373 | 5/1997 | Cai et al. | 544/354 |

FOREIGN PATENT DOCUMENTS

| | | |
|---|---|---|
| 24 46 543 A1 | 4/1976 | Germany . |
| 24 51 049 A1 | 4/1976 | Germany . |
| 28 47 285 A1 | 5/1980 | Germany . |
| 72 674 | 11/1974 | Poland . |
| WO 91/13878 | 9/1991 | WIPO . |
| WO 92/11012 | 7/1992 | WIPO . |
| WO 92/11245 | 7/1992 | WIPO . |
| WO 93/08188 | 4/1993 | WIPO . |
| WO 94/00124 | 1/1994 | WIPO . |

OTHER PUBLICATIONS

Birch, P.J., et al., "FG9065 and FG9041 antagonise responses to NMDA via an Action at the strychnine–insensitive glycine receptor," *Br. J. Pharmacol.* 95:758P (1988).

Carling, R.W., et al., "Anticonvulsant Activity of Glycine––Site NMDA Antagonists. 2. Trans 2–Carboxy–4–Substituted Tetrahydroquinolines," *Bioorganic & Medicinal Chem. Lett.* 3(1):65–70 (Jan. 1993).

Carling, R.W., et al., "3–Nitro–3, 4–dihydro–2(1H)–quinolines. Excitatory Amino Acid Antagonists Acting at Glycine–Site NMDA and (RS)–α–Amino–3–hydroxy–5–methyl–4–isoxazolepropionic Acid Receptors," *J. Med. Chem.* 36(22):3397–3408 (Oct. 1993).

Cheeseman, G.W.H., "Quinoxalines and Related Compounds. Part VI. Substitution of 2,3–Dihydroxyquinoxaline and its 1,4–Dimethyl Derivative," *J. Chem. Soc.* 223:1170–1176 (1962).

Danysz, W., and Wrobleski, J.T., "Amnesic Properties of Glutamate Receptor Antagonists," *Neurosci. Res. Comm.* 5(1):9–18 (1989).

Davies, S.N., and Collinridge, G.L., "Quinoxalinediones as Excitatory Amino Acid Antagonists in the Vertebrate Central Nervous System," *Int. Rev. Neurobiol.* 32:281–303 (1990).

Drejer, J., and Honoré, T., "New quinoxalinediones show potent antagonism of quisqualate responses in cultured mouse cortical neurons," *Neuroscience Lett.* 87:104–108 (1988).

Epperson, J.R., et al., "Synthesis and Excitatory Amino Acid Pharmacology of Some Novel Quinoxalinediones," *Bioorganic & Medicinal Chem. Lett.* 3(12):2801–2804 (Dec. 1993).

Fletcher, E.J., and Lodge, D., "Glycine reverses antagonism of N–methyl–D–aspartate (NMDA) by 1–hydroxy–3–aminopyrrolidone–2 (HA–966) but not by D–2–amino–5–phophonovalerate (D–AP5) on rat cortical slices," *Eur. J. Pharmacol.* 151:161–162 (1988).

Fletcher, E.J., et al., "Quinoxalinediones selectively block quisqualate and kainate receptors and synaptic events in rat neocortex and hippocampus and frog spinal cord in vitro," *Br. J. Pharmacol.* 95:585–597 (1988).

Frandsen, A., et al., "Direct Evidence That Excitotoxicity in Cultured Neurons Is Mediated via N–Methyl–D–Aspartate (NMDA) as well as Non–NMDA Receptors," *J. Neurochem.* 53(1):297–299 (1989).

Frenk, H., et al., "Absence of Side–Effects in the Anticonvulsant Action of Cortically Applied Antagonists of N–Methyl–D–Aspartate," *Brain Res.* 373:222–226 (1986).

Hays, S.J., et al., "N–Sulfonyl Derivatives of 6,7–Dichloro–3,4–dihydro–3–oxo–quinoxalinecarboxylate as Glycine–Site NMDA and AMPA Antagonists," *Bioorganic & Medicinal Chem. Lett.* 3(1):77–80 (Jan. 1993).

Honoré, T., et al., "Quinoxalinediones: Potent Competitive Non–NMDA Glutamate Receptor Antagonists," *Science* 241:701–703 (1988).

Honoré,T., et al., "Preparation and resting of 2,3(1H, 4H)–quinoxalinediones as neuroleptics," *Chem. Abstr.* 111:232859a (1989).

Honoré, T., et al., "Quinoxalinediones. Non–N–Methyl––D–aspartate Receptor Antagonists as Potential Drug Candidates," in *Excitatory Amino Acids*, Meldrum et al., eds. New York: Raven Press, Ltd., pp. 451–460 (1991).

Honoré, T., et al., "Preparation and use of neuroleptic quinoxaline compounds," *Chem. Abstr.* 114:81885q (1991).

Horner, L., and Schwenk, U., "Derivatives of quinoxaline as isosteres of the pteridines," *Chem. Abstr.* 48:2692–2693 (1954).

Joergensen, A.S., et al., "Preparation of 1–carboxyalkyl–2, 3–dioxoquinoxalines as glycine antagonists," *Chem. Abstr.* 115:280059u (1991).

Jurson, P.A., and Freed, W.J., "A Slight Anticonvulsant Effect of CNQX and DNQX as Measured by Homocysteine– and Quisqualate–Induced Seizures," *Pharmacological Biochemistry and Behavior* 36:177–181 (1990).

Kay, C.D., and Ikeda, H., "The quinoxalinediones antagonise the visual firing of sustained retinal ganglion cells," *Eur. J. Pharmacol.* 164:381–384 (1989).

Kemp, J.A., and Leeson, P.D., "The glycine site of the NMDA receptor—five years on," *TiPS* 14:20–25 (Jan. 1993).

Kessler, M., et al., "Quinoxaline derivatives are high–affinity antagonists of the NMDA receptor–associated glycine sites," *Brain Res.* 489:377–382 (1989).

Kessler, M, et al., "A Glycine Site Associated with N–Methyl–D–Aspartic Acid Receptors: Characterization and identification of a New Class of Antagonists," *J. Neurochem.* 52(4):1319–1328 (1989).

Kleckner, N.W., and Dingledine, R., "Selectivity of Quinoxalines and Kynurenines as Antagonists of the Glycine Site on N–Methyl–D–aspartate Receptors," *Molec. Pharmacol.* 36:430–436 (1989).

Kulagowski, J.J., et al., "3'–(Arylmethyl)– and 3'–(Aryloxy)–3–phenyl–4–hydroxyquinolin–2(1H)–ones: Orally Active Antagonists of the Glycine Site on the NMDA Receptor," *J. Med. Chem.* 37(10):1402–1405 (1994).

Leeson, P.D., et al., "Kynurenic Acid Derivatives. Structure–Activity Relationships for Excitatory Amino Acid Antagonism and Identification of Potent and Selective Antagonists at the Glycine Site on the N–Methyl–D–aspartate Receptor," *J. Med. Chem.* 34(4):1243–1252 (1991).

Leeson, P.D., "Glycine–Site–N–Methyl–D–Aspartate Receptor Antagonists," in *Drug Design for Neruroscience,* A.P. Kozikowski, ed. New York: Raven Press, Ltd., pp. 339–381 (Jul. 1993).

Leeson, P.D., et al., "Amino Acid Bioisosteres: Design of 2–Quinolone Derivatives as Glycine–Site N–Methyl–D–Aspartate Receptor Antagonists," *Bioorganic & Medicinal Chem. Lett.* 3(2):299–304 (Feb. 1993).

Leeson, P.D., and Iversen, L.L., "The Glycine Site on the NMDA Receptor: Structure–Activity Relationships and Therapeutic Potential," *J. Med. Chem.* 37(24):4053–4067 (1994).

Lester, R.A.J., et al., "Interaction of 6–Cyano–7–nitroquinoxaline–2,3–dione with the N–Methyl–D–aspartate Receptor–Associated Glycine Binding Site," *Molec. Pharmacol.* 35:565–570 (1989).

Littman, T., et al., "The quinoxalinediones DNQX, CNQX and two related congeners suppress hair cell–to–auditory nerve transmission," *Hearing Res.* 40:45–54 (1989).

Lodge, D., and Jones, M.G., "Evidence for Glutamate Receptor Subtypes from in vivo Electrophysiology: Studies with HA–966, Quinoxalinediones and Philanthotoxin," in *Excitatory Amino Acids and Neuronal Plasticity,* Ben–Ari, Y., ed. New York: Plenum Press, pp. 101–108 (1990).

Lodge, D., et al., "Excitatory amino acids: new tools for old stories or Pharmacological subtypes of glutamate receptors: electrophysiological studies," *Can. J. Physiol. Pharmacol.* 69:1123–1128 (1991).

Louvet, P., et al., "Novel benzimidazoles as ligands for the strychnine–insensitive N–methyl–D–aspartate–linked glycine receptor," *Eur. J. Med. Chem.* 28:71–75 (Jan. 1993).

Lufty, K., et al., "Inhibition of clonic seizure–like excitatory effects induced by intrathecal morphine using two NMDA receptor antagonists: MK–801 and ACEA–1011," *Eur. J. Pharmacol.* 252:261–266 (1994).

Lufty, K., et al., "Analgesia–Induced by Morphine and ACEA–1011, a Novel Glycine–NMDA Receptor Antagonist in the Formalin Test in Mice Selectively Bred for High and Low Swin–Induced Analgesia," abstract No. 3646, *FASEB Journal* 8(5):A629 (1994).

Lufty, K., et al., "Blockade of morphine tolerance by ACEA–1328, a novel NMDA receptor/glycine site antagonist," *Eur. J. Pharmacol.* 273:187–189 (1995).

Matsumoto, M., et al., "AMPA and NMDA Receptor Antagonists Do Not Decrease Hippocampal Glutamate Concentrations during Transient Global Ischemia," *Anesthesiology* 77(4):764–771 (Oct. 1992).

McFarlane, M.D., and Smith, D.M., "A New Route to N–Hydroxyquinoxaline–2,3–diones and some Aza–Analogues," *Tetrahedron Lett.* 28(50):6363–6366 (1987).

McQuaid, L.A., et al., "Synthesis and Excitatory Amino Acid Pharmacology of a Series of Heterocyclic–Fused Quinoxalinones and Quinazolinones," *J. Med. Chem.* 35(18):3319–3324 (Sep. 1992).

Moore, K.W., et al., "Anticonvulsant Activity of Glycine–Site NMDA Antagonists. 1. 2–Carboxyl Prodrugs of 5,7–Dichlorokynurenic Acid," *Bioorganic & Medicinal Chem. Lett.* 3(1):61–64 (Jan. 1993).

Näsström, J., et al., "Antinociceptive actions of different classes of excitatory amino acid receptor antagonists in mice," *Eur. J. Pharmacol.* 212(1):21–29 (Feb. 1992).

Ogita, K., and Yoneda, Y., "6,7–Dichloroquinoxaline–2,3–Dione is a Competitive Antagonist Specific to Strychnine–Insensitive [$^3$H]Glycine Binding Sites on the N–Methyl–D–Aspartate Receptor Complex," *J. Neurochem.* 54(2):699–702 (1990).

Patel, J., et al., "6,7–Dinitroquinoxaline–2,3–Dione Blocks the Cytotoxicity of N–Methyl–D–Aspartate and Kainate, but Not Quisqualate, in Cortical Cultures," *J. Neurochem.* 55(1):114–121 (1990).

Pelligrini–Giampietro, D.E., et al., "Quinoxalines interact with the glycine recognition site of NMDA receptors: studies in guinea–pig myenteric plexus and in rat cortical membranes," *Br. J. Pharmacol.* 98:1281–1286 (1989).

Randle, J.C.R., et al., "Quinoxaline Derivatives: Structure–Activity Relationships and Physiological Implications on Inhibition of N–Methyl–D–aspartate and Non–N–Methyl–D–aspartate Receptor–Mediated Currents and Synaptic Potentials," *Mol. Pharmacol.* 41:337–345 (1991).

Randle, J.C.R., et al., "Competitive inhibition by NBQX of kainate/AMPA receptor currents and excitatory synaptic potentials: importance of 6–nitro substitution," *Eur. J. Pharmacol.* 215(2/3):237–244 (May 1992).

Rao, T.S., et al., "6,7–Dinitroquinoxaline–2,3–dione and 6–Nitro,7–cyanoquinoxaline–2,3–dione Antagonize Responses Mediated by N–Methyl–D–aspartate and NMDA–Associated Glycine Recognition Sites in vivo: Measurements of cerebellar Cyclic–GMP," *Neuropharmacol.* 29(11):1031–1035 (1990).

Rowley, M., et al., "3–Acyl–4–hydroxyquinolin–2(1H)–ones. Systemically Active Anticonvulsants Acting by Antagonism at the Glycine Site of the N–Methyl–D–aspartate Receptor Complex," *J. Med. Chem.* 36(22):3386–3396 (Oct. 1993).

Sarges, R., et al., "4–Amino[1,2,4]triazolo[4,3–∂]quinoxalines. A Novel Class of Potent Adenosine Receptor Antagonists and Potential Rapid–Onset Antidepressants," *J. Med. Chem.* 33(8):2240–2254 (1990).

Schoepp, D.D., et al., "Excitatory amino acid–induced convulsions in neonatal rats mediated by distinct receptor subtypes," *Eur. J. Pharmacol.* 182(3):421–427 (1990).

Sheardown, M.J., et al., "A potent antagonist of the strychnine insensitive glycine receptor has anticonvulsant properties," *Eur. J. Pharmacol.* 174:194–204 (1989).

Sheardown, M.J., et al., "2,3–Dihydroxy–6–nitro–7–sulfamoyl–benzo(F)quinoxaline: A Neuroprotectant for Cerebral Ischemia," *Science* 247:571–574 (1990).

Smith, E.C.R., et al., "Structure–Activity Relationships of a Series of Glycine Antagonists Related to 5,7–Dichlorokynurenic Acid and 3–(2–Carboxy–6–chloroindol–3–yl)acetic Acid," *Bioorganic & Medicinal Chem. Lett* 3(1):81–84 (Jan. 1993).

Tricklebank, M.D., et al., "The behavioural effects of MK–801: a comparison with antagonists acting non–competitively and competitively at the NMDA receptor," *Eur. J. Pharmacol.* 167:127–135 (1989).

Turski, L., et al., "Relief of Experimental Spasticity and Anxiolytic/Anticonvulsant Actions of the Alpha–Amino–3–hydroxy–5–methyl–4–isoxazolepropionate Antagonist 2,3–Dihydroxy–6–nitro–7–sulfamoyl–benzo(F)quinoxaline," *J. Pharm. Exp. Ther.* 260(2):742–747 (Feb. 1992).

Vaccarino, A.L., et al., "Non–competitive NMDA Antagonist, MK–801, and Glycine Antagonist, ACEA–1011, Prevent the Development of Tonic Pain Following Subcutaneous Formalin," abstract 291.6, *Soc. Neurosci. Abstr.* *18(1)*:686 (Oct. 1992).

Vaccarino, A.L., et al., "NMDA receptor antagonists, MK–801 and ACEA–1011, prevent the development of tonic pain following subcutaneous formalin," *Brain Res.* *615(2)*:331–334 (Jul. 1993).

Warner, D.S., et al., "In Vivo Models of Cerebral Ischemia: Effects of Parenterally Administered NMDA Receptor Glycine Site Antagonists," *J. Cereb. Blood Flow Metab.* *15(2)*:188–196 (1995).

Yamada, K.A., et al., "Quantitative Physiological Characterization of a Quinoxalinedione non–NMDA Receptor Antagonist," *J. Neurosci.* *9(9)*:3230–3236 (1989).

Yoneda, Y., and Ogita, K., "Abolition of the NMDA–mediated responses by a specific glycine antagonist, 6,7–dichloroquinoxaline–2,3–dione (DCQX)," *Biochem. Biophys. Res. Comm.* *164(2)*:841–849 (1989).

ALKYL, AZIDO, ALKOXY AND FLUORO-SUBSTITUTED AND FUSED QUINOXALINEDIONES AND THE USE THEREOF AS GLYCINE RECEPTOR ANTAGONIST

CROSS REFERENCE TO RELATED APPLICATIONS

This application is a divisional of U.S. application Ser. No. 08/792,872, filed Jan. 31, 1997, U.S. Pat. No. 5,977,107, which is a divisional of U.S. application Ser. No. 08/289,603, filed Aug. 11, 1994, now U.S. Pat. No. 5,631,373, which is a continuation-in-part of U.S. application Ser. No. 08/208,878, filed Mar. 11, 1994, abandoned, which is a continuation-in-part of U.S. application Ser. No. 08/148,268, filed Nov. 5, 1993, abandoned, and a continuation-in-part of U.S. application Ser. No. 08/148,259, filed Nov. 5, 1993, now U.S. Pat. No. 5,514,680.

This invention was made with government support under grant numbers NIDA DA 06727, NIDA DA 06356, and NIDA DA 06726 awarded by the National Institutes of Health. The U.S. government has certain rights in the invention.

BACKGROUND OF THE INVENTION

1. Field of the Invention

The present invention is in the field of medicinal chemistry and relates to compounds that have a high affinity for the glycine binding site, lack PCP side effects, and cross the blood brain barrier at high levels. In particular, the present invention relates to novel alkyl, azido, alkoxy, fluoro-substituted, and fused 1,4-dihydroquinoxaline-2,3-diones and their use to treat or prevent neuronal degeneration associated with ischemia, pathophysiologic conditions associated with neuronal degeneration, convulsions, anxiety, chronic pain, and to induce anesthesia.

2. Description of the Related Art

Glutamate is thought to be the major excitatory neurotransmitter in the brain. There are three major subtypes of glutamate receptors in the CNS. These are commonly referred to as kainate, AMPA, and N-methyl-D-aspartate (NMDA) receptors (Watkins and Olverman, *Trends in Neurosci.* 7:265–272 (1987)). NMDA receptors are found in the membranes of virtually every neuron in the brain. NMDA receptors are ligand-gated cation channels that allow $Na^+$, $K^+$, and $Ca^{++}$ to permeate when they are activated by glutamate or aspartate (non-selective, endogenous agonists) or by NMDA (a selective, synthetic agonist) (Wong and Kemp, *Ann. Rev. Pharmacol. Toxicol.* 31:401–425 (1991)).

Glutamate alone cannot activate the NMDA receptor. In order to become activated by glutamate, the NMDA receptor channel must first bind glycine at a specific, high affinity, glycine binding site that is separate from the glutamate/NMDA binding site on the receptor protein (Johnson and Ascher, *Nature* 325:329–331 (1987)). Glycine is therefore an obligatory co-agonist at the NMDA receptor/channel complex (Kemp, J. A., et al., *Proc. Natl. Acad. Sci. USA* 85:6547–6550 (1988)).

In addition to the binding sites for glutamate/NMDA and glycine, the NMDA receptor carries a number of other functionally important binding sites. These include binding sites for $Mg^{++}$, $Zn^{++}$, polyamines, arachidonic acid, and phencyclidine (PCP) (Reynolds and Miller, *Adv. in Pharmacol.* 21:101–126 (1990); Miller, B., et al., *Nature* 355:722–725 (1992)). The PCP binding site—now commonly referred to as the PCP receptor-is located inside the pore of the ionophore of the NMDA receptor/channel complex (Wong, E. H. F., et al., *Proc. Natl. Acad. Sci. USA* 83:7104–7108 (1986); Huettner and Bean, *Proc. Natl. Acad. Sci. USA* 85:1307–1311 (1988); MacDonald, J. F., et al., *Neurophysiol.* 58:251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glutamate and glycine (Sircar and Zukin, *Brain Res.* 556:280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK801. This drug has a $K_d$ of approximately 3 nM at the PCP receptor (Wong, E. H. F., et al., *Proc. Natl. Acad. Sci. USA* 83:7104–7108 (1986)).

Both PCP and MK801 as well as other PCP receptor ligands, e.g., dextromethorphan, ketamine, and N,N'-disubstituted guanidines, have neuroprotective efficacy both in vitro and in vivo (Gill, R., et al., *J. Neurosci.* 7:3343–3349 (1987); Keana, J. F. W., et al., *Proc. Natl. Acad. Sci. USA* 86:5631–5635 (1989); Steinberg, G. K., et al., *Neuroscience Lett.* 89: 193–197 (1988); Church, J., et al., In: *Sigma and Phencyclidine-Like Compounds as Molecular Probes in Biology*, Domino and Kamenka, eds., Ann Arbor: NPP Books, pp. 747–756 (1988)). The well-characterized neuroprotective efficacy of these drugs is largely due to their capacity to block excessive $Ca^{++}$ influx into neurons through NMDA receptor channels, which become over activated by excessive glutamate release in conditions of brain ischemia (e.g. in stroke, cardiac arrest ischemia etc.) (Collins, R. C., *Metabol. Br. Dis.* 1:231–240 (1986); Collins, R. C., et al., *Annals Int. Med.* 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation hyperlocomotion) in rodents (Tricklebank, M. D., et al., *Eur. J. Pharmacol.* 167:127–135 (1989)) and a characteristic catalepsy in pigeons (Koek, W., et al., *J. Pharmacol Exp. Ther.* 245:969 (1989); Willets and Balster, *Neuropharmacology* 27:1249 (1988)); in drug discrimination paradigms, there is a strong correlation between the PCP receptor affinity of these drugs and their potency to induce a PCP-appropriate response behavior (Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)).

Drugs acting as competitive antagonists at the glutamate binding site of the NMDA receptor, such as, CGS 19755 and LY274614, also have neuroprotective efficacy because these drugs-like the PCP receptor ligands—can prevent excessive Ca$^{++}$ flux through NMDA receptor/channels in ischemia (Boast, C. A., et al., *Brain Res.* 442:345–348 (1988); Schoepp, D. D., et al., *J. Neural. Trans.* 85:131–143 (1991)). However, competitive NMDA receptor antagonists also have PCP-like behavioral side-effects in animal models (behavioral excitation, activity in PCP drug discrimination tests) although not as potently as MK801 and, PCP (Tricklebank, M. D., et al., *Eur. J. Pharmacol.* 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson and Ascher, *Nature* 325:329–331 (1987); Kemp, J. A., et al., *Proc. Natl. Acad. Sci. USA* 85:6547–6550 (1988)), a glycine antagonist can completely prevent ion flux through the NMDA receptor channel—even in the presence of a large amount of glutamate.

Recent in vivo microdialysis studies have demonstrated that, in the rat focal ischemia model, there is a large increase in glutamate release in the ischemic brain region with no significant increase in glycine release (Globus, M. Y. T., et al., *J. Neurochem.* 57:470–478 (1991)). Thus, theoretically, glycine antagonists should be very powerful neuroprotective agents because they can prevent the opening of NMDA channels by glutamate non-competitively and, therefore, unlike competitive NMDA antagonists, do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988); Tricklebank, M. D., et al., *Eur. J. Pharmacol.* 167:127–135 (1989); Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167:127–135 (1989)).

However, there have been two major problems that have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85:6547–6550 (1988)), 5,7-dichlorokynurenic acid (McNamara, D., et al., *Neuroscience Lett.* 120:17–20 (1990)) and indole-2-carboxylic acid (Gray, N. M., et al., *J. Med. Chem.* 34:1283–1292 (1991)) cannot penetrate the blood/brain barrier and therefore have no utility as therapeutic agents;

B. The only available glycine antagonist that sufficiently penetrates the blood/brain barrier—the drug HA-966 (Fletcher and Lodge, *Eur. J. PharmacoL* 151:161–162 (1988))—is a partial agonist with only micromolar affinity for the glycine binding site. A neuroprotective efficacy for HA-966 in vivo has, therefore, not been demonstrated, nor has it been demonstrated for the other available glycine antagonists because they lack bioavailability in vivo.

However, one recent success in identifying orally active glycine receptor antagonists was reported by Kulagowski et al., *J. Med. Chem.* 37:1402–1405 (1994), who disclose that 3-substituted 4-hydroxyquinoline-2(1H)-ones are selective antagonists possessing potent potent in vivo activity.

There have been a number of reports in the literature of substituted 1,4-dihydroquinoxaline-2,3-diones that are useful for treating pathophysiologic conditions mediated by the non-NMDA, NMDA, and glycine receptors. For example, U.S. Pat. No. 4,975,430 discloses 1,4-dihydroquinoxaline-2,3-dione compounds of the formula:

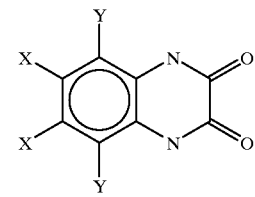

wherein each X is independently nitro or cyano and wherein each Y is independently H, lower alkyl, lower alkoxy, or CF$_3$. These compounds are reportedly useful for the treatment of neuronal conditions associated with stimulation of the NMDA receptor.

U.S. Pat. No. 3,962,440 discloses 1,4-dihydroquinoxaline-2,3-dione compounds having the formula:

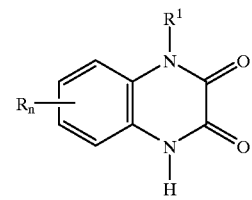

wherein, R$^1$ can be hydrogen or methyl, R$_n$ can be lower alkyl, lower alkoxy, lower alkylthio, cyclopropyl, nitro, cyano, halogen, fluoroalkyl of C$_1$–C$_2$ (trifluoromethyl) amino, or substituted amino, and n can be 0, 1, or 2. These compounds are reportedly useful as hypnotic agents.

U.S. Pat. No. 4,812,458 discloses 1,4-dihydroquinoxaline-2,3-dione compounds having the formula:

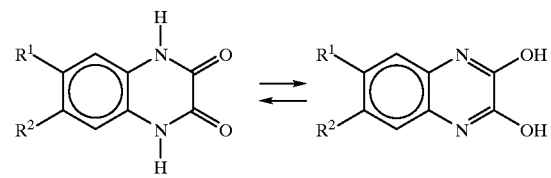

wherein $R^1$ is halogen, cyano, trifluoromethyl, ethynyl, or $N_3$, and $R^2$ is $SO_2C_{1-3}$-alkyl, trifluoromethyl, nitro, ethynyl, or cyano. These compounds are reportedly useful for treatment of indications caused by hyperactivity of the excitatory neurotransmitters, particularly the quisqualate receptors, and as neuroleptics.

U.S. Pat. No. 4,659,713 discloses 1,4-dihydroquinoxaline-2,3-dione compounds having the formula:

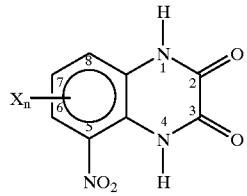

wherein X represents hydrogen, chloro, bromo, fluoro, iodo, trichloromethyl, dichlorofluoromethyl, difluoromethyl, or trifluoromethyl, and n represents 1 or 2. These compounds are reportedly useful for the control of coccidiosis in animals.

U.S. Pat. No. 4,948,794 discloses 1,4-dihydroquinoxaline-2,3-dione compounds having the formula:

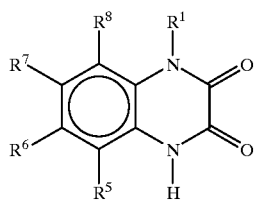

wherein $R^1$ is $C_{1-12}$-alkyl, which may, optionally, be substituted by hydroxy, formyl, carboxy, carboxylic esters, amides, or amines, $C_{3-8}$-,cycloalkyl, aryl, aralkyl; and wherein $R^6$ is, hydrogen, halogen, CN, $CF_3$, $NO_2$, or OR', wherein R' is $C_{1-4}$-alkyl, and $R^5$, $R^7$, and $R^8$ are hydrogen, provided $R^6$ is not $CF_3$, $OCH_3$, $NO_2$, Cl, or Br when $R^1$ is $CH_3$; or $R^6$ and $R^7$ independently are $NO_2$, halogen, CN, $CF_3$, or OR', wherein R' is $C_{1-4}$-alkyl, and $R^5$ and $R^8$ are each hydrogen; or $R^5$ and $R^6$ together form a further fused aromatic ring, which may be substituted with halogen, $NO_2$, CN, $CF_3$, or OR', wherein R' is $C_{1-4}$-alkyl; or $R^7$ and $R^8$ together form a further fused aromatic ring, which may be substituted with halogen, $NO_2$, CN, $CF_3$, or OR', wherein R' is $C_{1-4}$-alkyl, and $R^5$ and $R^6$ independently are hydrogen, halogen, CN, $CF_3$, $NO_2$, or OR', wherein R' is $C_{1-4}$-alkyl. These compounds are reportedly useful for the treatment of indications caused by hyperactivity of the excitatory neurotransmitters, particularly the quisqualate receptors, and as neuroleptics.

Yoneda and Ogita, *Biochem. Biophys. Res. Commun.* 164:841–849 (1989), disclose that the following 1,4-dihydroquinoxaline-1,2-dione competitively displaced the strychnine-insensitive binding of [$^3$H]glycine, without affecting the other binding sites on the NMDA receptor complex:

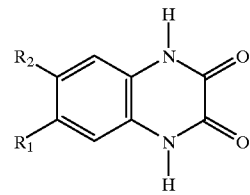

| $R_1$ | $R_2$ | |
|---|---|---|
| H | H | QX |
| Cl | H | CQX |
| Cl | Cl | DCQX |
| $NO_2$ | CN | CNQX |
| $NO_2$ | $NO_2$ | DNQX |

According to the authors, the structure-activity relationships among quinoxalines clearly indicates that both chloride groups of the positions 6 and 7 in the benzene ring are crucial for the antagonist potency against the Gly sites. Removal of one chloride from the molecule results in a 10-fold reduction in the affinity for Gly sites.

Kleckner and Dingledine, *Mol. Pharm.* 36:430436 (1989), disclose that 6,7-dinitro-1,4-dihydroquinoxaline-2,3-dione and 6-cyano-7-nitro-1,4-dihydroquinoxaline-2,3-dione are more potent antagonists of kainate than glycine, but substitution of Cl at the 6- position and especially at the 6- and 7-positions increases potency at the glycine site. In addition, the authors suggest that antagonists of the glycine site might be effective against NMDA receptor-mediated neuropathologies.

Rao, T. S. et al., *Neuropharmacology* 29:1031–1035 (1990), disclose that 6,7-dinitro-1,4-dihydroquinoxaline-2,3-dione and 7-cyano-6-nitro-1,4-dihydroquinoxaline-2,3-dione antagonize responses mediated by NMDA-associated glycine recognition sites in vivo.

Pellegrini-Giampietro, D. E. et al., *Br. J. Pharmacol.* 98:1281–1286 (1989), disclose that 6-cyano-7-nitro-1,4-dihydroquinoxaline-2,3-dione and 6,7-dinitro-1,4-dihydroquinoxaline-2,3-dione can antagonize the responses to L-glutamate by interacting with the glycine recognition sites of the NMDA receptor ion channel complex.

Ogita and Yoneda, *J. Neurochem.* 54:699–702 (1990), disclose that 6,7-dichloro-1,4-dihydroquinoxaline-2,3-dione is a competitive antagonist specific to the strychnine-insensitive [$^3$H] glycine binding sites on the NMDA receptor complex. According to the authors, the two chloride radicals at the 6- and 7-positions in the benzene ring of the quinoxaline are crucial for the antagonistic potency against the glycine binding sites.

Kessler, M. et al., *Brain Res.* 489:377–382 (1989), disclose that 6,7-dinitro-1,4-dihydroquinoxaline-2,3-dione and 6-cyano-7-nitro-1,4-dihydroquinoxaline-2,3-dione inhibit [$^3$H] glycine binding to the strychnine-insensitive glycine binding sites associated with NMDA receptors.

European Patent Application Publication No. 0 377 112, published Jul. 11, 1990, discloses 1,4-dihydroquinoxaline-2,3-dione compounds having the formula:

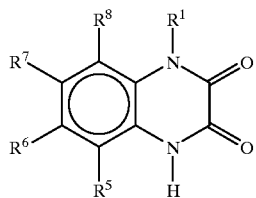

wherein, inter alia, $R^1$ can be hydroxy, alkoxy, aryloxy, aralkyloxy, cycloalkylalkoxy, cycloalkoxy, or alkanoyloxy; and $R^5$, $R^6$, $R^7$ and $R^8$ can be independently hydrogen, nitro, halogen, cyano, trifluoromethyl, $SO_2NR'R'$, $SO_2R'$ or $OR'$, wherein R' is hydrogen or $C_{1-4}$ alkyl. These compounds are reportedly useful for the treatment of indications caused by hyperactivity of the excitatory neurotransmitters, particularly the quisqualate receptors, and as neuroleptics.

Lester, R. A. et al., *Mol. Pharm.* 35:565–570 (1989), disclose that 6-cyano-7-nitro-1,4-dihydroquinoxaline-2,3-dione antagonizes NMDA receptor-mediated responses by a competitive interaction of the glycine binding site.

Patel, J. et al., *J. Neurochem.* 55:114–121 (1990), disclose that the neuroprotective activity of 6,7-dinitro-1,4-dihydroquinoxaline-2,3-dione is due to antagonism of the coagonist activity of glycine at the NMDA receptor-channel complex.

Horner, L. et al., *Chem. Abstracts* 48:2692 (1953) disclose 6,8-dinitro-1,4-dihydroquinoxaline-2,3-dione.

Cheeseman, G. W. H., *J. Chem. Soc.*:1170–1176 (1962), discloses 6,7-dibromo-2,3-dihydroxyquinoxaline (also known as 6,7-dibromo-1,4-dihydroquinoxaline-2,3-dione).

Honore, T. et al., *Science* 241:701–703 (1988), disclose that 6,7-dinitro-1,4-dihydroquinoxaline-2,3-dione and 7-cyano-6-nitro-1,4-dihydroquinoxaline-2,3-dione are potent non-NMDA glutamate receptor antagonists.

Sheardown, M. J. et al., *Eur. J. Pharmacol.* 174:197–204 (1989), disclose that 5,7-dinitro-1,4-dihydroquinoxaline-2,3-dione is a potent antagonist of the strychnine insensitive glycine receptor and has anticonvulsant properties. However, Sheardown et al. also disclose that 5,7-dinitro-1,4-dihydroquinoxaline-2,3-dione as well as DNQX and CNQX have poor access to the central nervous system.

International Application Publication No. WO91/13878 discloses the following N-substituted 1,4-dihydroquinoxaline-2,3-diones, which bind to the glycine receptor:

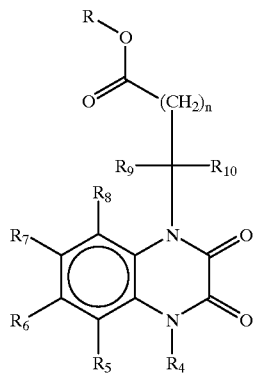

wherein R represents hydrogen, $C_{1-6}$ alkyl, or aralkyl, and n is an integer from 0 to 5; $R^4$ represents hydrogen or hydroxy; $R^5$, $R^6$, $R^7$, and $R^8$ independently represent hydrogen, nitro, halogen, alkoxy, aryloxy, aralkoxy, $C_{1-6}$-alkyl, or aryl; $R^9$ represents hydrogen, lower alkyl, or aryl; $R^{10}$ represents hydrogen, or alkyl, and pharmaceutically acceptable salts thereof.

Leeson et al., *J. Med. Chem.* 34:1243–1252 (1991), disclose a number of derivatives of the nonselective excitatory amino acid antagonist kynurenic acid. Also disclosed are a number of structurally related quinoxaline-2,3-diones that are also glycine/NMDA antagonists, but are not selective and are far less potent than the kynurenic acid derivatives. The quinoxaline-2,3-diones have the structure:

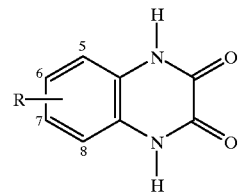

wherein R is H, 5-Cl, 7-Cl, 5,7-$Cl_2$, 6,7-$Cl_2$, 6,7-$(CH_3)_2$, 6-$NO_2$, or 6,7-$(NO_2)_2$. Also disclosed are a number of N-methyl derivatives.

Epperson et al., *Bioorganic & Medicinal Chemistry Letters*, 3(12):2801–2804 (1993) report the synthesis and amino acid pharmacology of twelve N-substituted quinoxalinediones. In particular, compounds of the structure

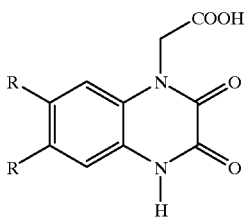

4a R = $CH_3$
4b R = Cl are reported to have significant antagonism at both the AMPA and glycine-site NMDA receptors. The functional antagonism of 4a has been demonstrated. By way of background, the authors teach that quinoxalinediones such as 6,7-dinitroquinoxaline-2,3-dione and 6cyano-7-nitroquinoxaline-2,3-dione and 6-cyano-7dnitroquinoxaline-2,3-dione have been shown to be AMPA (Honore et al., *Science* 241:701 (1988)) as well as glycine antagonists (Birch et al., *Eur. J. Pharmacol.* 156:177 (1988)), and also to be neuroprotective in vitro (Frandson, et al., *J. Neurochem.* 53:297 (1989)) and the AMPA selective quinoxalinedione 2,3-dihydroxy-6-nitro-7-sufamoyl-benzo (F) quinoxaline has been shown to be neuroprotective in cerebral ischemia models (Sheardown et al., *Science* 247:571 (1990)).

For a recent review on glycine antagonists, reference is made to Leeson, P. D., "Glycine-Site N-Methyl-D-Aspartate Receptor Antagonists," Chapter 13 in *Drug Design for Neuroscience, Kozikowski,* A. P. (ed.), Raven Press, New York, pp. 338–381 (1993).

A need continues to exist for potent and selective glycine/NMDA antagonists that:
lack the PCP-like behavioral side effects common to the PCP-like NMDA channel blockers, such as, MK801, or to the competitive NMDA receptor antagonists, such as, CGS19755;
show potent anti-ischemic efficacy because of the non-competitive nature of their glutamate antagonism at the NMDA receptor;

cross the blood-brain barrier at levels sufficient for efficacy;

have utility as novel anticonvulsants with fewer side-effects than the PCP-like NMDA channel blockers or the competitive NMDA antagonists;

help in defining the functional significance of the glycine binding site of the NMDA receptor in vivo.

SUMMARY OF THE INVENTION

The present invention relates to the discovery of a class of compounds that exhibit high affinity for the strychnine-insensitive glycine binding site, that do not exhibit PCP side effects, and that cross the blood brain barrier at high levels. Such compounds include alkyl, azido, alkoxy, hydroxy, and fluoro-substituted 1,4-quinoxaline-2,3-diones, as well as ring fused 1,4-quinoxaline-2,3-diones. The high affinity of alkyl-substituted 1,4-quinoxaline-2,3-diones to the glycine binding site was unexpected, in view of the many reports in the literature that the presence of electron withdrawing groups on the benzene nucleus is required for high binding affinity and that alkyl and alkoxy groups are electron donating and azido is only weakly electron withdrawing.

The invention also relates to a method of treating or preventing neuronal loss associated with stroke, ischemia, CNS trauma, hypoglycemia, and surgery; treating neurodegenerative diseases, including, Alzheimer's disease, amyotrophic lateral sclerosis, Huntington's disease, and Down's syndrome; treating or preventing the adverse consequences of the overstimulation of the excitatory amino acids; treating anxiety, convulsions, chronic pain, or psychosis; preventing opiate tolerance; or inducing a hypnotic effect or anesthesia comprising administering to an animal in need of such treatment or prevention a substituted 1,4-dihydroquinoxaline-2,3-dione, as defined herein, having high affinity for the glycine binding site and the capability of crossing the blood brain barrier at high levels, while lacking PCP side effects.

The compounds of the present invention include those having the Formula I:

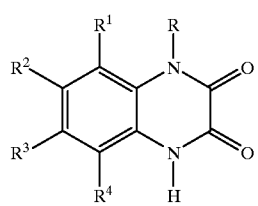

I or a tautomer thereof;

wherein

R is hydrogen, hydroxy, amino, —$CH_2CONHAr$, —$NHCONHAr$, —$NHCOCH_2Ar$, —$COCH_2Ar$, wherein Ar is an aryl group, or a radical having the formula:

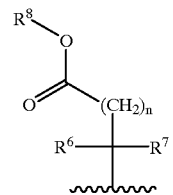

(II)

wherein $R^6$ is hydrogen, lower alkyl of 1–6 carbon atoms or aryl; $R^7$ is hydrogen or lower alkyl of 1–6 carbon atoms; n is an integer from 0 to 5; and $R^8$ is hydrogen, $C_{1-6}$ alkyl, or aralkyl;

$R^1$, $R^2$, $R^3$, and $R^4$ are independently selected from the group consisting of hydrogen, hydroxy, acyloxy, aralkoxy, amino, alkanoylamino, halo, haloalkyl, nitro, alkyl, alkoxy, carboxy, alkanoyl, thioalkyl, alkoxyalkyl, aryloxyalkyl, arylalkyl, alkenyl, alkynyl, arylalkenyl, arylalkynyl, cyano, cyanomethyl, dicyanomethyl, cyanoamino, dicyanoamino, or azido; or where $R^1$ and $R^2$, $R^2$ and $R^3$, or $R^3$ and $R^4$ form a fused 5- or 6-membered carbocyclic, heterocyclic, aromatic or heteroaromatic ring.

Preferably, at least one of $R^1$-$R^4$ is alkyl, alkoxy, hydroxy, or azido, or $R^1$ is cyano, or $R^1$ and $R^2$, $R^2$ and $R^3$, or $R^3$ and $R^4$ form a fused 5- or 6-membered carbocyclic, heterocyclic, aromatic, or heteroaromatic ring.

The invention also relates to certain compounds found to have exceptional in vivo activity and having the Formula (III)

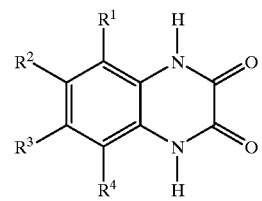

(III)

or a tautomer thereof;
wherein
$R^1$ is nitro, fluoro, or chloro;
$R^2$ is fluoro, chloro, alkyl, alkoxy, or azido;
$R^3$ is fluoro or chloro; and
$R^4$ is hydrogen or fluoro;
with the proviso that at least one of $R^1$–$R^4$ is fluoro, and that $R^2$ and $R^4$ are not fluoro when $R^1$ is nitro.

The invention also relates to certain compounds having the Formula III or a tautomer thereof, wherein $R^1$ is nitro, cyano, $CF_3$, carboxy, or alkanoyl;
$R^2$ is alkoxy, aralkoxy, thioalkyl, carboxy, alkanoyl, hydroxy, mercaptoalkyl, azido, or $NR^5R^6$, wherein $R^5$ and $R^6$ are independently hydrogen, alkyl, or aryl groups;
$R^3$ is halo, haloalkyl, nitro, alkyl, alkoxy, azido, or cyano; and
$R^4$ is hydrogen.

The invention also relates to a method for the preparation of a 1,4-dihydroquinoxaline-2,3-dione having the Formula (IV):

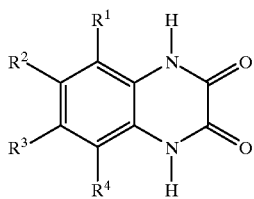

or a tautomer thereof;
wherein
$R^1$ is nitro;
$R^2$ is haloalkyl, halo, cyano, alkyl, or alkoxy;
$R^3$ is haloalkyl, halo, cyano, alkyl, or alkoxy; and
$R^4$ is hydrogen; comprising reaction of a compound having the Formula (V):

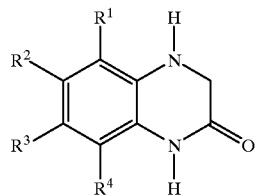

or a tautomer thereof;
wherein
$R^1$ is hydrogen;
$R^2$ is haloalkyl, halo, cyano, alkyl, or alkoxy;
$R^3$ is haloalkyl, halo, cyano, alkyl, or alkoxy; and
$R^4$ is hydrogen;
with fuming nitric acid; and isolating the 1,4-dihydroquinoxaline-2,3-dione so produced.

The invention also relates to a method for the preparation of a compound having the Formula (VI):

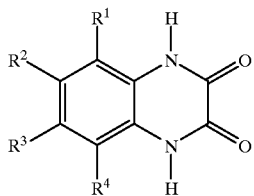

or a tautomer thereof;
wherein
$R^1$ is nitro, cyano, $CF_3$, carboxy, or alkanoyl;
$R^2$ is alkoxy, aralkoxy, hydroxy, mercaptoalkyl, azido, or $NR^5R^6$, wherein $R^5$ and $R^6$ are independently hydrogen, alkyl, or aryl groups;
$R^3$ is halo, haloalkyl, nitro, alkyl, alkoxy, azido, or cyano; and
$R^4$ is hydrogen;
comprising reaction of a compound having the Formula (VII):

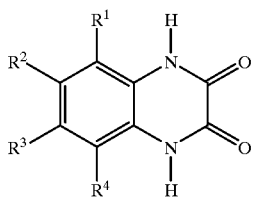

or a tautomer thereof;
wherein
$R^1$ is nitro, cyano, $CF_3$, carboxy, or alkanoyl;
$R^2$ is fluoro;
$R^3$ is halo, haloalkyl, nitro, alkyl, alkoxy, azido, or cyano; and
$R^4$ is hydrogen;
with an alkoxide, aryl alkoxide, hydroxide, an alkyl mercaptide, azide, or $HNR^5R^6$ respectively, in an inert solvent, and isolating the compound so produced.

In one embodiment, the present invention relates to a method of treating or preventing (A) neuronal loss associated with stroke, ischemia, CNS trauma, or hypoglycemia or (B). the adverse neurological consequences of surgery, comprising administering to an animal in need of such treatment or prevention an effective amount of a compound of the Formula I or a tautomer thereof.

In a second embodiment, the present invention relates to a method of treating a neurodegenerative disease selected from Alzheimer's disease, amyotrophic lateral sclerosis, Huntington's disease, and Down's syndrome, comprising administering to an animal in need of such treatment an effective amount of a compound of the Formula I or a tautomer thereof.

In a third embodiment, the present invention relates to a method of antagonizing excitatory amino acids at the NMDA receptor complex, comprising administering to an animal in need thereof an effective amount of a compound of the Formula I or a tautomer thereof.

In a fourth embodiment, the present invention relates to a method of treating or preventing the adverse consequences of the hyperactivity of the NMDA receptor, comprising administering to an animal in need of such treatment or prevention an effective amount of a compound of the Formula I or a tautomer thereof.

In a fifth embodiment, the present invention relates to a method of treating chronic pain, comprising administering to an animal in need of such treatment an effective amount of a compound of the Formula I or a tautomer thereof.

In a sixth embodiment, the present invention relates to a method of treating or preventing anxiety, comprising administering to an animal in need of such treatment or prevention an effective amount of a compound of the Formula I or a tautomer thereof.

In a seventh embodiment, the present invention relates to a method of treating or preventing convulsions, comprising administering to an animal in need of such treatment or prevention an effective amount of a compound of the Formula I or a tautomer thereof.

In an eighth embodiment, the present invention relates to a method of inducing anesthesia, comprising administering to an animal in need of such anesthesia an effective amount of a compound of the Formula I or a tautomer thereof.

In a ninth embodiment, the present invention relates to a method of treating or preventing NMDA receptor-ion channel related psychosis, comprising administering to an animal in need of such treatment or prevention an effective amount of a compound of the Formula I or a tautomer thereof.

In a tenth embodiment, the present invention relates to a method of inducing a hypnotic effect, comprising administering to an animal in need of such treatment an effective amount of a compound having the Formula I or a tautomer thereof.

In an eleventh embodiment, the present invention relates to a radiolabelled compound having the Formula I or a tautomer thereof.

In a twelfth embodiment, the present invention relates to a pharmaceutically acceptable salt of a compound having the Formula I or a tautomer thereof.

In a thirteenth embodiment, the present invention relates to a method of preventing opiate tolerance, comprising administering to an animal in need of such prevention an effective amount of a compound of the Formula

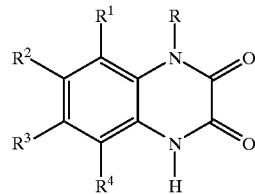

or a tautomer thereof;
wherein
R is hydrogen, hydroxy, amino, —$CH_2CONHAr$, —$NHCONHAr$, —$NHCOCH_2Ar$, —$COCH_2Ar$, wherein Ar is an aryl group, or a radical having the formula:

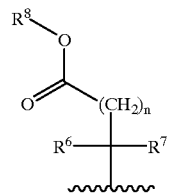

wherein $R^6$ is hydrogen, lower alkyl of 1–6 carbon atoms, or aryl; $R^7$ is hydrogen or lower alkyl of 1–6 carbon atoms; n is an integer from 0 to 5; and $R^8$ is hydrogen, $C_{1-6}$ alkyl, or aralkyl;

$R^1$, $R^2$, $R^3$, and $R^4$ are independently selected from the group consisting of hydrogen, hydroxy, acyloxy, aralkoxy, amino, alkanoylamino, halo, haloalkyl, nitro, alkyl, alkoxy, carboxy, alkanoyl, thioalkyl, alkoxyalkyl, aryloxyalkyl, arylalkyl, alkenyl, alkynyl, arylalkenyl, arylalkynyl, cyano, cyanomethyl, dicyanomethyl, cyanoamino, dicyanoamino, or azido; or where $R^1$ and $R^2$, $R^2$ and $R^3$, or $R^3$ and $R^4$ form a fused 5- or 6-membered carbocyclic, heterocyclic, aromatic or heteroaromatic ring.

DESCRIPTION OF THE PREFERRED EMBODIMENTS

Figure 1:
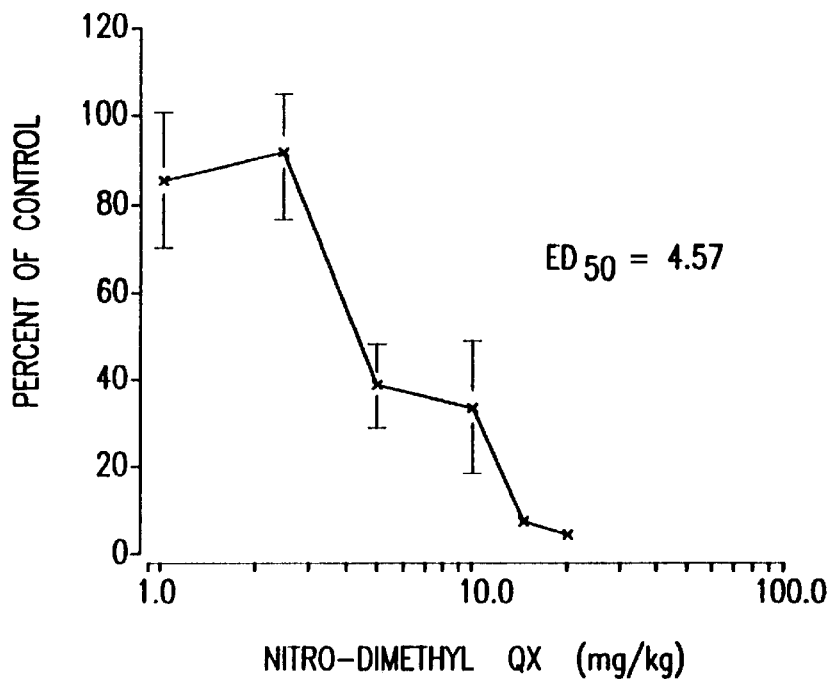
FIG. 1 depicts a graph showing the effect of 5-nitro-6,7-dimethylquinoxalinedione (NDMQX) on the early phase of the formalin test for pain.

The present invention relates to compounds having a high affinity for the glycine binding site and the capability of crossing the blood brain barrier at high levels, while lacking PCP side effects. Such compounds include alkyl, azido, alkoxy, and fluoro-substituted 1,4-dihydroquinoxaline-2,3-diones, which are highly selective, competitive antagonists of the glycine binding site of the NMDA receptor. Certain of the 1,4-dihydroquinoxaline-2,3-diones of the invention have the following Formula (I):

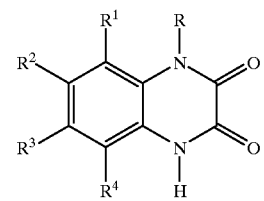

I or a tautomer thereof;
wherein
R is hydrogen, hydroxy, amino, —$CH_2CONHAr$, —$NHCONHAr$, —$NHCOCH_2Ar$, —$COCH_2Ar$, wherein Ar is an aryl group, or a radical having the formula:

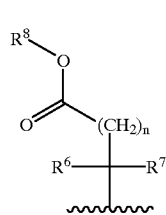

II wherein $R^6$ is hydrogen, lower alkyl of 1–6 carbon atoms, or aryl; $R^7$ is hydrogen or lower alkyl of 1–6 carbon atoms; n is an integer from 0 to 5; and $R^8$ is hydrogen, $C_{1-6}$ alkyl, or aralkyl;

$R^1$, $R^2$, $R^3$, and $R^4$ are independently selected from the group consisting of hydrogen, hydroxy, acyloxy, aralkoxy, amino, alkanoylamino, halo, haloalkyl, nitro, alkyl, alkoxy, carboxy, alkanoyl, thioalkyl, alkoxyalkyl, aryloxyalkyl, arylalkyl, alkenyl, alkynyl, arylalkenyl, arylalkynyl, cyano, cyanomethyl, dicyanomethyl, cyanoamino, dicyanoamino, or azido; or where $R^1$ and $R^2$, $R^2$ and $R^3$, or $R^3$ and $R^4$ form a fused 5- or 6-membered carbocyclic, heterocyclic, aromatic, or heteroaromatic ring;

with the proviso that at least one of $R^1$–$R^4$ is alkyl, alkoxy, aralkoxy, hydroxy, carboxy, alkanoyl, or azido, or that $R^1$ is cyano, or that $R^1$ and $R^2$, $R^2$ and $R^3$, or $R^3$ and $R^4$ form a 5- or 6-membered carbocycloalkyl, heterocyclic, aromatic, or heteroaromatic ring.

Of course, it is to be understood that $R^1$–$R^4$ can be the same or different.

In preferred compounds within the scope of Formula I, $R^1$ is alkyl, azido, alkoxy, hydroxy, haloakyl, halo, nitro, cyano, or alkanoylamino; $R^2$ is alkyl, azido, alkoxy, aralkoxy, cyano, haloalkyl, halo, hydroxy, or nitro; $R^3$ is alkyl, azido, alkoxy, cyano, halo, haloalkyl, or hydroxy; and $R^4$ is alkyl, azido, alkoxy, cyano, hydroxy, or hydrogen; but at least one of $R^1$–$R^4$ is alkyl, alkoxy, hydroxy, or azido, or $R^1$ is cyano. Especially preferred compounds are those where $R^1$ is alkyl, azido, alkoxy, cyano, hydroxy, or nitro; $R^2$ is alkyl, azido, alkoxy, aralkoxy, cyano, hydroxy, or halo; $R^3$ is alkyl, azido, alkoxy, halo, cyano, hydroxy, or haloalkyl; and $R^4$ is alkyl, alkoxy, azido, cyano, hydroxy, or hydrogen; but where at least one of $R^1$–$R^4$ is alkyl, alkoxy, hydroxy, or azido, or $R^1$ is cyano. In general, the most preferred compounds are substituted by hydrogen or fluorine at position $R^4$ when R is other than hydrogen. When R is hydrogen, the most preferred compounds are those where $R^4$ is hydrogen or fluoro and $R^1$–$R^3$ are other than hydrogen.

Other preferred compounds are substituted by an arylalkyl, arylalkenyl, arylalkynyl, or aryloxyalkyl group in the 6-position of the 1,4-dihydroquinoxaline-2,3-dione ring. Such compounds are expected to show increased lipophilicity and, therefore, ability to cross the blood-brain barrier. Such compounds are also expected to bind favorably to a hypothetical hydrophobic binding pocket that might be present at a position 10 o'clock to the 1,4-dihydroquinoxaline-2,3-dione ring. Alternatively, a long chain alkanoylamido group (an acylamino group) can be present at the 5-position of the ring to interact with this binding pocket.

Where the 1,4-dihydroquinoxaline-2,3-dione is substituted by a radical having Formula II, the radical can be a $C_{2-7}$carboxyalkyl group including carboxymethyl, 2-carboxyethyl, 3-carboxypropyl, 4-carboxybutyl, 5-carboxypentyl, 6-carboxyhexyl, 1-carboxyethyl, 1-carboxypropyl, 1-carboxybutyl, 1-carboxypentyl, 1-carboxyhexyl, 2-carboxypropyl, 2-carboxybutyl, 2-carboxypentyl, 2-carboxyhexyl, 3-carboxybutyl, 3-carboxypentyl, 3-carboxyhexyl, 5-carboxypentyl, 5-carboxyhexyl, and the like.

Typical $C_{8-12}$ carboxyaralkyl groups that are included in Formula II include 1-aryl-2-carboxyethyl, 1-aryl-3 carboxypropyl, 1-aryl-4-carboxybutyl, 1-aryl-5-carboxypentyl, 1aryl-6-carboxyhexyl, 1-aryl-1-carboxyethyl, 1-aryl-1-carboxypropyl, 1-aryl-1-carboxybutyl, 1-aryl-1-carboxypentyl, 1-aryl-1-carboxyhexyl, 1-aryl-2-carboxypropyl, 1-aryl-2-carboxybutyl, 1-aryl-2-carboxypentyl, 1-aryl-2-caroxyhexyl, 1-aryl-3-carboxybutyl, 1-aryl-3-carboxypentyl, 1-aryl-3-carboxyhexyl, 1-aryl-5-carboxypentyl, 2-aryl-5-carboxyhexyl, 2-aryl-2-carboxyethyl, 2-aryl-3-carboxypropyl, 2-aryl-4-carboxybutyl, 2-aryl-5-carboxypentyl, 2-aryl-6-carboxyhexyl, 2-aryl-1-carboxyethyl, 2-aryl-1-carboxypropyl, 2-aryl-1-carboxybutyl, 2-aryl-1-carboxypentyl, 2-aryl-1-carboxyhexyl, 2-aryl-2-carboxypropyl, 2-aryl-2-carboxybutyl, 2-aryl-2-carboxypentyl, 2-aryl-2-carboxyhexyl, 2-aryl-3-carboxybutyl, 2-aryl-3-carboxypentyl, 2-aryl-3-carboxyhexyl, 1-aryl-5-carboxypentyl, 2-aryl-5-carboxyhexyl, and the like.

Typical $C_{1-6}$ alkyl groups include methyl, ethyl, propyl, isopropyl, butyl, isobutyl, sec-butyl, tert.-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Typical alkoxy groups include oxygen substituted by any of the $C_{1-6}$ alkyl groups mentioned above.

Typical thioalkyl groups include sulfur substituted by any of the $C_{1-6}$ alkyl groups mentioned above.

Typical alkoxyalkyl groups include any of the above alkyl groups substituted by an alkoxy group, such as methoxymethyl, ethoxymethyl, propoxymethyl, butoxymethyl, pentoxymethyl, hexoymethyl, methoxyethyl, methoxypropyl, methoxybutyl, methoxypentyl, methoxyhexyl, and the like.

Preferred aryl groups are $C_{6-14}$ aryl groups and typically include phenyl, naphthyl, fluorenyl, phenanthryl, and anthracyl groups.

Typical aralkoxy groups include the above alkoxy groups substituted by one or more of the above aryl groups, e.g., 3-phenylpropoxy, 2-phenylethoxy, and the like.

Typical aryloxyalkyl groups include any of the above alkyl groups substituted by an aryloxy group, such as, phenoxymethyl, phenoxyethyl, phenoxypropyl, phenoxybutyl, phenoxypentyl, phenoxyhexyl, and the like.

Typical arylalkyl groups include any of the above $C_{1-6}$ alkyl groups substituted by any of the $C_{6-14}$ aryl groups, including the group $Ph(CH_2)_n$, where n is 1–6, for example, benzyl, 2-phenethyl, 3-phenylpropyl, 2-phenylpropyl, 4-phenylbutyl, 5-phenylpentyl, and 6-phenylhexyl groups.

Typical $C_{2-6}$ alkenyl groups include ethenyl, 2-propenyl, isopropenyl, 2-butenyl, 3-butenyl, 4-pentenyl, 3-pentenyl, 2-pentenyl, 5-hexenyl, 4-hexenyl, 3-hexenyl, and 2-hexenyl groups.

Typical $C_{2-6}$ alkynyl groups include ethynyl, 2-propynyl, 2-butynyl, 3-butynyl, 4-pentynyl, 3-pentynyl, 2-pentynyl, 5-hexynyl, 4-hexynyl, 3-hexynyl, and 2-hexynyl groups.

Typical arylalkenyl groups include any of the above $C_{2-6}$ alkenyl groups substituted by any of the above $C_{6-14}$ aryl groups, e.g. 2-phenylethenyl, 3-phenyl-2-propenyl, 2-phenylisopropenyl, 4-phenyl-2-butenyl, 4-phenyl-3-butenyl, 5-phenyl4-pentenyl, 5-phenyl-3-pentenyl, 5-phenyl-2-pentenyl, 6-phenyl-5-hexenyl, 6-phenyl4-hexenyl, 6-phenyl-3-hexenyl, and 6-phenyl-2-hexenyl groups.

Typical arylalkynyl groups include any of the above $C_{2-6}$ alkynyl groups substituted by any of the above $C_{6-14}$ aryl groups, e.g. 2-phenylethynyl, 2-phenyl-2-propynyl, 4-phenyl-2-butynyl, 4-phenyl-3-butynyl, 5-phenyl4-pentynyl, 5-phenyl-3-pentynyl, 5-phenyl-2-pentynyl, 6-phenyl-5-hexynyl, 6-phenyl4-hexynyl, 6-phenyl-3-hexynyl, and 6phenyl-2-hexynyl groups.

Typical halo groups include fluorine, chlorine, bromine, and iodine.

Typical haloalkyl groups include $C_{1-6}$ alkyl groups substituted by one or more fluorine, chlorine, bromine, or iodine atoms, e.g. fluoromethyl, difluoromethyl, trifluoromethyl, pentafluoroethyl, 1,1-difluoroethyl, and trichloromethyl groups.

Typical amino groups include —NH$_2$, NHR$^9$, and —NR$^9$R$^{10}$, wherein each of R$^9$ and R$^{10}$ is one of the C$_{1-6}$ alkyl groups mentioned above. The amino group can also be substituted with one (—NHCN) or two (—N(CN)$_2$) cyano groups. These groups can be prepared by the reaction of the corresponding amine with cyanogen bromide.

Typical alkanoyl groups include C$_{1-5}$C(O) alkanoyl groups, e.g. acetyl, propionyl, butanoyl, pentanoyl, and hexanoyl groups, or by an arylalkanoyl group, e.g., a C$_{1-5}$C(O) alkanoyl group substituted by any of the above aryl groups.

As used herein, the term "acyloxy" means an alkanoyl group attached to the ring via an oxygen atom, e.g., acetyloxy, 2-phenylacetyloxy, and the like.

Typical alkanoylamino groups include an amino group substituted by one of the C$_{1-5}$C(O) alkanoyl groups.

Typical fused ring systems where R$^1$ and R$^2$, R$^2$ and R$^3$, or R$^3$ and R$^4$ are linked together to form a 5- or 6-membered carbocyloalkyl, heterocyclic, aromatic, or heteroaromatic group include benzo[g]quinoxaline, cyclohexo[g]quinoxaline, cyclopento[g]quinoxaline, thieno[g]quinoxaline, tetrahydrothieno[g]quinoxaline, furo[g]quinoxaline, tetrahydrofuro[g]quinoxaline, pyrano[g]quinoxaline, pyrrolo[g]quinoxaline, pyrido[g]quinoxaline, pyrazino[g]quinoxaline pyridazino[g]quinoxaline, 6,7-methylenedioxy-1,4-dihydroquinoxaline-2,3-dione, and 6,7-cyclic carbonate 1,4-dihydroquinoxaline-2,3-dione. The fused heterocyclic ring can bear a carbonyl group giving a fused lactone or lactam group.

Particularly preferred substituted 1,4-dihydroquinoxaline-2,3-diones of the present invention include, but are not limited to, 6,7-dimethyl-5-nitro-1,4-dihydroquinoxaline-2,3-dione; 6,7-dimethyl-1,4-dihydroquinoxaline-2,3-dione; 7-methyl-5-nitro-1,4-dihydroquinoxaline-2,3-dione; 7-fluoro-6methyl-5-nitro-1,4-dihydroquinoxaline-2,3-dione; 5,7-dimethyl-6-nitro- 1,4-dihydroquinoxaline-2,3-dione; 6,7-diethyl-5-nitro-1,4-dihydroquinoxaline-2,3-dione; 7-chloro-6-methyl-5-nitro-1,4-dihydroquinoxaline-2,3-dione; 7-bromo-methyl-5-nitro-1,4-dihydroquinoxaline-2,3-dione; 6-fluoro-7-methyl-5-nitro-1,4-dihydroquinoxaline-2,3-dione; 6-chloro-7-methyl-5-nitro-1,4-dihydroquinoxaline-2,3-dione; 6,7-dimethoxy-5-nitro-1,4-dihydroquinoxaline-2,3-dione; 6azido-5,7-difluoro-1,4-dihydroquinoxaline-2,3-dione; 6azido-5,7-dichloro-1,4-dihydroquinoxaline-2,3-dione; 5-azido-6,7-dichloro-1,4-dihydroquinoxaline-2,3-dione; 6,7-dimethyl-5-trifluoromethyl-1,4-dihydroquinoxaline-2,3-dione; 5,7-dimethyl-1,4-dihydroquinoxaline-2,3-dione; 7-methyl-5-trifluoromethyl-1,4-dihydroquinoxaline-2,3-dione; 6,7-diethyl-5-trifluoromethyl-1,4-dihydroquinoxaline-2,3-dione; 5,7-diethyl-6-trifluoromethyl-1,4-dihydroquinoxaline-2,3-dione; 6-bromo-7-methyl-5-nitro-1,4-dihydroquinoxaline-2,3-dione; 7-iodo-6-methyl-5-nitro-1,4-dihydroquinoxaline-2,3-dione; 6-iodo-7-methyl-5-nitro-1,4-dihydroquinoxaline-2,3-dione; 7-fluoro-6-methoxy-5-nitro-1,4-dihydroquinoxaline-2,3-dione; 7-chloro-6-methoxy-5-nitro-1,4-dihydroquinoxaline-2,3-dione; 6-azido-7-fluoro-5-nitro-1,4-dihydroquinoxaline-2,3-dione; 7-methyl-5,6-dinitro-1,4-dihydroquinoxaline-2,3-dione; 6-methyl-5,7-dinitro-1,4-dihydroquinoxaline-2,3-dione; 6,7-dichloro-5-cyano-1,4-dihydroquinoxaline-2,3-dione; 6,7-difluoro-5-cyano-1,4-dihydroquinoxaline-2,3-dione; 1,4-dihydrobenzo-[g]quinoxaline-2,3-dione; 1,4-dihydro-5-nitrobenzo[g]quinoxaline-2,3-dione; 1,4-dihydro-5-nitrocyclopento[g]quinoxaline-2,3-dione; 1,4-dihydro-5-nitrocyclohexo[g]quinoxaline-2,3-dione; 1,4-dihydro-5-nitropyrrolo[2,3-g]quinoxaline-2,3-dione; 1,4-dihydro-5-nitropyrrolo[3,2-g]quinoxaline-2,3-dione; 5,6,7,8-tetrafluoro-1,4-dihydroquinoxaline-2,3-dione; 5-chloro-7-fluoro-1,4-dihydroquinoxaline-2,3-dione; 5-bromo-7-fluoro-1,4-dihydroquinoxaline-2,3-dione; 4-carboxymethyl-5-chloro-6,7-difluoro-1,4-dihydroquinoxaline-2,3-dione; 4-carboxymethyl-5-bromo-6,7-difluoro-1,4-dihydroquinoxaline-2,3-dione; 4-carboxymethyl-5,6,7,8-tetrafluoro-1,4-dihydroquinoxaline-2,3-dione; 4-carboxymethyl-5-chloro-7-fluoro-1,4-dihydroquinoxaline-2,3-dione; 4-carboxymethyl-5-bromo-7-fluoro-1,4-dihydroquinoxaline-2,3-dione; 7-fluoro-6-nitro-5-trifluoromethyl-1,4-dihydroquinoxaline-2,3-dione; 6-amino-7-fluoro-5-trifluoromethyl-1,4-dihydroquinoxaline-2,3-dione; 7-fluoro-5-trifluoromethyl-1,4-dihydroquinoxaline-2,3-dione; 6,7,8-trifluoro-5-nitro-1,4-dihydroquinoxaline-2,3-dione; 6,7,8-trifluoro-5-chloro-1,4-dihydroquinoxaline-2,3-dione; 6,7,8-trifluoro-5-bromo-1,4-dihydroquinoxaline-2,3-dione; 6,7,8-trifluoro-5-iodo-1,4-dihydroquinoxaline-2,3-dione; 6,7,8-trifluoro-5-trifluoromethyl-1,4-dihydroquinoxaline-2,3-dione; 5,6,7-trifluoro-1,4-dihydroquinoxaline-2,3-dione; 6-chloro-5,7-difluoro-1,4-dihydroquinoxaline-2,3-dione; 7-chloro-6,8-difluoro-5-nitro-1,4-dihydroquinoxaline-2,3-dione; 7-chloro-6,8-difluoro-5-trifluoromethyl-1,4-dihydroquinoxaline-2,3-dione; 7-chloro-5,6-difluoro-1,4-dihydroquinoxaline-2,3-dione; 6chloro-7,8-difluoro-5-nitro-1,4-dihydroquinoxaline-2,3-dione; 6-chloro-7,8-difluoro-5-trifluoromethyl-1,4-dihydroquinoxaline-2,3-dione; 6,7-dichloro-8-fluoro-5-nitro-1,4-dihydroquinoxaline-2,3-dione; 6,7-dichloro-8-fluoro-5-trifluoromethyl-1,4-dihydroquinoxaline-2,3-dione; 5,7-bis(trifluoromethyl)-1,4-dihydroquinoxaline-2,3-dione; 7-trifluoromethyl-5-nitro-1,4-dihydroquinoxaline-2,3-dione; 7-chloro-5-nitro-1,4-dihydroquinoxaline-2,3-dione; 7-fluoro-5-nitro-1,4-dihydroquinoxaline-2,3-dione; 6-fluoro-5,7-bis(trifluoromethyl)-1,4-dihydroquinoxaline-2,3-dione; 6-chloro-5,7-bis(trifluoromethyl)-1,4-dihydroquinoxaline-2,3-dione; 6-nitro-5,7-bis(trifluoromethyl)-1,4-dihydroquinoxaline-2,3-dione; 6-bromo-5,7-bis(trifluoromethyl)-1,4-dihydroquinoxaline-2,3-dione; 6-iodo-5,7-bis(trifluoromethyl)-1,4-dihydroquinoxaline-2,3-dione; 6,7-bis(trifluoromethyl)-1,4-dihydroquinoxaline-2,3-dione; 5-nitro-6,7-bis(trifluoromethyl)-1,4-dihydroquinoxaline-2,3-dione; 5-chloro-6,7-bis(trifluoromethyl)-1,4-dihydroquinoxaline-2,3-dione; 5-fluoro-6,7-bis(trifluoromethyl)-1,4-dihydroquinoxaline-2,3-dione; 5-bromo-6,7-bis(trifluoromethyl)-1,4-dihydroquinoxaline-2,3-dione; 5-iodo-6,7-bis(trifluoromethyl)-1,4-dihydroquinoxaline-2,3-dione; 5,6,7-tris(trifluoromethyl)-1,4-dihydroquinoxaline-2,3-dione; 6,7-dichloro-5-trifluoromethyl-1,4-dihydroquinoxaline-2,3-dione; 6,7-difluoro-5-trifluoromethyl- 1,4-dihydroquinoxaline-2,3-dione; 7-chloro-6-bromo-5-nitro-1,4-dihydroquinoxaline-2,3-dione; 7-chloro-6-fluoro-5-nitro-1,4-dihydroquinoxaline-2,3-dione; 6-chloro-7-fluoro-5-nitro-1,4-dihydroquinoxaline-2,3-dione; 7-bromo-6-fluoro-5-nitro-1,4-dihydroquinoxaline-2,3-dione; 6-bromo-7-fluoro-5-nitro-1,4-dihydroquinoxaline-2,3-dione; 7-fluoro-6-iodo-5-nitro-1,4-dihydroquinoxaline-2,3-dione; 6-fluoro-7-iodo-5-nitro-1,4-dihydroquinoxaline-2,3-dione; 7-fluoro-6-trifluoromethyl-5-nitro-1,4-dihydroquinoxaline-2,3-dione; 6-fluoro-7-trifluoromethyl-5-nitro-1,4-dihydroquinoxaline-2,3-dione; 7-chloro-6-trifluoromethyl-5-nitro-1,4-dihydroquinoxaline-2,3-dione; 6-bromo-7-trifluoromethyl-5-nitro-1,4-dihydroquinoxaline-2,3-dione; 7-bromo-6-trifluoromethyl-5-nitro-1,4-dihydroquinoxaline-2,3-dione;

6-iodo-7-trifluoromethyl-5-nitro-1,4-dihydroquinoxaline-2,3-dione; 7-iodo-6-trifluoromethyl-5-nitro-1,4-dihydroquinoxaline-2,3-dione; 6-fluoro-5,7-dinitro-1,4-dihydroquinoxaline-2,3-dione; 7-chloro-5,6-dinitro-1,4-dihydroquinoxaline-2,3-dione; 6-chloro-5,7-dinitro-1,4-dihydroquinoxaline-2,3-dione; 7-bromo-5,6-dinitro-1,4-dihydroquinoxaline-2,3-dione; 6-bromo-5,7-dinitro-1,4-dihydroquinoxaline-2,3-dione; 7-iodo-5,6-dinitro-1,4-dihydroquinoxaline-2,3-dione; 6-iodo-5,7-dinitro-1,4-dihydroquinoxaline-2,3-dione; 7-trifluoromethyl-5,6-dinitro-1,4-dihydroquinoxaline-2,3-dione; 6-trifluoromethyl-5,7-dinitro-1,4-dihydroquinoxaline-2,3-dione; 5-amino-7-chloro-6-methyl-1,4-dihydroquinoxaline-2,3-dione; 7-chloro-6-ethyl-5-nitro-1,4-dihydroquinoxaline-2,3-dione; 5-chloro-8-methyl-1,4-dihydroquinoxaline-2,3-dione; 5-chloro-8-methyl-6,7-dinitro-1,4-dihydroquinoxaline-2,3-dione; 6-chloro-7-ethyl-5-nitro-1,4-dihydroquinoxaline-2,3-dione; 6-chloro-7-ethyl-1,4-dihydroquinoxaline-2,3-dione; 6-chloro-7-ethyl-5-nitro-1,4-dihydroquinoxaline-2,3-dione; 7-chloro-6-ethyl-5-nitro-1,4-dihydroquinoxaline-2,3-dione; 6-chloro-7-fluoro-5-nitro-1,4-dihydroquinoxaline-2,3-dione; 7-chloro-6-ethylthio-5-nitro-1,4-dihydroquinoxaline-2,3-dione; 5-hydroxy-6,7-dimethoxy-1,4-dihydroquinoxaline-2,3-dione; 5-acetyloxy-6,7-dimethoxy-1,4-dihydroquinoxaline-2,3-dione; 5-(2-phenylacetyloxy)-6,7-dimethoxy- 1,4-dihydroquinoxaline-2,3-dione; 5,6,7-trihydroxy-1,4-dihydroquinoxaline-2,3-dione; 6,7-dihydroxy-1,4-dihydroquinoxaline-2,3-dione; 6-(n-butoxy)-7-fluoro-5-nitro-1,4-dihydroquinoxaline-2,3-dione; and 7-fluoro-5-nitro-6-(3-phenylpropoxy)-1,4-dihydroquinoxaline-2,3-dione.

The present invention relates in part to the discovery that certain alkyl substituted quinoxaline-2,3-diones have high affinity for the glycine/NMDA receptor and have unexpectedly high in vivo activity as anticonvulsants in maximum electroshock seizure (MES) experiments in mice. Therefore, these compounds are able to cross the blood brain barrier at high levels. 6,7-Dimethyl-5-nitro-1,4-dihydroquinoxaline-2,3-dione (NDMQX) was found to have high affinity for the glycine/NMDA receptor with $K_i$ of 43 nM, which is about 10 times less active than 6,7-dichloro-5-nitro-1,4-dihydroquinoxaline-2,3-dione. NDMQX, however, was found to have unexpectedly high in vivo activity. It has an $ED_{50}$ of 4–5 mg/kg as an anticonvulsant in the MES experiment in mice. In comparison, 6,7-dichloro-5-nitro-1,4-dihydroquinoxaline-2,3-dione has an $ED_{50}$ of 4–5 mg/kg as an anticonvulsant in the MES experiment in mice. Thus, NDMQX appears to be 10 times better in crossing the blood brain barrier than 6,7-dichloro-5-nitro-1,4-dihydroquinoxaline-2,3-dione.

Since the methyl groups in NDMQX could be replaced by other longer alkyl groups, such as, ethyl or propyl, or by arylalkyl groups, such as, benzyl and phenethyl, as well as by longer alkyl chains containing ether groups, such as, methoxyethyl, which are expected to increase the lipophilicity of the molecule and increase the ability to cross the blood brain barrier, the above discovery has led to a new group of quinoxalinediones (QXs) with good in vivo properties. The $R^2$ and $R^3$ groups in the 6 and 7 positions, respectively, can also be incorporated into a ring system, as shown in Formula VIII. It could be a saturated system and contain hetero atoms, or an unsaturated system, such as, 1,4-dihydrobenzo[g]quinoxaline-2,3-dione (IX).

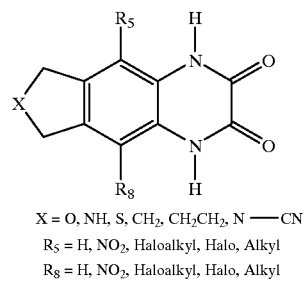

(VIII)

X = O, NH, S, CH₂, CH₂CH₂, N ——CN
R₅ = H, NO₂, Haloalkyl, Halo, Alkyl
R₈ = H, NO₂, Haloalkyl, Halo, Alkyl

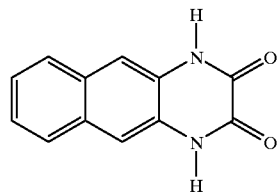

(IX)

Another group of highly interesting compounds are those substituted with both alkyl and halogen substituents, such as, 6-chloro-7-methyl-5-nitro-1,4-dihydroquinoxaline-2,3-dione, 7-fluoro-6-methyl-5-nitro-1,4-dihydroquinoxaline-2,3-dione, and 7-chloro-6-methyl-5-nitro-1,4-dihydroquinoxaline-2,3-dione, which are expected to combine the best of 6,7-dichloro-5-nitro-1,4-dihydroquinoxaline-2,3-dione, 6,7-difluoro-5-nitro-1,4-dihydroquinoxaline-2,3-dione, and 6,7-dimethyl-5-nitro-1,4-dihydroquinoxaline-2,3-dione, having high affinity for the glycine/NMDA receptor and being able to cross the blood brain barrier at high levels. 7-Chloro-6-methyl-5-nitro-1,4-dihydroquinoxaline-2,3-dione (NMCQX) was found to have a high affinity for the glycine/NMDA receptor with a.$K_i$ of 5 nM, which is about as good as 6,7-dichloro-5-nitro-1,4-dihydroquinoxaline-2,3-dione. NMCQX, however, was found to have unexpectedly high in vivo activity. It had an $ED_{50}$ of 1 mg/kg as an anticonvulsant in the MES experiment in mice, which is about 4–5 times better than 6,7-dichloro-5-nitro-1,4-dihydroquinoxaline-2,3-dione ($ED_{50}$= 4–5 mg/kg). 7-Fluoro-6-methyl- 5-nitro-1,4-dihydroquinoxaline-2,3-dione ($K_i$=53 nM, $ED_{50}$=2 mg/kg) and 6-chloro-7-methyl-5-nitro-1,4-dihydroquinoxaline-2,3-dione ($K_i$=27 nM, $ED_{50}$=2 mg/kg) also were found to have a high affinity for the glycine/NMDA receptor and to have unexpectedly high in vivo activity.

The present invention also relates to the discovery that certain fluoro-substituted 1,4-dihydroquinoxaline-2,3-diones have a high affinity for the glycine/NMDA receptor and have unexpectedly high in vivo activity as anticonvulsants in the MES experiment in mice (Table III). Therefore, these compounds are able to cross the blood brain barrier at high levels. 6,7-Difluoro-5-nitro-1,4-dihydroquinoxaline-2,3-dione was found to have a high affinity for the glycine/NMDA receptor with a $K_i$ of 87 nM, which is more than 20 times less active than 6,7-dichloro-5-nitro-1,4-dihydroquinoxaline-2,3-dione (Ki=3.3 nM). 6,7-Difluoro-5-nitro-1,4-dihydroquinoxaline-2,3-dione, however, was found to have surprisingly high in vivo activity. It has an $ED_{50}$ of 0.7–0.8 mg/kg as an anticonvulsant in the MES experiment in mice. In comparison, 6,7-dichloro-5-nitro-1,4-dihydroquinoxaline-2,3-dione has an $ED_{50}$ of 4–5 mg/kg as an anticonvulsant in the MES experiment in mice. This means that 6,7-difluoro-5-nitro-1,4-dihydroquinoxaline-2,3-dione might be about 100 times better in crossing the blood brain barrier than 6,7-dichloro-5-nitro-1,4-dihydroquinoxaline-2,3-dione.

In general, compounds that are used for treating animals should not have a fluorine in the 6- or 8-positions and an electron withdrawing group, such as, nitro, in the 5-position, as such compounds are unstable. As discussed herein, the fluorine group in such compounds is readily displaced by common nucleophiles. Thus, although 6,7-difluoro-5-nitro-1,4-dihydroquinoxaline-2,3-dione has good in vivo activity, it should not be administered to animals, as it may react with biological nucleophiles. 7-Chloro-6,8-difluoro-5-nitro-1,4-dihydroquinoxaline-2,3-dione was found to have high affinity for the glycine/NMDA receptor with $K_i$ of 170 nM, which is about 50 times less active than 6,7-dichloro-5-nitro-1,4-dihydroquinoxaline-2,3-dione. 7-Chloro-6,8-difluoro-5-nitro-1,4-dihydroquinoxaline-2,3-dione also was found to have surprisingly high in vivo activity. It has an $ED_{50}$ of 2–3 mg/kg as an anticonvulsant in the MES experiment in mice. In comparison, 6,7-dichloro-5-nitro-1,4-dihydroquinoxaline-2,3-dione has an $ED_{50}$ of 4–5 mg/kg as an anticonvulsant in the MES experiment in mice. This means that 7-chloro-6,8-difluoro-5-nitro-1,4-dihydroquinoxaline-2,3-dione might be about 100 times better in crossing the blood brain barrier than 6,7-dichloro-5-nitro-1,4-dihydroquinoxaline-2,3-dione.

The compounds disclosed herein are active in treating or preventing neuronal loss, neurodegenerative diseases, and chronic pain and are active as anticonvulsants and in inducing anesthesia without untoward side effects caused by non-selective binding with other receptors, particularly, kainate, AMPA, and quisqualate receptors and the PCP and glutamate receptors associated with the NMDA receptor. In addition, these compounds are effective in treating or preventing the adverse consequences of the hyperactivity of the excitatory amino acids, e.g., those that are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases that may be treated with the disclosed compounds include those selected from the group consisting of Alzheimer's disease, amyotrophic lateral sclerosis, Huntington's disease, and Down's syndrome.

These compounds also find particular utility in the treatment or prevention of neuronal loss associated with multiple strokes that give rise to dementia. After a patient has been diagnosed as suffering from a stroke, the compounds can be administered to ameliorate the immediate ischemia and prevent further neuronal damage that may occur from recurrent strokes.

Moreover, these compounds are able to cross the blood/brain barrier, in contrast to 6-cyano-7-nitro-1,4-dihydroquinoxaline-2,3-dione, 6,7-dinitro-1,4-dihydroquinoxaline-2,3-dione, and other 6,7-disubstituted 1,4-dihydroquinoxaline-2,3-diones that are incapable of crossing the blood/brain barrier after i.p. administration (see Turski, L. et al., *J. Pharm. Exp. Ther.* 260:742–747 (1992)). See also, Sheardown et al., *Eur. J. Pharmacol.* 174:197–204 (1989), who disclose that 5,7-dinitro-1,4-dihydroquinoxaline-2,3-dione, 6,7-dinitro-1,4-dihydroquinoxaline-2,3-dione, and cyano-7-nitro-1,4-dihydroquinoxaline-2,3-dione have poor access to the central nervous system.

For a compound to begin to show in vivo efficacy and, thus, the ability to cross the blood-brain barrier, the compound should exhibit an $ED_{50}$ of less than about 100 mg/kg body weight of the animal. Preferably, the compounds of the present invention exhibit an $ED_{50}$ of less than about 20 mg/kg and, more preferably, less than about 10 mg/kg.

These compounds find particular utility in treating or preventing the adverse neurological consequences of surgery. For example, coronary bypass surgery requires the use of heart-lung machines, which tend to introduce air bubbles into the circulatory system that may lodge in the brain. The presence of such air bubbles robs neuronal tissue of oxygen, resulting in anoxia and ischemia. Pre- or post-surgical administration of the 1,4-dihydroquinoxalines of the present invention will treat or prevent the resulting ischemia. In a preferred embodiment, the compounds are administered to patients undergoing cardiopulmonary bypass surgery or carotid endarterectomy surgery.

These compounds also find utility in treating or preventing pain, e.g., chronic pain. Such chronic pain can be the result of surgery, trauma, headache, arthritis, or other degenerative disease. The compounds of the present invention find particular utility in the treatment of phantom pain that results from amputation of an extremity. In addition to treatment of pain, the compounds of the invention are also useful in inducing anesthesia, either general or local anesthesia, as, for example, during surgery.

The compounds of the present invention can be tested for potential glycine antagonist activity by observing the inhibition of binding of 1 $\mu$M glycine-stimulated [$^3$H]-MK-801 in rat or guinea pig brain membrane homogenates. The more potent the glycine antagonist, the less [$^3$H]-MK-801 can bind since the [$^3$H]-MK801 binding site (PCP receptor) is accessible only upon the opening of the ion channel by glutamate and glycine (Fletcher, E. L., et al., in *Glyine Neurotransmission*, Otterson, P., et al. (eds.), John Wiley and Sons (1990); Johnson, J. W., et al., *Nature* 325:529 (1987)).

The binding affinities of quinoxaline-2,3-diones at NMDA receptor glycine sites also were estimated by electrophysiological assays with either cloned rat NMDA receptors expressed in Xenopus oocytes, or non-NMDA receptors expressed in oocytes by whole rat brain poly(A)$^+$ RNA. $K_i$ values were estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors $K_i$s were approximated by averaging values at three subtype combinations (NR1A/NR2A, NR1A/NR2B, and NR1A/NR2C). See U.S. application Ser. No. 08/148,259, entitled Glycine Receptor Antagonists and the Use Thereof, supra.

Preferably, the compounds of the invention exhibit a binding affinity to the glycine binding site of $K_i$=about 10 $\mu$M or less, more preferably, 1 $\mu$M or less, and more preferably, 500 nM or less, and more preferably, 100 $\mu$M or less, and most preferably, about 10 nM or less. Also preferable are compounds that exhibit binding at the kainate and AMPA sites of not less than $K_i$=1 $\mu$M and, more preferably, not less than 10 $\mu$M.

The novel glycine antagonists can be tested for in vivo activity after intraperitoneal injection using a number of anticonvulsant tests in mice (audiogenic seizure model in DBA-2 mice, pentylenetetrazol-induced seizures in mice, NMDA-induced death in mice, and MES in mice). Preferred compounds exhibit ataxia side effects in the rotorod ataxia test at dosage levels of greater than about 100 mg/kg, more preferably, greater than about 200 mg/kg.

The compounds can also be tested in drug discrimination tests in rats trained to discriminate PCP from saline. It is expected that most of the compounds will not generalize to PCP at any dose. In addition, it is also expected that none of the compounds will produce a behavioral excitation in locomotor activity tests in the mouse. It is expected that such results will suggest that the glycine, AMPA, kainate, and quisqualate antagonists of the present invention do not show the PCP-like behavioral side effects that are common to NMDA channel blockers such as MK-801 and PCP or to competitive NMDA antagonists such as CGS19755.

The glycine and excitatory amino acid antagonists are also expected to show potent activity in vivo after intraperitoneal injection suggesting that these compounds can penetrate the blood/brain barrier.

Azido-substituted 1,4-dihydroquinoxaline-2,3-diones can be employed to photoaffinity-label the glycine receptor. Unexpectedly, it has been discovered that 6-azido-1,4-dihydroquinoxaline-2,3-dione quite favorably binds to the glycine binding site, as compared to the corresponding 6-$CF_3$, 6-$NO_2$, 6-F, 6-CN, 6-$NH_2$, and unsubstituted derivatives (table I):

TABLE I

| $R^2$ | $K_i$ (nM) |
|---|---|
| $N_3$ | 210 |
| $CF_3$ | 360 |
| $NO_2$ | 1395 |
| H | 2466 |
| F | 2880 |
| CN | 4889 |
| $NH_2$ | inactive |

The compounds of the present invention can be prepared as follows. As shown in Scheme I, the isomeric 6-halo-7-methyl-5-nitro-1,4-dihydroquinoxaline-2,3-dione and 7-halo-6-methyl-5-nitro- 1,4-dihydroquinoxaline-2,3-dione can be prepared from a 3-halo-4-methylaniline by protection of the amino group with, for example, trifluoroacetic acid anhydride, followed by ortho nitration. Removal of the amino-protecting group and reduction of the ortho-nitro group gives the 3-halo-4-methyl-1,2-phenylenediamine. This 1,2-phenylenediamine can then be condensed with oxalic acid to give the 7-halo-6-methyl-1,4-dihydroquinoxaline-2,3-dione. Nitration leads to a mixture of the two isomeric compounds.

Scheme I

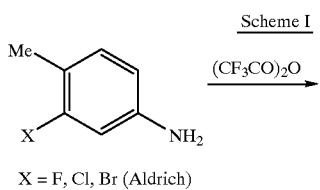

X = F, Cl, Br (Aldrich)

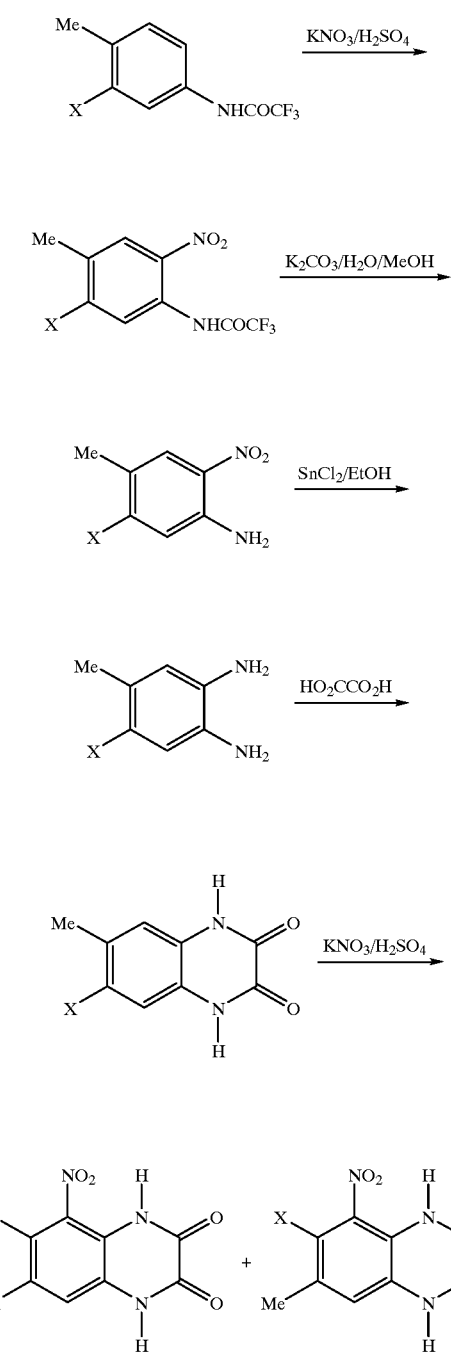

Alternatively, the intermediate trifluoroacetyl 2-amino-5-halo-4-methylanilide can be further treated with trifluoroacetic acid anhydride followed by nitration to give two isomeric nitro compounds, which may be separated. Removal of the protecting groups, condensation with oxalic acid, and subsequent nitration gives the isomerically pure 7-halo-6-methyl-5-nitro-1,4-dihydroquinoxaline-2,3-dione and 6-halo-7-methyl-5-nitro-1,4-dihydroquinoxaline-2,3-dione. (See Scheme II).

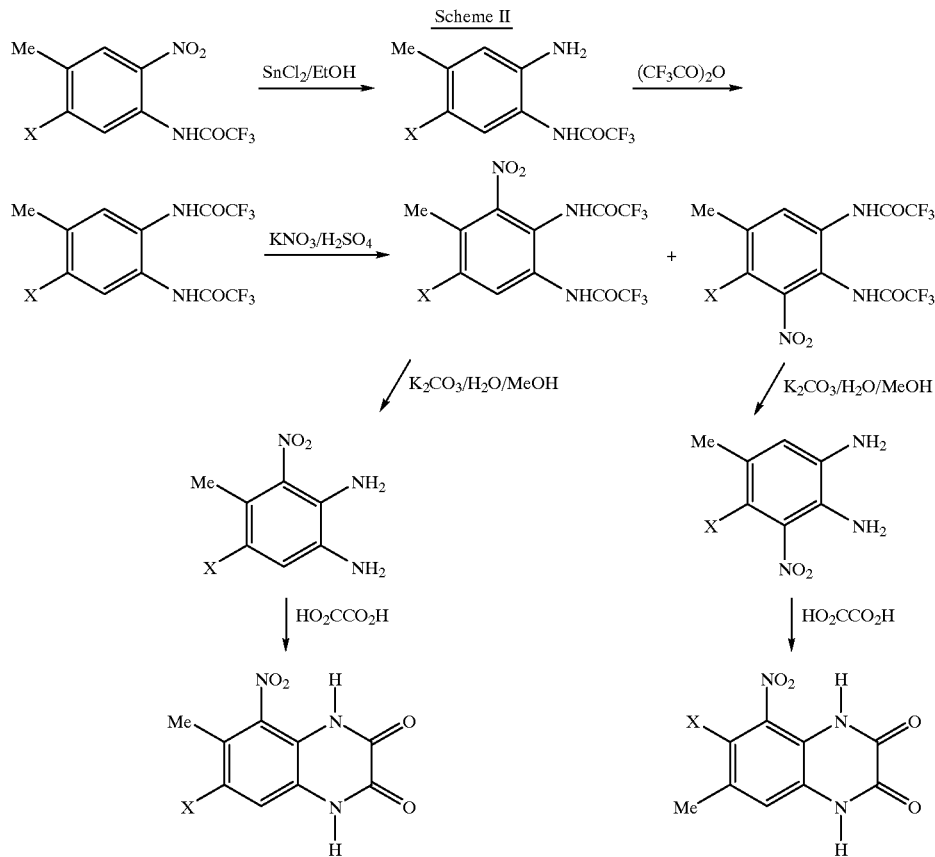

Scheme II

A second approach was based on the discovery that nitration of 3,4-dihydroquinoxaline-2(1H)-one resulted exclusively in the product with the nitro group in the 5-position. For example, treatment of 2,5-difluoro-4-nitrotoluene with sodium glycinate gave the substituted aniline. The nitro group was reduced by $SnCl_2$ and the product spontaneously cyclized to give the 3,4-dihydroquinoxaline-2(1H)-one. It was nitrated by fuming $HNO_3$ in trifluoroacetic acid, resulting in both nitration and oxidation of the compound to give 7-fluoro-6-methyl-5-nitro-1,4-dihydroquinoxaline-2,3-dione in a single step (Scheme III). The F-H coupling constants measured from the $^1H$ NMR spectrum confirmed that the fluoro was meta to the nitro group.

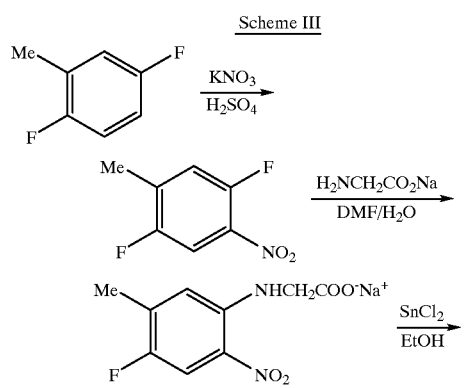

Scheme III

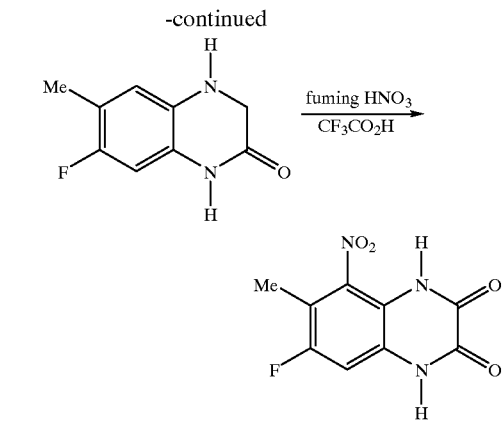

-continued

Similarly, treatment of 1-bromo-2,4-difluoro-5-nitrobenzene with sodium glycinate gave a mixture of the substituted anilines. The nitro group was reduced by $SnCl_2$ and the product spontaneously cyclized to give the 3,4-dihydroquinoxaline-2(1H)-one. It was nitrated by $HNO_3$ in trifluoroacetic acid, resulting in both nitration and oxidation of the compound to give 7-bromo-6-fluoro-5-nitro-1,4-dihydroquinoxaline-2,3-dione in a single step (Scheme IV). The F-H coupling constants measured from the $^1H$ NMR spectrum confirmed that the fluoro was ortho to the nitro group. Alternatively, 1-bromo-2,5-difluoro-4-nitrobenzene can be reduced, cyclized, and oxidized with $HNO_3$ to give 6-bromo-7-fluoro-5-nitro-1,4-dihydroquinoxaline-2,3-dione.

Scheme IV

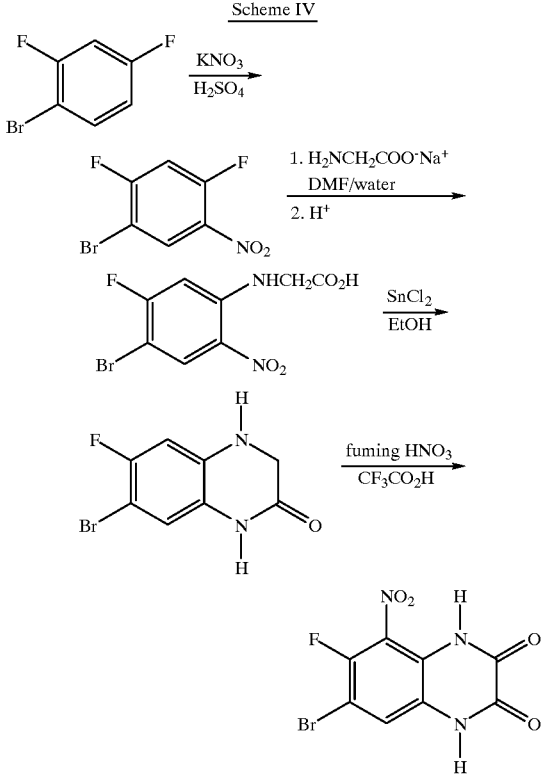

Thus, the invention also relates to a method for the preparation of a 1,4-dihydroquinoxaline-2,3-dione having the Formula:

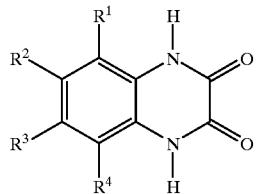

or a tautomer thereof;
wherein
R$^1$ is nitro;
R$^2$ is haloalkyl, halo, cyano, alkyl, or alkoxy;
R$^3$ is haloalkyl, halo, cyano, alkyl, or alkoxy; and
R$^4$ is hydrogen;
comprising reaction of a compound having the Formula:

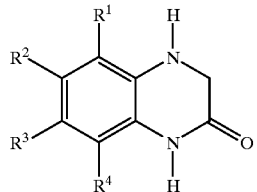

or a tautomer thereof;
wherein
R$^1$ is hydrogen;
R$^2$ is haloalkyl, halo, cyano, alkyl, or alkoxy;

R$^3$ is haloalkyl, halo, cyano, alkyl, or alkoxy; and

R$^4$ is hydrogen; with fuming nitric acid; and isolating the 1,4-dihydroquinoxaline-2,3-dione so produced. A preferred solvent that can be used for this reaction is trifluoroacetic acid. The reaction is carried out at room temperature until there is an absence of starting material (e.g., overnight).

6,7-Dimethyl-5-nitro-1,4-dihydroquinoxaline-2,3-dione (NDMQX) can be prepared by condensation of 4,5-dimethyl-1,2-phenylenediamine with oxalic acid followed by nitration (HNO$_3$/H$_2$SO$_4$ or KNO$_3$/CF$_3$CO$_2$H). It was found that nitration in trifluoroacetic acid gave a purer product than in sulfuric acid. (See Scheme V).

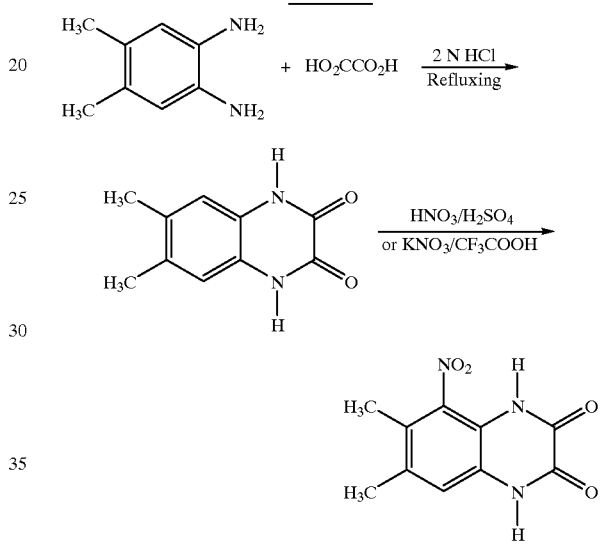

Using a procedure similar to that set forth in Scheme I, compounds having fused carbocycloalkyl, heteroalkyl, aromatic, and heteroaromatic groups fused to the 6- and 7-positions of the quinoxaline ring can be prepared. (See Scheme VI).

6,7-Dimethoxy-1,4-dihydroquinoxaline-2,3-dione was prepared from 1,2-dimethoxybenzene. Nitration of 1,2-dimethoxybenzene gave 1,2-dimethoxy-4,5-dinitrobenzene, which was reduced to 1,2-diamino-4,5-dimethoxybenzene. Condensation of the diamine with oxalic acid gave 6,7-dimethoxy-1,4-dihydroquinoxaline-2,3-dione.

Scheme VI

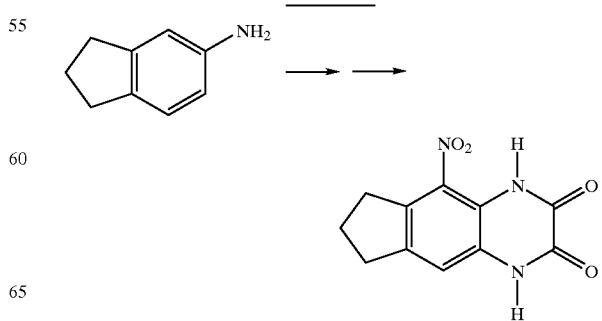

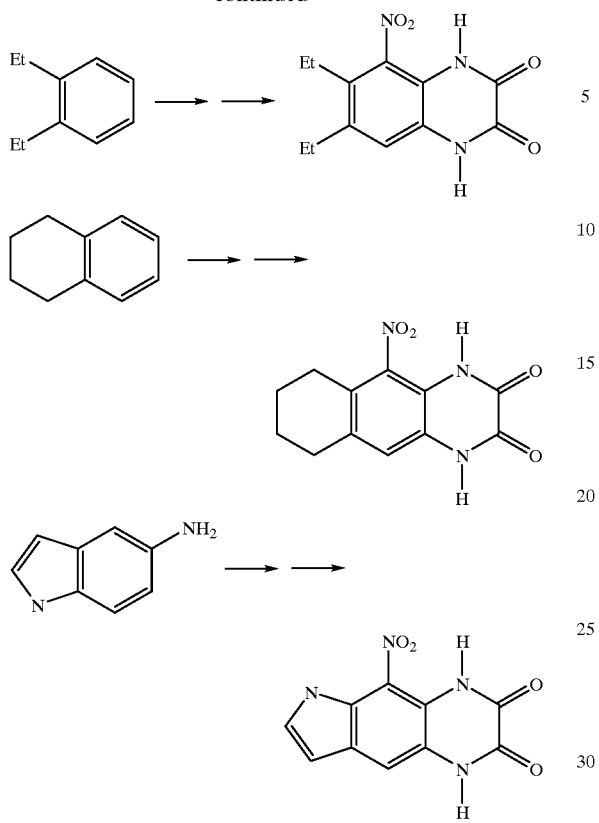

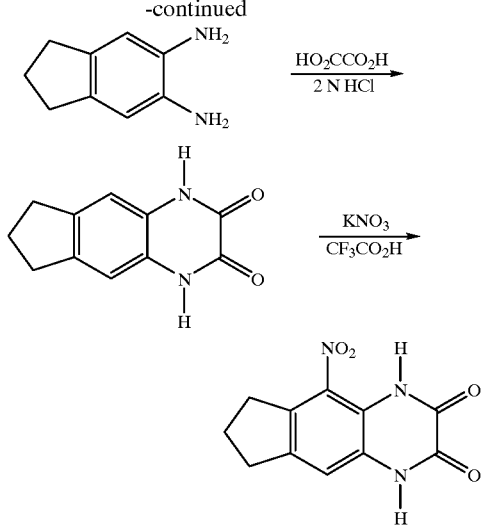

5-Nirocyclopento[g]-1,4-dihydroquinoxaline-2,3-dione was prepared from 5-aminoindan as show in Scheme VII. Nitration of 5-acetamidoindan gave a mixture of nitro products, which was separated by chromatography to give 5-acetamido-6-nitroindan in about 20% yield. Deprotection followed by reduction and condensation of the resulting diamine with oxalic acid gave cyclopento[g]-1,4-dihydroquinoxaline-2,3-dione in good yield. Nitration under conditions of $KNO_3/H_2SO_4$ or $HNO_3/H_2SO_4$ gave complicated products. However, nitration under the mild condition of $KNO_3/CF_3CO_2H$ gave 5-nitro-cyclopento[g]-1,4-dihydroquinoxaline-2,3-dione as the only product.

Azidosubstituted quinoxaline-2,3-diones were prepared by diazotization of amino substituted 1,4-dihydroquinoxaline-2,3-diones followed by treatment with sodium azide:

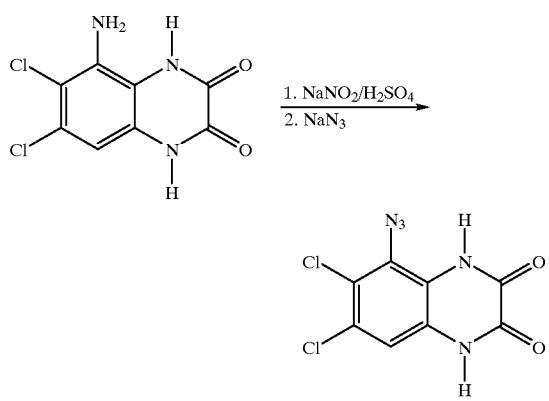

The structure-activity relationships of a number of alkyl, azido, fluoro, alkoxy, and cyano-substituted 1,4-dihydroquinoxaline-2,3-diones are set forth in Table II.

TABLE II

Structure and Activity of Alkyl, Azido, Fluoro, Alkoxy, and Cyano-Substituted 1,4-Dihydroquinoxaline-2,3-diones

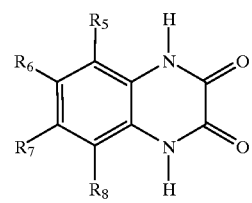

| $R_5$ | $R_6$ | $R_7$ | $R_8$ | $K_i(nM)^a$ |
|---|---|---|---|---|
| $NO_2$ | Me | Me | H | 43 |
| $NO_2$ | Me | F | H | 53 |
| $NO_2$ | Me | Br | H | 40[b] |

Scheme VII

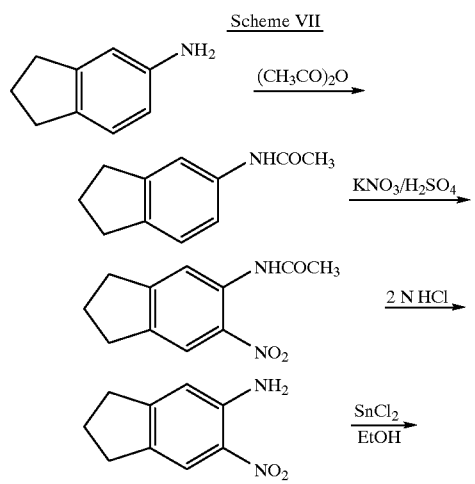

TABLE II-continued

Structure and Activity of Alkyl, Azido,
Fluoro, Alkoxy, and Cyano-Substituted
1,4-Dihydroquinoxaline-2,3-diones

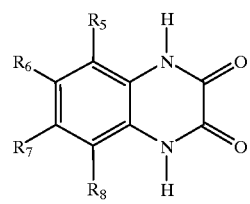

| $R_5$ | $R_6$ | $R_7$ | $R_8$ | $K_i(nM)^a$ |
|---|---|---|---|---|
| $NO_2$ | Cl | Me | H | 27 |
| $NO_2$ | Me | Cl | H | 5 |
| $NO_2$ | OMe | F | H | 320 |
| $NO_2$ | OEt | F | H | 1000 |
| $NO_2$ | $N_3$ | F | H | 280 |
| $NO_2$ | OMe | Cl | H | 450[b] |
| $NO_2$ | Et | Cl | H | 200[b] |
| $NO_2$ | Cl | Et | H | 40[b] |
| $NO_2$ | OBu-n | F | H | 6500[b] |
| $NO_2$ | $O(CH_2)_3Ph$ | F | H | 6700[b] |
| $NO_2$ | SEt | Cl | H | 500 |
| $NH_2$ | Me | Cl | H | 500[b] |
| H | OMe | OMe | H | PA[b,c] |
| H | Et | Et | H | 800[b] |
| H | Cl | Et | H | 730[b] |
| CN | Cl | $NO_2$ | H | 50 |
| CN | Cl | Cl | H | 15[d] |
| $NO_2$ | H | Me | H | 1200 |
| Me | H | Me | H | 1700 |
| Et | H | Br | H | 900 |
| H | Me | Me | H | 980 |
| Me | H | H | H | PA[b,c] |
| H | Me | H | H | 9000[b] |
| H | $CH_2CH_2CH_2$ | | H | 6300 |
| $NO_2$ | $CH_2CH_2CH_2$ | | H | 800 |
| H | CH=CHCH=CH | | H | 11000 |
| $N_3$ | Cl | Cl | H | 71 |
| Cl | $N_3$ | Cl | H | 536 |
| Cl | H | H | Me | PA[b,c] |
| Cl | $NO_2$ | $NO_2$ | Me | 3800[b] |
| H | $N_3$ | H | H | 910[b] |

[a]From electrophysiology using Xenopus oocytes unless otherwise noted.
[b]From binding assays.
[c]PA = partially active.
[d]Contains ~4% of the compound in which $R_5$ = CN, $R_6$ = Cl, $R_7$ = $NH_2$, $R_8$ = H.

Table III sets forth the in vivo activities of a number of fluoro-substituted 1,4-dihydroquinoxaline-2,3-diones. As can be seen, these compounds exhibit good anticonvulsant activity in vivo.

Table IV summarizes results of eight 1,4-dihydroquinoxaline-2,3-diones tested i.v. as anticonvulsants in MES experiments in mice. Most of the compounds tested have very fast peaks of action, especially the fluoro substituted compounds. The protecting effect of fluoro substituted compounds against MES decreased very quickly. After 60 min., no more protection was observed for 6,7-difluoro-5-nitro-1,4-dihydroquinoxaline-2,3-dione and 5,6,7-trifluoro-1,4-dihydroquinoxaline-2,3-dione. Chloro substituted compounds also have a fast peak of action, but the protecting effect lasts much longer than fluoro substituted compounds. Trifluoromethyl substituted compounds have relatively slow peaks of action, and the protecting effect lasts longer than fluoro substituted compounds. This different pattern of action of 1,4-dihydroquinoxaline-2,3-diones could be used to apply individual compounds for different types of therapeutic treatment. The present invention is also directed to this discovery.

TABLE III

In vivo Activity of Fluoro substituted
1,4-Dihydroquinoxaline-2,3-diones

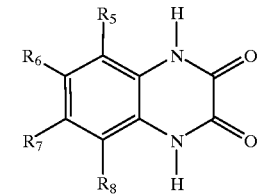

| $R_5$ | $R_6$ | $R_7$ | $R_8$ | $K_i$ (nM) | $ED_{50}$ (DBA-2)[a] mg/kg | $ED_{50}$ (MES)[c] mg/kg |
|---|---|---|---|---|---|---|
| F | F | F | F | 2186 | 9 | 20[a] |
| $NO_2$ | F | Cl | F | 170 | ND[b] | 2–3 |
| $NO_2$ | Br | F | H | 43 | ND | 3.5 |
| $NO_2$ | F | Cl | H | 70 | ND | 0.9 |
| $NO_2$ | Cl | F | H | 180 | ND | 4–5 |
| F | F | F | H | 2966 | ND | 4–5 |
| $NO_2$(H) | Cl | F | H($NO_2$) | 18 | ND | 0.5–0.7 |
| Br | F | F | H | 2300 | 30 | ND |
| F | Cl | F | H | 1000 | ND | 10 |
| H | F | F | H | 8200 | ND | 15 |
| $NO_2$ | Me | F | H | 53 | ND | 2 |
| $NO_2$ | OMe | F | H | 320 | ND | 7.5 |
| $NO_2$ | $N_3$ | F | H | 280 | ND | 7.5 |
| $NO_2$ | F | F | H | 87 | ND | 0.7–0.8 |

[a]i.p. injection.
[b]ND, not determined.
[c]i.v. injection unless otherwise noted.

TABLE IV

1,4-Dihydroquinoxaline-2,3-diones Tested i.v. for Protection Against MES

| $R_5$ | $R_6$ | $R_7$ | $R_8$ | $K_i$(nM) | IV peak of action (min) | $ED_{50}$ (MES) mg/kg | $ED_{100}$ (MES) mg/kg | % protection after 60 min. |
|---|---|---|---|---|---|---|---|---|
| $NO_2$ | Cl | Cl | H | 3.3 | 5 | 4–5 | 7–10 | 55 (10 mg/kg) |
| $NO_2$ | F | Cl | F | 170 | 2–5 | 2–3 | 5 | 50 (5 mg/kg) |
| F | F | F | H | 2966 | 2 | 4–5 | 15–20 | 0 (10 mg/kg) |
| $NO_2$(H) | Cl | F | H($NO_2$) | 18 | 5 | 0.5–0.7 | 4 | 14 (10 mg/kg) |
| $CF_3$ | H | Cl | H | 395 | 30 | 10 | 30 | 87 (30 mg/kg) |
| Cl | H | $CF_3$ | H | 320 | 15 | 10 | 20–25 | 62 (20 mg/kg) |
| $NO_2$ | H | $CF_3$ | H | 95 | 30 | 17 | 40 | 62 (40 mg/kg) |
| $NO_2$ | F | F | H | 87 | 1 | 0.7–0.8 | 2.5 | 0 (2.5 mg/kg) |

It was discovered during the formulation and stability experiments with nitro and fluoro substituted 1,4-dihydroquinoxaline-2,3-diones that some of these compounds are unstable toward nucleophiles such as thiol (SH) in 2-mercaptoethanol and amino and guanidine in arginine, and replacement of the F by thiol or amino groups was observed. It was recognized that these observations could be utilized to prepare a group of 1,4-dihydroquinoxaline-2,3-diones that otherwise could not be prepared easily. Nucleophilic substitution of the fluoro ortho to the nitro group in 6,7-difluoro-5-nitroquinoxaline-2,3-dione (1) with different nucleophiles was accomplished as shown in eq 11–15. The reaction was generally followed by $^1$H NMR and/or $^{19}$F NMR spectroscopy. Replacement of the fluoro ortho to the nitro group by a nucleophile converts the aromatic H from a doublet of doublets to a doublet. The F—H coupling constants are around 11.5 Hz, which confirms that the remaining F is ortho to the H. The reaction between 1 and sodium azide is almost instantaneous after the two are mixed in DMSO. Measurement of $^1$H NMR spectrum immediately after the sample was mixed showed a doublet at 7.1 ppm for the aromatic H and no starting material was observed.

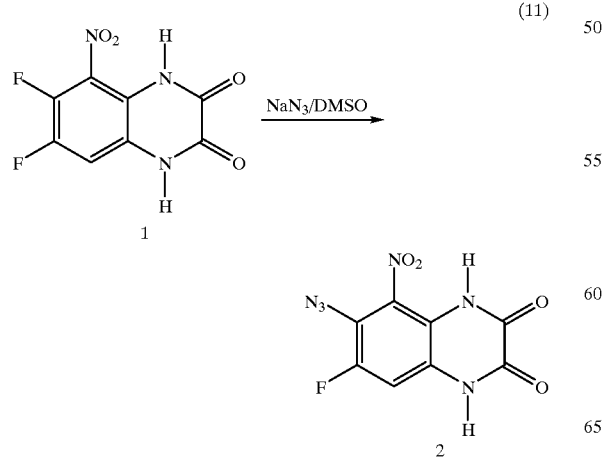
(11)

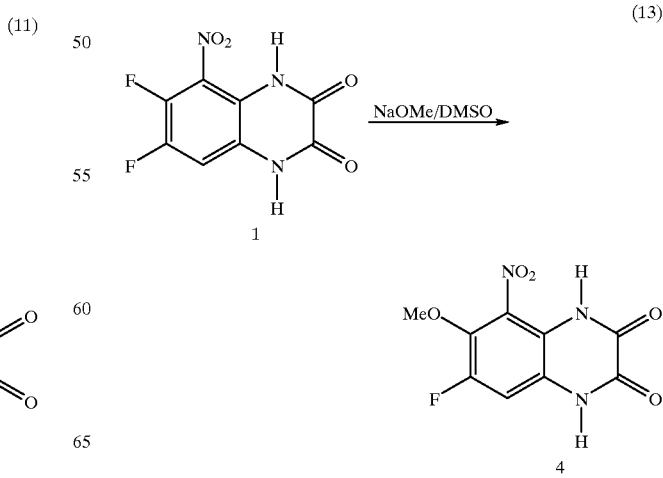
(12)

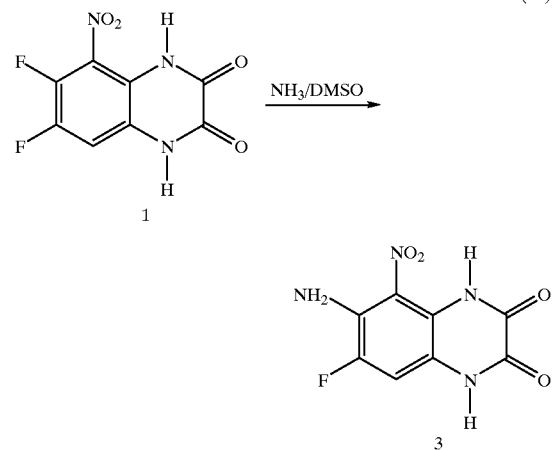
(13)

-continued

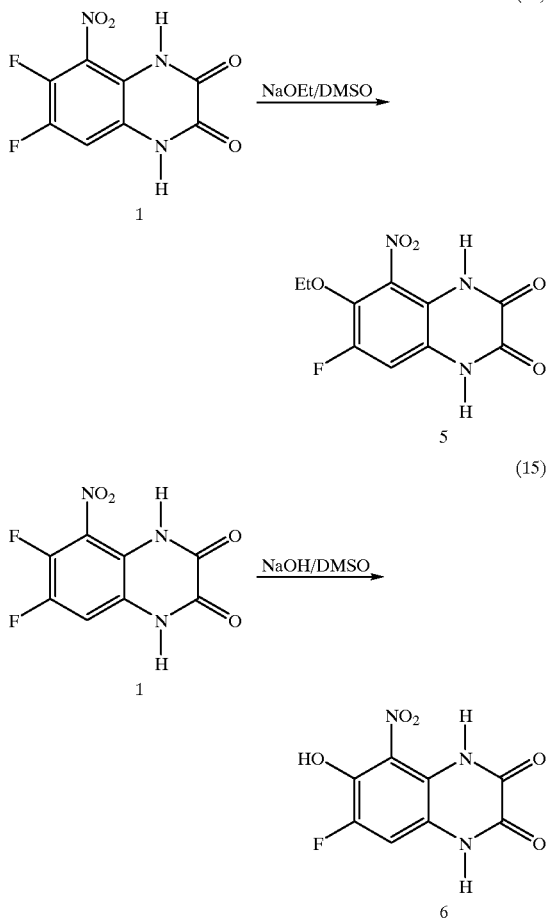

Similarly, the reaction of 7-chloro-6-fluoro-5-nitro-1,4-dihydroquinoxaline-2,3-dione with sodium methoxide gave 7-chloro-6-methoxy-5-nitroquinoxaline-2,3-dione, and with ethanethiol gave 7-chloro-6-ethylthio-5-nitroquinoxaline-2,3-dione.

Thus, the invention also relates to a method for the preparation of compounds having the Formula:

or a tautomer thereof;

wherein $R^1$ is nitro, cyano, $CF_3$, carboxy, or alkanoyl;

$R^2$ is alkoxy, aralkoxy, hydroxy, mercaptoalkyl, azido, or $NR^5R^6$, wherein $R^5$ and $R^6$ are independently hydrogen, alkyl, or aryl groups;

$R^3$ is halo, haloalkyl, nitro, alkyl, alkoxy, azido, or cyano; and $R^4$ is hydrogen;

comprising reaction of a compound having the Formula:

or a tautomer thereof;

wherein $R^1$ is nitro, cyano, $CF_3$, carboxy, or alkanoyl;

$R^2$ is fluoro;

$R^3$ is halo, haloalkyl, nitro, alkyl, alkoxy, azido, or cyano; and $R^4$ is hydrogen;

with an alkoxide, aryl alkoxide, hydroxide, an alkyl mercaptide, azide, or $HNR^5R^6$, respectively, in an inert solvent, and isolating the compound so produced. Examples of such inert solvents include dipolar aprotic solvents, such as DMF and DMSO. Where the nucleophile is an alkoxy group, the solvent can be the corresponding alcohol. The reaction is carried out between room temperature and 120° C., and the progress monitored by NMR spectroscopy.

Electron withdrawing groups such as cyano, $CF_3$, carboxy, and alkanoyl in the 5-position are expected to behave similarly to nitro. Any group can be present in the 7- and 8-positions for the reaction to proceed.

Examples of compounds that can be produced according to this method include 6-azido-7-fluoro-5-nitro-1,4-dihydroquinoxaline-2,3-dione; 6-amino-7-fluoro-5-nitro-1,4-dihydroquinoxaline-2,3-dione; 7-fluoro-6-methoxy-5-nitro-1,4-dihydroquinoxaline-2,3-dione; 7-fluoro-6-ethoxy-5-nitro-1,4-dihydroquinoxaline-2,3-dione; 7-fluoro-6-hydroxy-5-nitro-1,4-dihydroquinoxaline-2,3-dione; 7-chloro-6-methoxy-5-nitroquinoxaline-2,3-dione; and 7-chloro-6-ethylthio-5-nitroquinoxaline-2,3-dione.

Thus, the present invention is directed to compounds having high binding to the glycine receptor and low binding to the kainate and AMPA sites. The glycine antagonist potency in vitro can be determined using a 1 μM glycine-stimulated [$^3$H]-MK801 binding assay. This assay takes advantage of the dependence of the binding of [H]-MK801 to the PCP receptor inside the pore of the NMDA channel on the presence of both glutamate and glycine. In the absence of glycine, but in the presence of glutamate, [$^3$H]-MK801 cannot bind effectively to the PCP receptor because the NMDA channel remains closed and access of [$^3$H]-MK801 to the PCP receptor inside the closed channel pore is severely restricted.

The assay is conducted using rat brain membrane homogenates that are enriched in NMDA receptors. The membranes are prepared as follows. Frozen rat brains (obtained from Pel-Freez, Rogers, Ark.) are homogenized in 15 volumes (w/v) of ice cold 0.32 M sucrose. The homogenate is spun at 1,000×g for ten minutes. The supernatant is collected and spun for 20 minutes at 44,000×g. The pellet is suspended in 15 volumes of water (relative to original brain weight). The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 mM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4, and the protein concentration is determined with a standard dye-binding protein assay (Bio-Rad, Richmond, Calif.). The suspension is stored at −80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/mL. For binding assays, 0.8 mL of membranes are pipetted into polypropylene tubes followed by 0.033 mL of 15.1 $\mu$M 5,7-dichlorokynurenic acid (DCK), 0.033 ml of 30.3 $\mu$M glycine in buffer (or buffer alone), 0.033 mL of 303 $\mu$M glutamate in buffer (or for controls, 0.1 mL 1 mM PCP instead of DCK/gly/glu), 0.033 mL glycine antagonist in buffer (or buffer alone) and 0.1 mL buffer containing 200,000 cpm [$^3$H]-MK801. Nonspecific binding is defined as the difference in binding that occurs in the absence or presence of PCP (final concentration: 100 $\mu$M). To determine the effect of 1 $\mu$M glycine on the binding of [$^3$H]-MK801, bound radioactivity in the presence of 10 $\mu$M glutamate alone (final concentration) is subtracted from the bound radioactivity in the presence of both 10 $\mu$M glutamate and 1 $\mu$M glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK801 binding that is effected by the addition of 1 $\mu$M exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 mL each of ice cold buffer. Filters are transferred to scintillation vials and 5 mL of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 $\mu$M. IC$_{50}$ values are determined for compounds active in inhibiting 1 $\mu$M glycine-stimulated [$^3$H]-MK801 binding by computer-assisted plotting of the inhibition curves and interpolation. When compounds are found to inhibit glycine-stimulated [$^3$H]-MK801 binding, experiments are conducted to determine whether the inhibition of the glycine-stimulated [$^3$H]-MK801 binding is indeed mediated at the glycine binding site of the NMDA receptor. In these experiments, a fixed concentration of antagonist sufficient to produce a >95% inhibition of the 1 $\mu$M glycine-stimulated [$^3$H]-MK801 binding is incubated with the membranes without any additional glycine (above 1 $\mu$M) and in the presence of increasing concentrations of additional glycine (2 $\mu$M to 1 $\mu$M). If the inhibition of [$^3$H]-MK801 binding by the drug in the presence of 1 $\mu$M glycine is fully reversed by adding increasing concentrations of glycine, then the inhibition of [$^3$H]-MK801 binding is mediated by the drug acting as an antagonist at the glycine binding site of the NMDA receptor.

After constructing inhibition dose response curves and determination of glycine reversibility, K$_1$ values for the glycine antagonists are calculated using the Cheng and Prusoff equation employing the experimentally determined IC$_{50}$ values, the known concentration of glycine in the assay (1 $\mu$M) and the known affinity of glycine for the glycine binding site of the NMDA receptor (100 nM).

The same rat brain membrane homogenates used for the 1 $\mu$M glycine-stimulated [$^3$H]-MK801 binding assay are used for the [$^3$H]-AMPA radioligand binding assay. On the day of the assay the frozen membranes (prepared as described above) are thawed and diluted with 30 mM Tris/HCl buffer containing 2.5 mM CaCl$_2$ and 100 mM KSCN, pH 7.4, to yield a final membrane concentration of 1.25 mg/mL membrane protein. For the binding assay, 0.8 mL of membrane homogenate is added to polypropylene tubes followed by 0.033 mL drug and 0.067 mL buffer (or, for controls, by 0.1 mL buffer alone) and 0.1 mL buffer containing 200,000 cpm of [$^3$H]-AMPA. The assay is incubated for 30 minutes on ice. Bound radioactivity is separated from free radioactivity by filtration, over Whatman glass fiber filters (pretreated with 0.3% polyethyleneimine) using a Brandel 48 well cell harvester.

Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 10 nM to 100 $\mu$M.

The same membrane preparation as that used for the [$^3$H]-AMPA binding assay can be used for the [$^3$H]-Kainate radioligand binding assay. On the day of the assay the frozen rat brain membranes are thawed and 5 mM Tris/HCl buffer, pH 7.4, is added to yield a final concentration of 0.5 mg/mL membrane protein. For the binding assay, 0.8 mL of membrane homogenate is added to polypropylene tubes followed by 0.033 mL drug and 0.067 mL buffer (or, for controls, by 0.1 mL buffer alone) and 0.1 mL buffer containing 200,000 cpm of [$^3$H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 $\mu$M.

The anxiolytic activity of any particular compound of the present invention can be determined by use of any of the recognized animal models for anxiety. A preferred model is described-by Jones, B. J. et al., *Br. J. Pharmacol.* 93:985–993 (1988). This model involves administering the compound in question to mice that have a high basal level of anxiety. The test is based on the finding that such mice find it aversive when taken from a dark home environment in a dark testing room and placed in an area that is painted white and brightly lit. The test box has two compartments, one white and brightly illuminated and one black and non-illuminated. The mice have access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters can be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena can be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity can also be measured to allow detection of drug effects specific to social behaviors.

The efficacy of the glycine and excitatory amino acid antagonists to inhibit glutamate neurotoxicity in a rat brain cortex neuron cell culture system can be determined as follows. An excitotoxicity model modified after that developed by Choi (Choi, D. W., *J. Neuroscience* 7:357 (1987)) can be used to test anti-excitotoxic efficacy of the glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (*Methods in Enzymology* 124:412 (1986)). The dissociated cells are passed through an 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 μM glutamate for 5 minutes with or without increasing doses of glycine and excitatory amino acid antagonist or other drugs. After 5 minutes, the cultures are washed and incubated for 24 hours at 37° C. Neuronal cell damage is quantitated by measuring lactate dehydrogenase (LDH) activity that is released into the culture medium. The LDH activity is measured according to the method of Decker et al. (Decker et al., *J. Immunol. Methods* 15:16 (1988)).

The anticonvulsant activity of the glycine and excitatory amino acid antagonists can be assessed in the audiogenic seizure model in DBA-2 mice as follows. DBA-2 mice can be obtained from Jackson Laboratories, Bar Harbor, Maine. These mice at an age of <27 days develop a tonic seizure within 5–10 seconds and die when they are exposed to a sound of 14 kHz (sinus wave) at 110 dB (Lonsdale, D., *Dev. Pharmacol Ther.* 4:28 (1982)). Seizure protection is defined when animals injected with drug 30 minutes prior to sound exposure do. not develop a seizure and do not die during a 1 minute exposure to the sound. 21 day old DBA-2 mice are used for all experiments. Compounds are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists can be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death can be assessed as follows. When mice are injected with 200 mg/kg N-methyl-D-aspartate (NMDA) i.p., the animals will develop seizures followed by death within 5–10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant activity of the glycine antagonists can be assessed in the MES assays in mice. Electroshock was applied to male Swiss/Webster mice (20–30 g, Simonsen) through corneal electrodes (Swinyard, E. A. (1973) in *Anticonvulsant drugs*, Mercier J. Ed. Pergamon Press, Oxford pp. 47–65). The seizure stimulus parameters were: 50 mA, 60 Hz, rectangular pulse, width 0.8 msec, duration 200 msec. Tonic hind limb extension observed after application of the electrical stimulus was recorded as occurrence of seizure. The drug was applied i.v. as an aqueous Tris (Tromethamine) solution.

A series of different evaluations can be conducted on doses of the glycine/excitatory amino acid antagonists of the invention to determine the biological activity of the compounds both in normal gerbils and in animals exposed to 5 minutes of bilateral carotid occlusion. See Scheme VIII.

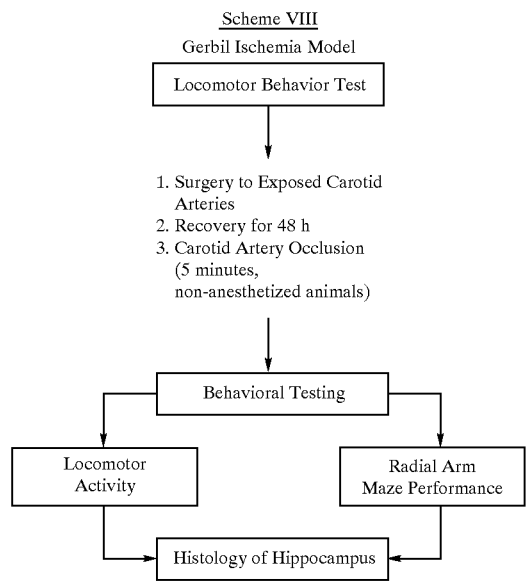

Scheme VIII
Gerbil Ischemia Model

These studies are conducted in animals who are conscious and have no other pharmacological agents administered to them. Gerbils are preinstrumented 48-hours prior to ischemia to allow for the complete elimination of the pentobarbital anesthetic that is employed. When tested with drugs, animals are given i.p. injections of the glycine/excitatory amino acid antagonist or vehicle. In the case of multiple injections, animals are given i.p. injections 2 hours apart and the final injection is given 30 minutes prior to the ischemic period or in the case of post treatment, the animals are given injections at 30 minutes, 2 hours, 4 hours, and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber, which is a two foot circular diameter arena with photobeam detection. Animals are individually placed in the 2 foot diameter chambers. The chambers are housed in a cabinet that is closed and noise is abated using both a background white noise generator and a fan. Animals are placed in these chambers in the case of the initial pharmacological evaluation for a period of 6 hours and the total activity during each successive hour is accumulated using the computer control systems.

Saline results in an initial high rate of activity, with the control animals showing a first hour activity level of about 1600 counts. This level of control activity is typical for the gerbil under these experimental conditions. As the session progresses, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity, which in the first hour of locomotor activity is substantially higher than during all other hours and progressively declines over the four hours to a very low value. In contrast to the progressive decline in activity over the four hour testing period, control animals that are exposed to five minutes of cortical ischemia demonstrate a completely different pattern of locomotor activity. During the first hour, there is a significant decline in activity that is followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/excitatory amino acid antagonists of the invention 30 minutes before the onset of carotid occlusion and then placed into the locomotor activity following one hour of reperfusion. It is expected that pretreatment of the gerbils with the glycine/excitatory amino acid antagonists of the invention will prevent both the post-ischemic decrease and increase in activity. Post-ischemic decreases in activity are expected to be near zero during the first hour following reperfusion. Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered i.p. at 6 hours, 4 hours, 2 hours, and 30 minutes prior to the onset of 5 minutes of ischemia.

At 24 hours, all animals are evaluated for differences in patrolling behavior using an 8-arm radial maze. In this procedure, animals are placed into the center start chamber of the maze, the barrier is removed, and the amount of time and the number of times the animal makes an error is recorded prior to completion of exploration in all 8 arms of the maze. An error is defined as the revisiting of an arm by an animal entering to the extent of its entire body without including its tail. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment with the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus can be evaluated in animals 7 days after ischemia reperfusion injury. Previous studies have demonstrated that neuronal degeneration begins to occur around 3 days following cerebral ischemia. By 7 days those neurons that have been affected will undergo cytolysis and have either completed degeneration or are readily apparent as dark nuclei and displaced nuclei or as cells with eosinophilic cytoplasm and pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or cells in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded, and sections made. Sections are stained with hematoxylin-eosin and neuronal cell counts are determined in terms of the number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis, which is seen if 10 minutes of ischemia is employed. Pretreatment with the glycine receptor antagonists of the invention is expected to produce a significant protection of hippocampal neuronal degeneration.

It is known that NMDA receptors are critically involved in the development of persistent pain following nerve and tissue injury. Tissue injury, such as that caused by injecting a small amount of formalin subcutaneously into the hindpaw of a test animal, has been shown to produce an immediate increase of glutamate and aspartate in the spinal cord (Skilling, S. R., et al., *J. Neurosci.* 10:1309–1318 (1990)). Administration of NMDA receptor blockers reduces the response of spinal cord dorsal horn neurons following formalin injection (Dickenson and Aydar, *Neuroscience Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain, such as, pain caused by surgery, by amputation (phantom pain), or by infliction of other wounds (wound pain). However, the use of conventional NMDA antagonists, such as, MK801 or CGS 19755, in preventing or treating chronic pain is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects.

The effects of the glycine receptor antagonists of the present invention on chronic pain can be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/mL, respectively. DMSO is used as vehicle control. All drugs are injected intraperitoneally (1 $\mu$l/g). The formalin test is performed -as described (Dubuisson and Dennis, *Pain* 4:H161–174 (1977)). Mice are observed in a plexiglass cylinder, 25 cm in diameter and 30 cm in height. The plantar surface of one hindpaw is injected subcutaneously with 20 $\mu$l of 5% formalin. The degree of pain is determined by measuring the amount of time the animal spends licking the formalin-injected paw during the following time intervals: 0–5' (early phase); 5'–10', 10'–15' and 15'–50' (late phase). To test whether the glycine/excitatory amino acid antagonists prevent chronic pain in the test animals, vehicle (DMSO) or drugs dissolved in vehicle at doses of 1 mg/kg to 40 mg/kg are injected intraperitoneally 30 minutes prior to the formalin injection. For each dose of drug or vehicle control at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time the mouse spends licking the formalin injected hindpaw, caused by increasing doses of glycine/excitatory amino acid antagonist.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their .derivatives.) Unfortunately, with continued use, the body builds up a tolerance for the opiate, and, thus, for continued relief, the patient must be subjected to progressively larger doses. This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Recent studies have suggested a modulatory role for the NMDA receptor in morphine tolerance. It has now been found that administration of quinoxaline diones can inhibit opiate tolerance by blocking the glycine co-agonist site associated with the NMDA receptor.

Compositions within the scope of this invention include all compositions wherein the compounds of the present invention are contained in an amount effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease, and Down's Syndrome, or in a method of treating a disease in which the pathophysiology of the disorder involves hyperactivity of the excitatory amino acids or NMDA receptor-ion channel related neurotoxicity or psychosis, the pharmaceutical compositions of the invention can comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention may be administered at a unit dosage level of from about 0.01 to about 50 mg/kg of body weight, or an equivalent amount of a pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg, of the compound or its solvates.

In addition to administering the compound as a raw chemical, the compounds of the invention can be administered as part of a pharmaceutical preparation containing suitable pharmaceutically acceptable carriers comprising excipients and auxiliaries that facilitate processing of the compounds into preparations that can be used pharmaceutically. Preferably, the preparations, particularly those preparations that can be administered orally and that can be used for the preferred type of administration, such as tablets, dragees, and capsules, and preparations that can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Basic salts are formed by mixing a solution of the particular 1,4-dihydroquinoxaline-2,3-dione of the present invention with a solution of a pharmaceutically acceptable non-toxic base, such as, sodium hydroxide, potassium hydroxide, sodium bicarbonate, sodium carbonate, or an amino compound, such as, choline hydroxide, Tris, bis-Tris, N-methylglucamine, arginine, and the like. See, U.S. application Ser. No. 08/148,268, supra.

The pharmaceutical compositions of the invention can be administered to any animal that may experience the beneficial effects of the compounds of the invention. Foremost among such animals are humans, although the invention is not intended to be so limited.

The pharmaceutical compositions of the present invention can be administered by any means that achieve their intended purpose. For example, administration may be by parenteral, subcutaneous, intravenous, intramuscular, intraperitoneal, transdermal, buccal, or ocular routes. Alternatively, or concurrently, administration may be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention may be administered in the form of eye drops that are substantially isotonic with tear fluid to achieve systemic administration. Preferably, such compositions will also comprise a permeation-enhancing agent, which aids the systemic absorption of the compounds of the present invention. See, U.S. Pat. No. 5,182,258. Alternatively, the compositions of the invention may be administered ocularly to treat or prevent optic nerve degeneration. In this embodiment, the compounds of the present invention are administered in the form of eye drops, as disclosed above, or may be injected into the vicinity of the optic nerve. In the alternative, thin ocular implants may be employed that slowly release the compounds of the present invention.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers, such as, saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions, and suitable organic solvents or solvent mixtures. In order to produce coatings resistant to gastric juices, solutions of suitable cellulose preparations, such as, acetyl-cellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers, such as, lactose, binders, such as, starches, and/or lubricants, such as, talc or magnesium stearate and, optionally, stabilizers. In soft capsules, the active compounds are preferably dissolved or suspended in suitable liquids, such as, fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances that increase the viscosity of the suspension, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention can be used to characterize the glycine binding site. The particularly preferred compounds that can be used for this purpose are isotopically radiolabelled derivatives, e.g., where one or more of the atoms are replaced with $^3$H, $^{11}$C, $^{14}$C, $^{15}$N, or $^{18}$F. Examples of preferred photoaffinity ligands are $^3$H or $^{18}$F-substituted 6-azido-5,7-difluoro-1,4-dihydroquinoxaline-2,3-dione and $^3$H-substituted 6-azido-5,7-dichloro-1,4-dihydroquinoxaline-2,3-dione.

The following examples are illustrative, but not limiting, of the method and compositions of the present invention. Other suitable modifications and adaptations of the variety of conditions and parameters normally encountered in clinical therapy and obvious to those skilled in the art are within the spirit and scope of the invention.

EXAMPLES

Example 1

Preparation of 6,7-Difluoro-5-nitro-1,4-dihydro-2,3-quinoxalinedione

Preparation of 6,7-Difluoro-1,4-dihydro-2,3-quinoxalinedione

Method 1.

4,5-Difluoro-1-diaminobenzene. 4,5-Difluoro-1,2-diaminobenzene was prepared using an adaptation of the method of Tsuji et al., (Tsuji, Y. et al., *J. Org. Chem.* 55:580 (1990)). Zn powder (942 mg, 14.4 mmol), CaCl$_2$ (94.4 mg), H$_2$O (1.0 mL) and 4.0 mL EtOH were combined and brought to reflux as described for 4-fluoro-1,2-diaminobenzene (see Example 11) and to this mixture was added slowly dropwise a solution of 4,5-difluoro-2-nitroaniline (200 mg, 1.15 mmol) in 2 mL EtOH. Analysis and workup were as described for 4-fluoro-1,2-diaminobenzene (Example 11) except that the reaction was dissolved in 5 mL H$_2$O and the solution extracted with 3×10 mL Et$_2$O. The organic layers were combined and treated with activated charcoal, dried (MgSO$_4$), and filtered through a pad of Celite. The solvent was evaporated at reduced pressure to yield 111.5 mg (67.3%) of a brown crystalline solid. $^1$H NMR (CDCl$_3$) δ 3.34 (br s, 4H, NH$_2$), 6.53 (t, 2H, ArH).

6,7-Difluoro-1,4-dihydro-2,3-quinoxalinedione. The title compound (Sarges, R. et al., *J. Med. Chem.* 33:2240 (1990)) was prepared using an adaptation of the method of Cheeseman. (Cheeseman, G. W. H. *J. Chem. Soc.* 1171 (1962)). A mixture of diethyl oxalate (1.11 g, 7.63 mmol and 4,5-difluoro-1,2-diaminobenzene (110 mg, 0.763 mmol) was heated to reflux under N$_2$ for 2 h. The reaction was allowed to cool to room temperature and the solid was collected by vacuum filtration, rinsed with hexanes, and air dried. This gray brown solid was recrystallized from 20 mL of EtOH and the brown-white crystals collected by vacuum filtration and the crystals further dried under vacuum (0.5 torr, 25° C.) to yield 45.3 mg (30.0%); mp>360° C. (lit.>310° C.); $^1$H NMR (d$_6$-acetone) δ 7.19 (t, 2H, ArH, J$_{H-F}$=9.3), 10.9 (br s, 2H, NH).

Method 2.

To a solution of 2.0 g (11.5 mmol) 4,5-difluoro-2-nitroaniline (Aldrich, used as received) in EtOH (20 mL) was added 100 mg of 10% Pd/C. The suspension was shaken under H$_2$ (40–20 psi) for 3 h. The catalyst was removed by filtration and washed with EtOH (2×15 mL). The EtOH solution was rota-evaporated to dryness. To the residual black solid was added oxalic acid dihydrate (1.74 g, 13.8 mmol) and 2 N aq HCl (18 mL). The mixture was heated at 125° C. with stirring for 3 h, then cooled to 25° C. The black precipitate was collected by vacuum filtration, and washed with water (5×5 mL). The wet product was dissolved in 0.2 N aq NaOH (100 mL) with stirring, then filtered. The clear, slightly orange-yellow, filtrate was acidified by the addition of 2 N aq HCl with stirring to pH 4. The off-white precipitate was collected by vacuum filtration, washed with water, and dried under 1 mm Hg at 40° C. to give 1.83 g (89%) of the title compound as a cream colored powder. Mp>360° C. IR (KBr) 3454, 3120, 1708, 1530, 1400, 1298 cm$^{-1}$. $^1$H NMR (DMSO-d$_6$) 11.939 (s, 2H), 7.054 (m, 2H).

To a suspension of 6,7-difluoro-1,4-dihydro-2,3-quinoxalinedione (837 mg, 4.23 mmol) in trifluoroacetic acid (30 mL). was added KNO$_3$ (512 mg, 5.07 mmol). The mixture was stirred at 55° C. for 20 h. At the end of this time, 256 mg (2.50 mmol) of KNO$_3$ was added and the reaction mixture was stirred at 55° C. for 20 h, then another 256 mg (2.50 mmol) of KNO$_3$ was added and the mixture was stirred at 55° C. for 20 h. The reaction mixture was then rota-evaporated to dryness. Ice-old water (about 15 mL) was added to the residual solid. The solid was collected by vacuum filtration, washed with ice-cold water (5×5 mL), and dried at 40° C. under 1 mm Hg for 14 h, giving 700 mg (68%) of the title compound as a yellow powder. Mp 288–90° C. (dec.). IR (KBr) 3424, 3226, 1752, 1717, 1554, 1356, 1304 cm$^{-1}$. $^1$H NMR (DMSO-d$_6$): 12.249 (s, 1H), 11.864 (bs, 1H), 7.330 (dd, 1H, J=10.5, 7.8 Hz). Analysis for C$_8$H$_3$F$_2$N$_3$O$_4$, calcd: C, 39.50, H, 1.24, N, 17.29; found: C, 39.42, H, 1.26, N, 17.08.

Example 2

Preparation of 5,6,7-Trifluoro-1,4-dihydro-2,3-quinoxalinedione 2,3,4-Trifluoroacetanilide. To a pink solution of 2,3,4-trifluoroaniline (1.04 g, 9.45 mmol) in chloroform (12 mL) was added acetic anhydride (1.63 g, 16.0 mmol), giving a pale pink solution that was stirred overnight under nitrogen. The chloroform was removed in vacuo to give 1.35 g (99%) of the acetanilide as a white solid: $^1$H NMR (CDCl$_3$), 2.28 (s, 3H), 6.95 (m, 1H), 7.31 (m, 1H), 7.97 (m, 1H).

3,4,5-Trifluoro-1,2-phenylenediamine. To 2,3,4-trifluoroacetanilide (1.35g, 7.09 mmol) is added concentrated sulfuric acid (8 mL). While the flask is in an ice bath, KNO$_3$ is slowly added, giving a tan mixture, that is stirred overnight. The reaction mixture, now dark red, is then added to ice water (45 mL), instantly giving an orange precipitate. The volatile compound, presumably 2,3,4-trifluoro-6-nitroaniline, is dissolved in ethyl acetate (18 mL) and ethyl alcohol (12 mL). To the orange solution is added stannous chloride dihydrate (7.6 g, 34 mmol). The resulting mixture is stirred and brought to reflux under N$_2$ for 4 h. The mixture is added to ice water (40 mL) and basified with 2N NaOH (40 mL). It is extracted with ethyl acetate (3×20 mL) and the combined extracts are washed with water (20 mL) and brine (20 mL). This dark red solution is dried (MgSO$_4$) and evaporated to give 285 mg (25%) of the diamine as a dark red solid. $^1$H NMR (CDCl$_3$), 3.22 (br s, 2H), 3.46 (br s, 2H), 6.32 (m, 1H).

5,6,7-Trifluoro-1,4-dihydro-2,3-quinoxalinedione. To a brown solution of 3,4,5-trifluoro-1,2-phenylenediamine (285 mg, 1.75 mmol) in aqueous 2N HCl (10 mL) is added oxalic acid (221 mg, 1,75 mmol). The brown mixture is brought to reflux and stirred under N$_2$ overnight. The mixture is filtered to yield 139 mg (37%) of crude title compound. An analytical sample is prepared by dissolving 42 mg of this brown powder in 2.5 mL-boiling ethanol. Upon cooling, brown, rod-like, crystals are formed, which are filtered and dried in vacuo to-yield 15 mg (36%) of pure title compound: $^1$H NMR (DMSO-d$_6$), 6.91 (m, 1H), 12.02 (s, 1H), 12.19 (s, 1H); analysis calculated for C$_8$H$_3$F$_3$N$_2$O$_2$: C, 44.46; H, 1.40; N, 12.96. Found: C, 44.42; H, 1.16; N, 12.76.

Example 3

Preparation of 5-Nitro-6,7,8-trifluoro-1,4-dihydro-2,3-quinoxalinedione

To 5,6,7-trifluoro-1,4-dihydro-2,3-quinoxalinedione (93 mg, 0.43 mmol) is added concentrated sulfuric acid (0.5 mL). While the flask is in an ice bath, KNO$_3$ is slowly added, giving a brown mixture, which is stirred overnight. The reaction mixture, now dark red, is then added to ice water (5 mL), instantly giving an orange precipitate, which is collected by centrifugation. The powder is crystallized from EtOH (5 mL) and dried in vacuo to yield 24 mg (20%) of pale orange microcrystals. $^1$H NMR (DMSO-d$_6$), 11.9 (br s, 1H), 12.6 (br s, 1H).

Example 4

Preparation of 6-Chloro-5,7-difluoro-1,4-dihydroquinoxaline-2,3-dione

3-Chloro-2,4-difluoro-(trifluoroacetamido)benzene. To a solution of 10.5 g (64.3 mmol) of 3-chloro-2,4-difluoroaniline in 25 mL of dioxane kept in an ice-bath was added dropwise 10 mL (14.8 g, 70.4 mmol) of trifluoroacetic anhydride. The solution was stirred at room temperature for 20 h. It was then added to 150 mL of ice-water and the mixture was stirred for 1 h. It was filtered, washed with water, and dried to leave an almost colorless solid 16.1 g (96%); mp 73–74° C.; $^1$H NMR (CDCl$_3$), 7.068 (m, 1), 7.976 (mb, 1), 8.146 (m, 1).

3-Chloro-2,4-difluoro-6-nitro-(trifluoroacetamido) benzene. To a solution of 15.1 g (58.1 mmol) of 3-chloro-2,4-difluoro-(trifluoroacetamido)-benzene in 80 mL of H$_2$SO$_4$ kept in an ice-bath was added dropwise 10 mL of HNO$_3$. Solid precipitate was observed during addition of HNO$_3$. The mixture was stirred in an ice-bath for 4 h, then added to 600 mL of ice-water. The precipitate was filtered, washed with water, and dried to leave an almost colorless solid (16.8 g, 95%); mp 124–125° C.; $^1$H NMR (CDCl$_3$), 7.69 (dd, 1), 8.936 (mb, 1).

3-Chloro-2,4-difluoro-6-nitroaniline. A solution of 6.35 g (20.8 mmol) of 3-chloro-2,4-difluoro-6-nitro-(trifluoroacetamido)benzene in 60 mL of 7% K$_2$CO$_3$ methanol/water (3:2) was stirred at 25° C. for 4 h. The solution was evaporated to remove the methanol. Solid was observed in the residue. It was filtered, washed with water, and dried to leave 301 mg of a crystalline yellow solid; mp 96–97° C.; $^1$H NMR (CDCl$_3$), 6.07 (mb, 2), 7.815 (dd, 1, J=1.92, 9.13). More solid was observed after the mother aqueous solution was allowed to stand at room temperature overnight. It was filtered, washed with water, and dried to leave a yellow solid (1.01 g). More solid was crystallized from the mother solution. It was collected three more times to provide 2.48 g of a yellow solid. $^1$H NMR is identical with above, total yield 3.80 g (87%).

4-Chloro-3,5-difluoro-1,2-phenylenediamine. A solution of 348 mg (1.67 mmol) of 3-chloro-2,4-difluoro-6-nitroaniline and 1.57 g (8.28 mmol) of SnCl$_2$ in 8 mL of ethanol was heated at 70° C. for 2 h. The solution was evaporated to remove the ethanol. The residue was treated with 2N NaOH to pH=13. White precipitate was observed. The mixture was extracted with CHCl$_3$ (3×10 mL). The extract was dried (MgSO$_4$) and evaporated to leave a red solid (285 mg, 95%); mp 77–78° C.; $^1$H NMR (CDCl$_3$), 3.156 (b, 2), 3.704 (b, 2), 6.352 (dd, 1, J=1.86, 9.95).

6-Chloro-5,7-difluoro-1,4-dihydroquinoxaline-2,3-dione. A mixture of 230 mg (1.29 mmol) of 4-chloro-3,5-difluoro-1,2-phenylenediamine and 125 mg (1.38 mmol) of oxalic acid in 4 mL of 2N HCl was refluxed for 3 h and cooled to room temperature. The mixture was filtered, washed with water, and dried to leave a brown solid (245 mg, 82%); mp>250° C.; $^1$H NMR (DMSO-d$_6$), 6.921 (d, 1, J=9.61), 12.143 (s, 1), 12.168 (s, 1). MS, 232 (M$^+$, 100), 204 (80), 176 (40), 149 (70), 171 (80). HRMS calcd for C$_8$H$_3$$^{35}$ClF$_2$N$_2$O$_2$, 231.9848, found 231.9851.

Example 5

Preparation of 7-Chloro-6,8-difluoro-5-nitro-1,4-dihydroquinoxaline-2,3-dione

To a solution of 120 mg (5.16 mmol) of 6-chloro-5,7-difluoro-1,4-dihydroquinoxaline-2,3-dione in 1 mL of H$_2$SO$_4$ (97%) kept in an ice bath was added portionwise 60 mg (0.59 mmol) of KNO$_3$. The solution was stirred at room temperature for 14 h and 60 mg of KNO$_3$ was added. It was stirred at room temperature for 24 h, then diluted with ice-water (4 mL), filtered, washed with water, and dried to leave a yellow solid (94 mg, 65%). The solid was purified by NaOH/HCl precipitation to leave 63 mg of yellow solid; mp>250° C.; $^1$H NMR (DMSO-d$_6$) 12.11 (mb, 1), 12.503 (s, 1).

Example 6

Preparation of 7-Fluoro-5-nitro-1,4-dihydro-2,3-quinoxalinedione

4-Fluoro-2,6-dinitroaniline. A solution of 4-fluoro-2,6-dinitro-(trifluoroacetamido)benzene (297 mg, 1.00 mmol) in 10% $K_2CO_3$ (10 mL) was refluxed for 1 h, then cooled to room temperature to give yellow crystals. It was filtered and washed with cold water (2×1 mL), affording 105 mg (52%) of the title compound. $^1$H NMR (DMSO-$d_6$): δ 8.254 (s, 2H), 8.460 (d, 2H, J=8.4).

1,2-diamino-4-fluoro-6-nitrobenzene. A solution of 4-fluoro-2,6-dinitroaniline (125 mg, 0.62 mmole) in freshly prepared 6% $(NH_4)_2S$ (5 mL) and EtOH (5 mL) was refluxed for 30 min, diluted with water (10 mL) and kept at 4° C. for several hours. The precipitate was collected and washed with cold water (2×1 mL), affording 53 mg (50%) of 1,2-diamino-4-fluoro- 6-nitrobenzene as red crystals. $^1$H NMR (CDCl$_3$): δ 3.619 (s, 2H), 5.724 (s, 2H), 6.732 (dd, 1H, $J_1$=2.4 Hz, $J_2$=8.4 Hz), 7.403 (dd, 1H, $J_1$=2.4 Hz, $J_2$=8.4 Hz).

7-Fluoro-5-nitro-1,4-dihydro-2,3-quinoxalinedione. A mixture of 1,2-diamino4-fluoro-6-nitrobenzene (80 mg, 0.46 mmole) and oxalic acid dihydrate (70 mg, 0.56 mmole, used as received) in 4N HCl (4 mL) was refluxed at 120–5° C. for 3 h, then cooled to room temperature. The mixture was centrifuged and the supernatant was removed. The yellow solid was washed with cold water (2×2 mL), collected by filtration, and dried in vacuo for 2 h, affording 45 mg (42%) of crude 7-fluoro-5-nitro-1,4-dihydro-2,3-quinoxalinedione as a yellow powder. The crude product was taken up in 1N NaOH (1 mL) and filtered. The filtrate was acidified to pH=3, affording 35 mg (33%) of 7-fluoro-5-nitro-1,4-dihydro-2,3-quinoxalinedione; mp: 333–335° C. (dec.); IR (KBr, cm$^{-1}$): 3427, 3328, 3104, 3072, 1716, 1545. $^1$H NMR (DMSO-$d_6$): δ 12.418 (s, 1H), 11.149 (s, 1H), 7.819 (dd, $J_1$=2.4 Hz, $J_2$=9.0 Hz, 1H), 7.297 (dd, $J_1$=2.4 Hz, $J_2$=9.0 Hz, 1H); HRMS: calcd for $C_8H_4FN_3O_4$ (M$^+$) m/z: 225.0185; found: 225.0188.

Example 7

Preparation of 6-Chloro-7-methyl-5-nitro-1,4-dihydroquinoxaline-2,3-dione

2-Chloro-4-fluoro-5-nitrotoluene. To a stirred solution of 2-chloro-4-fluorotoluene (2.000 g, 1.383 mmol, Aldrich, used as received) in conc. $H_2SO_4$ (15.0 mL) at 0° C., KNO$_3$ (1.400 g, 1.385 mmol) was added in one lot. The resulting pale yellow solution was allowed to warm to 28° C. and stirred overnight at 28° C. It was then poured into ice (100 g) and extracted with ethyl acetate (2×100 mL). Ethyl acetate was dried over anhydrous $Na_2SO_4$, removed under vacuum, and the resulting oil was dried further under vacuum to afford 2.085 g (80%) of title compound as an oil, which was used as such for the next reaction; $^1$H NMR (CDCl$_3$): δ 2.422 (s, 3H), 7.325 (d, 1H, $J_1$=10.2 Hz), 7.973 (d, 1H, $J_1$=5.2 Hz).

N-(5'-Chloro-4'-methyl-2'-nitrophenyl)glycine sodium salt. To a stirred solution of 2-chloro-4-fluoro-5-nitrotoluene (2.080 g, 10.97 mmol, as prepared above) in DMF (11.0 mL) at 70° C., was added dropwise, a solution of sodium glycinate (1.065 g, 10.97 mmol, Aldrich, used as received) in water (11.0 mL). The resulting suspension was stirred overnight at 70° C., cooled to room temperature, and the resulting red solid was filtered, washed with acetone (35 mL), and dried under vacuum to give 1.005 g (37%) of the pure ($^1$H NMR) title compound as a red powder; $^1$H NMR (DMSO-$d_6$): δ 2.184 (s, 3H), 3.396 (d, 2H, J=4.2 Hz), 6.852 (s, 1H), 7.991 (s, 1H), 8.671 (s, 1H).

6-Chloro-3,4-dihydro-7-methylquinoxaline-2(1H)-one. A solution of N-(5'-chloro-4'-methyl-2'-nitrophenyl)glycine (1.000 g, 4.088 mmol, as prepared above) and tin (II) chloride dihydrate (2.767 g, 12.26 mmol, Aldrich, used as received) in ethanol (20.0 mL) was refluxed for 30 min. It was then cooled to room temperature and the precipitated solid was filtered, washed with ethanol (4.0 mL), and dried under vacuum to yield 0.251 g (31%) of the title compound as a yellow powder; $^1$H NMR (DMSO-$d_6$): δ 2.093 (s, 3H), 3.657 (d, 2H, J=1.5 Hz), 5.984 (s, 1H), 6.583 (s, 1H), 6.632 (s, 1H), 10.253 (s, 1H).

6-Chloro-7-methyl-5-nitro-1,4-dihydroquinoxaline-2,3-dione. To a stirred suspension of 6-chloro-3,4-dihydro-7-methylquinoxaline-2(1H)-one (0.150 g, 0.763 mmol, as prepared above) in $CF_3COOH$ (1.6 mL), excess fuming $HNO_3$ (0.40 mL) was added and the resulting red solution was stirred overnight at 28° C. The solvent was removed under vacuum and the residue was diluted with water (3.0 mL). The precipitated solid was filtered and dried under vacuum to yield 0.151 g (77%) of pure (purity by HPLC-100%) title compound as a light yellow powder; m.p.-darkens at 350° C.; $^1$H NMR (DMSO-$d_6$): δ 2.311 (s, 3H), 7.149 (s, 1H), 12.107 (s, 1H) 12.193 (s, 1H); Elemental analysis for $C_9H_6ClN_3O_4$: calcd C, 42.29%; H, 2.37%; N, 16.44%, found C, 42.46%; H, 2.10%; N, 16.33%.

Example 8

Preparation of 7-Chloro-6-methyl-5-nitro-1,4-dihydroquinoxaline-2,3-dione

2-Chloro-5-fluoro-4-nitrotoluene. To a stirred solution of 2-chloro-5-fluorotoluene (0.500 g, 3.46 mmol, Lancaster, used as received) in conc. $H_2SO_4$ (5.0 mL) at 0° C., KNO$_3$ (0.350 g, 3.46 mmol) was added in one lot. The resulting pale yellow solution was allowed to warm to 28° C. and stirred overnight at 28° C. It was then poured into ice (50 g) and extracted with ether (2×50 mL). The ether was dried over anhydrous $Na_2SO_4$, removed under vacuum, and the resulting oil was dried further under vacuum to afford 0.616 g (94%) of the title compound as an oil, which was used as such for the next reaction; $^1$H NMR (CDCl$_3$): δ 2.459 (s, 3H), 7.193 (d, 1H, $J_1$=11.1 Hz), 8.083 (d, 1H, $J_1$=6.6 Hz).

N-(4'-Chloro-5'-methyl-2'-nitrophenyl)glycine sodium salt. To a stirred solution of 2-chloro-5-fluoro-4-nitrotoluene (0.605 g, 3.19 mmol, as prepared above) in DMF (3.0 mL) at 70° C., was added dropwise, a solution of sodium glycinate (0.310 g, 3.19 mmol, Aldrich, used as received) in water (3.0 mL). The resulting suspension was stirred overnight at 70° C. The suspension was cooled to room temperature and the resulting red solid was filtered, washed with chloroform (10 mL) and dried under vacuum to give 0.360 g (46%) pure ($^1$H NMR) title compound as a red powder; $^1$H NMR (DMSO-$d_6$): δ 2.276 (s, 3H), 3.431 (d, 2H, J=4.2 Hz), 6.848 (s, 1H), 7.963 (s, 1H), 8.773 (s, 1H).

7-Chloro-3,4-dihydro-6-methylquinoxaline-2(1H)-one. A solution of N-(4'-chloro-5'-methyl-2'-nitrophenyl)glycine sodium salt (0.300 g, 1.23 mmol, as prepared above) and tin (II) chloride dihydrate (0.830 g, 3.68 mmol, Aldrich, used as received) in ethanol (4.0 mL) was refluxed for 30 min. It was then cooled to room temperature and the precipitated solid was filtered, washed with ethanol (1.0 mL) and dried under vacuum to yield 0.160 g (66%) of the title compound as a yellow powder; $^1$H NMR (DMSO-$d_6$): δ 2.099 (s, 3H), 3.655 (s, 2H), 6.037 (s, 1H), 6.538 (s, 1H), 6.685 (s, 1H), 10.241 (s, 1H).

7-Chloro-6-methyl-5-nitroquinoxaline-2(1H),3(4H)-dione. To a stirred suspension of 7chloro-3,4-dihydro-6-methyl-quinoxaline-2(1H)-one (0.100 g, 0.509 mmol, as prepared above) in $CH_3COOH$ (3.0 mL), excess fuming $HNO_3$ (0.30 mL) was added and the resulting red solution was stirred overnight at 28° C. The solvent was removed under vacuum and the residue diluted with water (4.0 mL). The precipitated solid was filtered and dried under vacuum to yield 0.067 g (52%) of pure (purity by HPLC: 100%) title compound as a light yellow powder; m.p.-darkens at 340° C.; $^1$H NMR (DMSO-d$_6$) δ 2.184 (s, 3H), 7.263 (s, 1H), 11.948 (s, 1H), 12.144 (s, 1H); Elemental analysis for $C_9H_6CN_3O_4.H_2O$ calcd C, 40.85%; H, 2.28%; N, 15.87%; found C, 40.63%; H, 2.05%; N, 15.75%.

Example 9

Preparation of 6-Bromo-7-chloro-5-nitro-1,4-dihydroquinoxaline-2,3-dione 2,5-Dichloro-4-nitrobromobenzene: A solution of 2-bromo-1,4-dichlorobenzene (1.000 g, 4.443 mmol, Aldrich, used as received) in fuming HNO$_3$ (7.0 mL) was stirred at 50° C. for 1.5 h and poured into ice (80 g). Yellowish white solid was filtered, washed with water (10 mL), and dried under vacuum to obtain 1.14 g (95%) of pure ($^1$H NMR) title compound as a yellowish white powder; m.p. 50–53° C. (lit m.p. 57–58° C.; Fox, D. L. and Turner, E. E., J. Chem. Soc. 1859 (1930)); $^1$H NMR (CDCl$_3$): δ 7.863 (s, 1H), 8.030 (s, 1H). This material was used as such for the next reaction.

N-(5'-Bromo-4'-chloro-2'-nitrophenyl)glycine sodium salt: To a stirred solution of 2,5-dichloro-4-nitrobromobenzene (1.000 g, 3.691 mmol, as prepared above) in DMF (10.0 mL) at 65° C., was added, dropwise, a solution of NaHCO$_3$ (0.316 g, 3.76 mmol) and glycine (0.280 g, 3.73 mmol, Aldrich, used as received) in water (3.8 mL). The resulting suspension was stirred at 65° C. for 65 h. The bright orange suspension was then cooled to room temperature, filtered, washed with water (1.0 mL), and dried under vacuum to afford 0.284 g (98%, based on recovered starting material) of the pure ($^1$H NMR) title compound as an orange powder; m.p. 264–265° C. (decomposed); $^1$H NMR (DMSO-d$_6$): δ 3.451 (d, 2H, J=3.9 Hz), 7.199 (s, 1H), 8.130 (s, 1H), 8.793 (t, 1H, J=3.6Hz). It was used as such for the next reaction.

6-Bromo-7-oro-3,4-dihydroquinoxaline-2(1H)-one: A solution of N-(5'-bromo-4'-chloro-2'-nitrophenyl)glycine sodium salt (0.255 g, 0.824 mmol, as prepared above) and tin (II) chloride dihydrate (0.560 g, 2.48 mmol, Aldrich, used as received) in ethanol (6 mL) was refluxed for 3 h. It was then cooled to room temperature and allowed to stand overnight at room temperature. The white solid was filtered and dried to yield 0.038 g (18%).of the pure ($^1$H NMR) title compound as white flakes; m.p. 230–232° C.; $^1$H NMR (DMSO-d$_6$): δ 3.732 (s, 2H), 6.371 (s, 1H), 6.830 (s, 1H), 6.912 (s, 1H), 10.437 (s, 1H). Extraction of the filtrate with ethyl acetate (30 mL) gave 0.136 g (68%) more product for a combined yield of 86%. The product was used as such for the next reaction.

6-Bromo-7-chloro-5-nitroquinoxaline-2(1H)-one: To a stirred suspension of 6-bromo-7-chloro-3,4-dihydroquinoxaline-2(1H)-one (0.06 g, 0.23 mmol, as obtained above) in CF$_3$COOH (0.5 mL) was added fuming HNO$_3$ (0.02 mL, 0.46 mmol) and the resulting reddish yellow suspension was stirred at room temperature overnight. The cream colored suspension so obtained was poured into ice (2.5 mL) and the precipitated solid was filtered, washed with water (1.0 mL), and dried under vacuum to afford 0.049 g (70%) of the title compound as a cream colored powder. $^1$H NMR (DMSO-d$_6$): δ 7.577 (s, 1H), 8.251 (s, 1H), 12.879 (s, 1H). The crude product was used as such for the final reaction.

6-Bromo-7-chloro-5-nitro-1,4-dihydroquinoxaline-2,3-dione: To a stirred solution of 6-bromo-7-chloro-5-nitroquinoxaline-2(1H)-one (0.025 g, 0.082 mmol, as prepared above) in conc. H$_2$SO$_4$ (0.5 mL) was added KNO$_3$ (0.011 g, 0.11 mmol) and the resulting dark red solution was stirred at room temperature for 65 h. The solution was then cooled in an ice-bath and diluted with ice to a total volume of 5.0 mL. The precipitated solid was filtered, washed with water (2.0 mL) and dried under vacuum to obtain 0.019 g (72%) crude product. It was purified as follows. 0.016 g crude product was taken up in 1N NaOH (1.1 mL). The insoluble solid was centrifuged and the supernatant liquid was acidified with conc. HCl to pH~2. The precipitated solid was filtered, washed with water (1.0 mL), and dried under vacuum to furnish 0.010 g (38%) pure (purity by HPLC>97%) title compound as a cream colored powder; m.p. 338–343° C. (decomposed); $^1$H NMR (DMSO-d$_6$): δ 7.351 (s, 1H), 12.251 (s overlapped by a br s, 2H); Elemental analysis for $C_8H_3BrClN_3O_4$, calcd: C, 29.98%; H, 0.94%; N, 13.11%, found: C, 29.79; H, 0.77; N, 12.71.

Example 10

Preparation of 6-Bromo-7-Fluoro-5-nitro-1,4-dihydroquinoxaline-2,3-dione

1-Bromo-2,5-difluoro-4-nitrobenzene: To a stirred solution of 1-bromo-2,5-difluorobenzene (1.000 g, 5.181 mmol, Aldrich, used as received) in conc. H$_2$SO$_4$ (8.0 mL) at 0° C., KNO$_3$ (0.525 g, 5.19 mmol) was added in one lot. The resulting yellow solution was allowed to warm to 28° C. and stirred at 28° C. overnight. It was then poured into ice (80 g) and extracted with ethyl acetate (75 mL). The ethyl acetate was dried over anhydrous Na$_2$SO$_4$, removed under vacuum, and the resulting white solid was dried further under vacuum to afford 1.102 g (89%) of the title compound as a white powder; m.p. 58–60° C.; $^1$H NMR (CDCl$_3$): δ 7.591 (dd, 1H, J$_1$=9.6 Hz, J$_2$=5.4 Hz), 7.891 (t, 1H, J=6.9 Hz).

N-(5'-Bromo-4'-fluoro-2'-nitrophenyl)glycine sodium salt: To a stirred solution of 1-bromo-2,5-difluoro-4-nitrobenzene (1.100 g, 4.622 mmol, as prepared above) in DMF (11.0 mL) at 70° C., was added, dropwise, a solution of sodium glycinate (0.451 g, 4.65 mmol, Aldrich, used as received) in water (5.0 mL). The resulting solution was stirred overnight at 70° C. The solution was cooled to room temperature and the bright orange solid was filtered, washed with cold acetone (10 mL) and dried under vacuum to give 0.469 g (35%) of the title compound as a bright orange powder; $^1$H NMR (DMSO-d$_6$): δ 3.458 (d, 2H, J=3.9 Hz), 7.148 (d, 1H, J=6.0 Hz), 7.944 (d, 1H, J=9.3 Hz), 8.740 (s, 1H).

6-Bromo-3,4-dihydro-7-fluoro-quinoxaline-2(1H)-one: A solution of N-(5'-bromo-4'-fluoro-2'-nitrophenyl)glycine sodium salt (0.450 g, 1.54 mmol, as prepared above) and tin (II) chloride dihydrate (1.039 g, 4.605 mmol, Aldrich, used as received) in ethanol (7.0 mL) was refluxed for 30 min. It was then cooled to room temperature and solvent was removed under vacuum. The residue was diluted with water (15.0 mL) and basified with 10% Na$_2$CO$_3$ to pH~8. The resulting suspension was extracted with ethyl acetate (100 mL). The ethyl acetate was dried over anhydrous Na$_2$SO$_4$ and removed under vacuum to yield 0.241 g (64%).of the title compound as a yellow powder, m.p. 214–216° C.; $^1$H NMR (DMSO-d$_6$): δ 3.684 (s, 2H), 6.062 (s, 1H), 6.631 (d, 1H, J=9.3 Hz), 6.825 (d, 1H, J=6.6 Hz), 10.303 (s, 1H).

6-Bromo-7-fluoro-5-nitro-1,4-dihydroquinoxaline-2,3-dione: To a stirred solution of 6-bromo-3,4-dihydro-7- fluoro-quinoxaline-2(1H)-one (0.050 g, 0.20 mmol, prepared as above) in $CF_3COOH$ (1.0 mL), excess fuming $HNO_3$ (0.10 mL) was added and the resulting red suspension was stirred overnight at 28° C. Solvent was removed under vacuum and the residue was diluted with water (2.0 mL). The precipitated solid was filtered, washed with water (2.0 mL), and dried in a drying pistol (toluene reflux) to yield 0.034 g (55%) of pure ($^1$H NMR) title compound as a yellow powder; m.p. 323–327° C.; $^1$H NMR (DMSO-$d_6$): δ 7.179 (d, 1H, J=9.0 Hz), 12.208 (s, 1H), 12.317 (s, 1H); Elemental analysis for $C_8H_3BrFN_3O_4$ calcd. C, 31.60%; H, 0.99%; N, 13.82%, found C, 31.30%; H, 0.87%; N, 13.66%.

Example 11

Preparation of 7-Bromo-6-fluoro-5-nitro-1,4-dihydroquinoxaline-2,3-dione

1-Bromo-2,4-difluoro-5-nitrobenzene: To a stirred solution of 1-bromo-2,4-difluorobenzene (0.512 g, 2.65 mmol, Aldrich, used as received) in conc. $H_2SO_4$ (5.0 mL) at 0° C., $KNO_3$ (0.275 g, 2.72 mmol) was added in one lot. The resulting solution was allowed to warm to 28° C. and stirred at that temperature overnight. It was then poured into ice (50 g) and extracted with ethyl acetate (50 mL). The ethyl acetate was dried over anhydrous $Na_2SO_4$, removed under vacuum and the resulting oil dried further under vacuum to afford 0.576 g (91%) of the pure ($^1$H NMR) title compound as a light red oil; $^1$H NMR (CDCl$_3$); δ 7.141 (dd, 1H, $J_1$=10.2 Hz, $J_2$=7.8 Hz), 8.375 (t, 1H, J=7.5 Hz).

N-(4'-Bromo-5'-fluoro-2'-nitrophenyl)glycine and N-(2'-bromo-5'-fluoro-4'-nitrophenyl)glycine: To a stirred solution of 1-bromo-2,4-difluoro-5-nitrobenzene (365 mg, 1.53 mmol, as prepared above) in DMF (3.0 mL), was added dropwise, a solution of sodium glycinate (0.152 g, 1.57 mmol, Aldrich, used as received) in water (0.6 mL). The resulting suspension was stirred at 28° C. overnight. The solvent was removed under vacuum and the resulting slurry was cooled in an ice-bath. 1N HCl (1.5 mL) was added to it which instantly gave a yellow solid that was filtered and dried in a drying pistol (toluene reflux) to give 0.175 g (39%) of a mixture of the title compounds in a ratio of 1.0:0.6 ($^1$H NMR) as a yellow powder; $^1$H NMR (DMSO-$d_6$): δ 4.039 (d, 2H, J=6 Hz), 4.109 (d, 2H, J=5.4 Hz), 6.691 (d, 1H, J=14.7 Hz), 6.900 (s, 1H), 7.005 (d, 1H, J=12.0 Hz), 8.219 (d, 1H, J=8.1 Hz), 8.337 (d, 1H, J=7.5 Hz), 8.494 (s, 1H). The separation of the mixture was not feasible at this stage; hence, it was used as such for the next reaction.

7-Bromo-3,4-dihydro-6-fluoro-quinoxaline-2(1H)-one: A solution of a mixture of N-(4'-bromo-5'-fluoro-2'-nitrophenyl)glycine and N-(2'-bromo-5'-fluoro-4'-nitrophenyl)glycine (0.150 g, 0.512 mmol, as prepared above) and tin (II) chloride dihydrate (0.346 g, 1.53 mmol, Aldrich, used as received) in ethanol (3.0 mL) was refluxed for 30 min. It was then cooled to room temperature and the solvent was removed under vacuum. The residue was diluted with water (10 mL) and basified with saturated $NaHCO_3$ (3.0 mL) to pH~8. The resulting white suspension was extracted with ethyl acetate (30 mL). The ethyl acetate was dried over anhydrous $Na_2SO_4$ and removed under vacuum to yield 0.050 g of crude product, which was purified by precipitation from ethanol:water (1:1) to give 30 mg (24%) of the pure ($^1$H NMR) title compound as a light yellow powder; m.p. 172° C. (decomposed); $^1$H NMR (DMSO-$d_6$): δ 3.73 (s, 2H), 6.37 (s, 1H), 6.551 (d, 1H, J=10.2 Hz), 6.825 (d, 1H, J=6.6 Hz), 10.303 (s, 1H).

7-Bromo-6-fluoro-5-nitro-1,4-dihydroquinoxaline-2,3-dione: To a stirred solution of 7-bromo-3,4-dihydro-6-fluoro-quinoxaline-2(1H)-one (0.023 g, 0.094 mmol, prepared as above) in $CF_3COOH$ (0.30 mL), excess fuming $HNO_3$ (0.015 mL) was added and the resulting red suspension was stirred overnight at 28° C. The red solution so obtained was cooled in an ice bath and diluted with water (2.0 mL). The precipitated solid was filtered, washed with water (2.0 mL) and dried in a drying pistol (toluene reflux) to yield 0.017 mg (60%) of the pure ($^1$H NMR) title compound as a brick red powder; m.p. 316–321° C.; $^1$H NMR (DMSO-$d_6$): δ 7.458 (d, 1H, J=6.3 Hz), 12.006 (br s, 1H), 12.178 (s, 1H); Elemental analysis for $C_8H_3BrFN_3O_4$, calcd: C, 31.60%; H, 0.99%; N, 13.82%, found: C, 31.78%; H, 0.84%; N, 13.49%.

Example 12

Preparation of 7-Bromo-6-methyl-5-nitro-1,4-dihydroquinoxaline-2,3-dione

2-Bromo-5-fluoro-4-nitrotoluene: To a stirred solution of 2-bromo-5-fluorotoluene (1.495 g, 7.909 mmol, Aldrich, used as received) in conc. $H_2SO_4$ (10.0 mL) at 0° C., $KNO_3$ (0.800 g, 7.91 mmol) was added in one lot. The resulting pale yellow solution was warmed to 28° C. and stirred overnight at 28° C. It was then poured into ice (50 g) and extracted with ethyl acetate (75 mL). The ethyl acetate was dried over anhydrous $Na_2SO_4$, removed under vacuum, and the resulting oil dried further under vacuum to afford 1.832 g (98%) of the title compound as an oil; $^1$H NMR (CDCl$_3$): δ 2.495 (s, 33H), 7.213 (d, 1H, $J_1$=11.4 Hz), 8.268 (d, 1H, $J_1$=7.2 Hz).

N-(4'-Bromo-5'-methyl-2'-nitrophenyl)glycine sodium salt: To a stirred solution of 2-bromo-5-fluoro-4-nitrotoluene (1.662 g, 7.102 mmol, as prepared above) in DMF (7.0 mL) at 70° C., was added, dropwise, a solution of sodium glycinate (0.690 g, 7.11 mmol, Aldrich, used as received) in water (7.0 mL). The resulting suspension was stirred overnight at 70° C. The suspension was cooled to room temperature and the red solid was filtered, washed with acetone, and dried under vacuum to give 0.932 g (45%) of the pure ($^1$H NMR) title compound as a red powder; $^1$H NMR (DMSO-$d_6$): δ 2.306 (s, 3H), 3.452 (d, 2H, J=3.9Hz), 6.874 (s, 1H), 8.125 (s, 1H), 8.779 (s, 1H).

7-Bromo-3,4-dihydro-6-methyl-quinoxaline-2(1H)-one: A solution of N-(4'-bromo-5'-methyl-2'-nitrophenyl)glycine sodium salt (0.200 g, 0.692 mmol, as prepared above) and tin (II) chloride dihydrate (0.468 g, 2.07 mmol, Aldrich, used as received) in ethanol (2.0 mL) was refluxed for 30 min. It was then cooled to room temperature. The precipitated solid was filtered and dried under vacuum to yield 0.064 g (38%) of the title compound as a yellow powder; $^1$NMR (DMSO-$d_6$): δ 2.130 (s, 3H), 3.674 (s, 2H), 6.120 (s, 1H), 6.583 (s, 1H), 6.868 (s, 1H), 10.284 (s, 1H).

7-Bromo-6-methyl-5-nitroquinoxaline-2(1H),3(4H)-dione: To a stirred suspension of 7-bromo-3,4-dihydro-6-methyl-quinoxaline-2(1H)-one (0.028 g, 0.012 mmol, prepared as above) in $CF_3COOH$ (0.30 mL), excess fuming $HNO_3$ (0.020 mL) was added and the resulting red solution was stirred overnight at 28° C. The suspension so obtained was cooled in an ice bath and diluted with water (2.0 mL). The precipitated solid was filtered, washed with water (2.0 mL) and dried in a drying pistol (toluene reflux) to yield 0.014 g (40%) of the pure ($^1$H NMR) title compound as a light yellow powder; m.p. >340° C.;$^1$H NMR (DMSO-$d_6$): δ 2.227 (s, 3H), 7.440 (s, 1H), 11.980 (s, 1H), 12.143 (s, 1H); Elemental analysis for $C_9H_6BrN_3O_4$ 0.45 $H_2O$ calcd C, 35.07%; H, 1.96%; N, 13.63%, found C, 35.44%; H, 1.92%; N, 13.23%.

Example 13

Preparation of 7-Chloro-6-fluoro-5-nitro-1,4-dihydroquinoxaline-2,3-dione

1-Chloro-2,4-difluoro-5-nitrobenzene: To a stirred solution of 1-chloro-2,4-difluorobenzene (0.829 g, 5.58 mmol, Aldrich, used as received) in conc. $H_2SO_4$ (8.0 mL) at 0° C., $KNO_3$ (0.565 g, 5.59 mmol) was added in one lot. The resulting solution was allowed to warm to 28° C. and stirred overnight at 28° C. It was then poured into ice (80 g) and extracted with ethyl acetate (75 mL). The ethyl acetate was dried over anhydrous $Na_2SO_4$, removed under vacuum, and the resulting oil was dried further under vacuum to afford 1.007 g (93%) of the pure ($^1$H NMR) title compound as a light red oil; $^1$H NMR (CDCl$_3$): δ 7.168 (dd, 1H, $J_1$=9.9 Hz, $J_2$=8.4 Hz), 8.238 (t, 1H, J=7.5 Hz).

N-(4'-Chloro-5'-fluoro-2'-nitrophenyl)glycine and N-(2'-chloro-5'-fluoro-4'-nitrophenyl)glycine sodium salt: To a stirred solution of 1-chloro-2,4-difluoro-5-nitrobenzene (1.000 g, 5.167 mmol, as prepared above) in DMF (10.0 mL), was added, dropwise, a solution of sodium glycinate (0.502 g, 5.17 mmol, Aldrich, used as received) in water (2.0 mL). The solution was stirred at 70° C. for 16 h and cooled to room temperature. The precipitated solid was filtered, washed with acetone (10 mL), and dried under vacuum to give 0.438 g (38%) of a red solid as a mixture of the title compounds in a ratio of 1.0:0.3 as judged by $^1$H NMR; $^1$H NMR (DMSO-d$_6$): δ 3.474 (d, 2H, J=4.5 Hz), 3.523 (d, 2H, J=3.9 Hz), 6.535 (d, 1H, J=14.7 Hz), 6.871 (d, 1H, J=12.3 Hz), 6.976 (s, 1H), 8.068 (d, 1H, J=7.8 Hz), 8.168 (d, 1H, J=7.8 Hz), 8.867 (s, 1H). The separation of the mixture was not feasible at this stage; hence, it was used as such for the next reaction.

7-Chloro-3,4-dihydro-6-fluoro-quinoxaline-2(1H)-one: A solution of a mixture of N-(4'-chloro-5'-fluoro-2'-nitrophenyl)glycine sodium salt and N-(2'-chloro-5'-fluoro-4'-nitrophenyl)glycine sodium salt (0.175 g, 0.704 mmol, as prepared above) and tin (II) chloride dihydrate (0.475 g, 2.11 mmol, Aldrich, used as received) in ethanol (3.5 mL) was refluxed for 30 min. It was then cooled to room temperature and the solvent was removed under vacuum. The residue was diluted with water (10 mL) and basified with saturated NaHCO$_3$ (3.0 mL) to pH~8. The resulting white suspension was extracted with ethyl acetate (30 mL). The ethyl acetate was dried over anhydrous Na$_2$SO$_4$ and removed under vacuum to yield 0.041 g (29%) of the pure ($^1$H NMR) title compound as a light yellow powder; m.p. 217–219° C. (decomposed); $^1$H NMR (DMSO-d$_6$): δ 3.745 (s, 2H), 6.37 (s, 1H), 6.587 (d, 1H, J=10.5 Hz), 6.741 (d, 1H, J=7.2 Hz), 10.331 (s, 1H).

7-Chloro-6-fluoro-5-nitroquinoxaline-2(1H),3(4H)-dione: To a stirred solution of 7-chloro-3,4-dihydro-6-fluoro-quinoxaline-2(1H)-one (0.024 g, 0.12 mmol, prepared as above) in CF$_3$COOH (0.40 mL), excess fuming HNO$_3$ (0.02 mL) was added and the resulting red solution was stirred overnight at 28° C. Solvent was removed under vacuum and the residue was diluted with water (2.0 mL). The precipitated solid was filtered, washed with water (1.0 mL), and dried in a drying pistol (toluene reflux) to yield 0.023 g (74%) of the pure ($^1$H NMR) title compound as a light yellow powder; m.p. 308–310° C.; $^1$H NMR (DMSO-d$_6$); δ 7.374 (d, 1H, J=6.9 Hz), 12.022 (br s, 1H), 12.221 (s, 1H); elemental analysis for C$_8$H$_3$ClFN$_3$O$_4$ calcd C, 37.02%; H, 1.16%; N, 16.19%; found C, 37.03%; H, 1.19%; N, 15.33%.

Example 14

Preparation of 6-Azido-7-fluoro-5-nitro-1,4-dihydroquinoxaline-2,3-dione

To a solid mixture of 23 mg (0.094 mmol) of 6,7-difluoro-5-nitroquinoxaline-2,3-dione and 7 mg (0.10 mmol) of sodium azide was added 0.5 mL of DMSO-d$_6$ and the mixture was shaken in a vortex for 10 s. Some white insoluble material was observed. One drop of D$_2$O was added and shaken for 10 s. Again, some white solid was observed. $^1$H NMR, 7.109 (1, d, J=12.0). The solution was added to 3 mL of ice-water. The yellow precipitate was filtered, washed with water, and dried to leave a yellow-solid (21 mg, 84%); mp 255–257° C.; $^1$H NMR (DMSO-d$_6$), 7.166 (1, d, J=11.8), 12.2–12.1 (m, 2). $^{19}$F NMR (C$_6$F$_6$ as reference, −162.9 ppm), −130.5 (mb). IR (KBr), 2154, 1753, 1540, 1359, 1308 cm$^{-1}$. MS, 266 (M$^+$, 1), 238 (M$^+$−N$_2$, 100), 178 (90), 150 (40).

Example 15

Preparation of 6-Amino-7-fluoro-5-nitro-1,4-dihydroquinoxaline-2,3-dione

To a solution of 20 mg (0.082 mmol) of 6,7-difluoro-5-nitro-1,4-dihydroquinoxaline-2,3-dione in 0.5 mL of DMSO-d$_6$ was added 2 drops of 30% ammonium hydroxide and the solution was heated at 80° C. for 24 h. To the mixture was added one more drop of 30% ammonium hydroxide and it was heated at 80° C. for 10 h. The mixture was added to 4 mL of water and then acidified with 2 N HCl to pH=1. The precipitate was filtered, washed with water, and dried to leave a yellow solid (15 mg, 76%); mp 250° C. (dec.); $^1$H NMR (DMSO-d$_6$), 7.202 (1, d, J=11.5), 7.232 (sb, 2), 11.15 (mb, 1), 12.0 (mb, 1). $^{19}$F NMR, −133.84 (d, J=11.6). MS, 240 (M$^+$, 100), 212 (10), 177 (10), 166 (20). HRMS, Calcd for C$_8$H$_5$FN$_4$O$_4$ 240.0290, found 240.0294.

Example 16

Preparation of 7-Fluoro-6-methoxy-5-nitro-1,4-dihydroquinoxaline-2,3-dione

To a solution of 21 mg (0.086 mmol) of 6,7-difluoro-5-nitro-1,4-dihydroquinoxaline-2,3-dione in 0.5 mL of DMSO-d$_6$ was added 16 mg (0.29 mmol) of sodium methoxide. The solution was shaken in a vortex for 10 s and kept at room temperature for 3 h. It was then added to 3 mL of water and acidified with 2 N HCl to pH=4. The precipitate was filtered, washed with water, and dried to leave a yellow solid (17 mg, 77%); mp 290–292° C.; $^1$H NMR (DMSO-d$_6$), 3.899 (s, 3), 7.163 (1, d, J=11.6), 11.97 (mb, 1), 12.137 (s, 1). $^{19}$F NMR, −134.48 (mb). MS, 255 (M$^+$, 100), 243 (15), 179 (16), 151 (40). HRMS, Calcd for C$_9$H$_6$FN$_3$O$_5$ 255.0287, found 255.0308.

Example 17

Preparation of 7-Fluoro-6-ethoxy-5-nitro-1,4-dihydroquinoxaline-2,3-dione

A solution of 24 mg (0.098 mmol) of 6,7-difluoro-5-nitro-1,4-dihydroquinoxaline-2,3-dione and 24 mg (0.33 mmol) of sodium ethoxide (96%) in 0.5 mL of DMSO-d$_6$ was kept at room temperature for 5 h. The red solution was added to 3 mL of water and acidified with 2 N HCl to pH=4. The precipitate was filtered, washed with water, and dried to leave a yellow solid (24 mg, 91%); mp 293–295° C.; $^1$H NMR (DMSO-d$_6$), 1.239 (t, 3, J=7.0), 4.141 (q, 2, J=7.2), 7.152 (1, d, J=11.7), 11.975 (s, 1), 12.135 (s, 1). $^{19}$F NMR, −134.06 (mb). MS, 269 (M$^+$, 90), 241 (100), 195 (70). HRMS, Calcd for C$_{10}$H$_8$FN$_3$O$_5$ 269.0443, found 269.0454.

Example 18

Preparation of 7-Fluoro-6-hydroxy-5-nitro-1,4-dihydroquinoxaline-2,3-dione

A mixture of 24 mg (0.098 mmol) of 6,7-difluoro-5-nitro-1,4-dihydroquinoxaline-2,3-dione and 19 mg (0.47 mmol)

of sodium hydroxide in 0.6 mL of $D_2O$ was heated at 105° C. for 24 h. The mixture was added to 2 mL of water and acidified with 2 N HCl to pH=1. The precipitate was filtered, washed with water, and dried to leave a red solid (19 mg, 80%); mp >360° C.; $^1$H NMR (DMSO-$d_6$), 7.101 (1, d, J=10.9), 11.10 (mb, 1), 11.70 (mb, 1), 11.99 (s, 1). $^{19}$F NMR, −137.4 (mb). MS 242 ($M^+$1, 100), 195 (50), 152 (20), 140 (25). HRMS, Calcd for $C_8H_4FN_3O_5$, 241.0131, found 241.0110.

Example 19

Preparation of 5-Azido-6,7-chloro-1,4-dihydroquinoxaline-2,3-dione

A mixture of 45 mg (0.18 mmol) of 5-amino-6,7-dichloro-1,4-dihydroquinoxaline-2,3-dione in 1 mL of concentrated $H_2SO_4$ (97%) was stirred in an ice-bath for 1 h. To the resulting yellow solution was added, dropwise, a solution of 70 mg (1.0 mmol) of $NaNO_2$ in 0.6 mL of $H_2O$ and the solution was stirred in an ice-bath for 3 h. To the resulting red solution was added a solution of 98 mg of $NaN_3$ in 0.6 mL of $H_2O$ and it was stirred for 1 h. To the mixture was added a solution of 101 mg of $NaN_3$ in 0.6 mL of $H_2O$ and the mixture was stirred overnight. The mixture was filtered, washed with water, and dried to leave a yellow solid 44 mg (88%); mp 130° C. (decomposed); $^1$H NMR (DMSO-$d_6$), 7.148 (s, 1), 11.75 (mb,1), 12.09 (s,1). IR (KBr), 2120, 1700 $cm^{−1}$.

Example 20

Preparation of 6-Azdo-5,7-dichloro-1,4-dihydroquinoxaline-2,3-dione

A mixture of 10 mg (0.040 mmol) of 6-amino-5,7-dichloro-1,4-dihydroquinoxaline-2,3-dione in 0.5 mL of concentrated $H_2SO_4$ (97%) was stirred in an ice-bath for 1 h. To the resulting yellow solution was added, dropwise, a solution of 30 mg (0.43 mmol) of $NaNO_2$ in 0.3 mL of $H_2O$ and the solution was stirred in an ice bath for 2 h. To the resulting red solution was added a solution of 40 mg of $NaN_3$ in 0.3 mL of $H_2O$ and it was stirred for 2 h. The mixture was diluted with 2 mL of $H_2O$ and stirred overnight. The mixture was filtered, washed with water, and dried to leave an almost colorless solid 10 mg (90%); mp 150° C. (decomposed); $^1$H NMR (DMSO-$d_6$), 7.153 (s,1), 11.602 (s,1), 12.02 (s,1). IR (KBr), 2127, 1720 $cm^{−1}$.

Example 21

Preparation of 6,7-Dimethyl-1,4-dihydroquinoxaline-2,3-dione

A mixture of 2.72 g (2.0 mmol) of 4,5-dimethyl-1,2-phenylenediamine and 1.92 g (21.3 mmol) of oxalic acid in 30 mL of 2N HCl was refluxed for 2.5 h and cooled to room temperature. The mixture was diluted with 20 mL of $H_2O$, filtered, washed with water, and dried to leave a pale-brown solid 3.57 g (94%); mp>250° C.; $^1$H NMR (DMSO-$d_6$), 2.161 (s,6), 6.869 (s,2), 11.78 (s,2).

Example 22

Preparation of 6,7-Dimethyl-5-nitro-1,4-dihydroquinoxaline-2,3-dione

To a solution of 1.90 g (10.0 mmol) of 6,7-dimethyl-1,4-dihydroquinoxaline-2,3-dione in 25 mL of $H_2SO_4$ (97%) kept in an ice bath was added dropwise 1.2 mL of $HNO_3$ (69–70%) and the solution was stirred at room temperature for 48 h. It was poured into 300 mL of ice-water and stirred for 10 min. The mixture was filtered, washed with water, and dried to leave a yellow solid 1.40 g (60%). The solid was purified by DMSO/$H_2O$ precipitation followed by NaOH/HCl precipitation to leave 0.85 g of a yellow solid; mp>250° C.; $^1$H NMR (DMSO-$d_6$), 2.079 (s,3), 2.246 (s,3), 7.048 (s,1), 11.770 (s,1), 12.030 (s,1). HRMS calcd. for $C_{10}H_9N_3O_4$ 235.0588; found 235.0584.

Example 23

Preparation of 7-Bromo-5-ethyl-1,4-dihydroquinoxaline-2,3-dione

A mixture of 1,2-diamino-4-bromo-6-ethylbenzene (40 mg, 0.14 mmol) and oxalic acid dihydrate (25 mg, 0.20 mmol, used as received) in 4 N HCl (1.5 mL) was refluxed at 120–5° C. for 3 h, then cooled to room temperature. The mixture was centrifuged and the liquid layer was removed. The yellow solid was washed with cold water (2×1 mL), collected by filtration, and dried at 60° C. under reduced pressure for 2 h, affording 40 mg of crude product (80%) as a yellow powder. The crude product was dissolved in 1N NaOH (2 mL) and filtered. The filtrate was acidified to pH=5, affording 12 mg of pure title compound; mp:>350° C. (dec. from 300° C.); IR (KBr, $cm^{−1}$):3410, 3164, 2919, 1740, 1705, 1600. $^1$H NMR (DMSO-$d_6$): δ 1.099 (t, 3 H, J=6 Hz), 2.741 (q, 2 H, J=7.2 Hz), 7.117 (d, 1 H, J=1.8 Hz), 7.138 (d, 1 H, J=1.8 Hz); 11.343 (s, 1H); 11.958 (s, 1H). HRMS: calcd for $C_{10}H_9BrN_2O_2$ ($M^+$) m/z: 267.9846; found 267.9853.

Example 24

Preparation of 5,7-Dimethyl-1,4-dihydro-2,3-quinoxalinedione 1,2-Diamino-4,6-dimethylbenzene. A mixture of 4,6-dimethyl-2-nitroaniline (1.66 g, 10.0 mmole) and 10% Pd/C (200 mg) in ethanol (35 mL) was hydrogenated for 2 h at room temperature under 25 psi $H_2$. The catalyst was removed by filtration with celite and the solvent was removed by rota-evaporation to give 1.300 g (96%) of 1,2-diamino-4,5-dimethylbenzene as a brown solid. $^1$H NMR ($CDCl_3$): 6.449 (s, 1 H), 6.469 (s, 1 H), 3.327 (br, 2 H), 3.259 (br, 2 H), 2.190 (s, 3 H), 2.159 (s, 3 H).

5,7-dimethyl-1,4-dihydro-2,3-quinoxalinedione. A mixture of 1,2-diamino-4,6-dimethylbenzene (424 mg, 3.11 mmole) and oxalic acid dihydrate (432 mg, 3.43 mmole, used as received) in 4N HCl (20 mL) was refluxed at 120–5° C. for 3 h, then cooled to room temperature. The mixture was centrifuged and the supernatant was removed. The yellow solid was washed with cold water (2×2 mL), collected by filtration, and dried in vacuo for 2 h, affording 516 mg of crude 5,7-dimethyl-1,4-dihydro-2,3-quinoxalinedione (87%) as a yellow powder. The crude product was taken up in 1 N NaOH (10 mL) and filtered. The filtrate was acidified to pH=3, affording the pure title compound (490 mg) as a light yellow powder; mp:345–347° C. (dec); IR (KBr, $cm^{−1}$):3460, 3.190, 2986, 1716, 1709, 1630. $^1$H NMR (DMSO-$d_6$): δ 11.858 (s, 1H), 11.173 (s, 1H), 6.766 (s, 1H), 6.745 (s, 1H), 2.280 (s, 3), 2.211 (s, 3). HRMS: calcd for $C_{10}H_{10}N_2O_2$ ($M^+$) m/z: 190.0714; found: 190.0744.

Example 25

Preparation of 1,4-Dihydrobenzo[g]quinoxaline-2,3-dione

A mixture of 603 mg (3.81 mmol) of 2,3-naphthalenediamine and 382 mg (4.24 mmol) of oxalic acid in 5 mL of 2N HCl was refluxed for 3 h and cooled to room temperature. The mixture was filtered, washed with water, and dried to leave a brown solid 803 mg (99%); mp>250° C.; $^1$H NMR (DMSO-d$_6$), 7.382 (dd, 2, J=3.16, 6.17), 7.525 (s, 2), 7.815 (dd, 2, J=3.22, 6.18), 12.088 (s, 2).

Example 26

Preparation of 5-Methyl-1,4-dihydro-2,3-quinoxalinedione

To a stirred solution of 2,3-diaminotoluene (0.498 g, 0.407 mmol, Aldrich) in 2 N HCl (6 mL, 12 mmol), oxalic acid dihydrate (0.520 g, 0.412 mmol, Fisher) was added in one portion. The resulting deep purple solution was refluxed for 13 h, to give a purple suspension. This was cooled to 25° C., filtered, washed with water (5 mL), and dried in vacuo (0.1 mm Hg) to give a purple powder. This was taken up in 2 N NaOH (25 mL, 50 mmol), giving a brown solution, which was filtered. The brown filtrate was acidified to pH 1.0 by addition of 2 N HCl (25 mL, 50 mmol), resulting in a tan suspension. Filtration of the suspension and washing of the filter cake with water (5 mL) gave the title compound as a tan powder (551 mg, 64%); mp 325° C. (the block was preheated to 320° C.); $^1$H NMR (DMSO-d$_6$) δ 2.26 (s, 3H), 6.86–7.01 (m, 3 H), 11.6 (broad, 2 H).

Example 27

Preparation of 6-Methyl-1,4-dihydro-2,3-quinoxalinedione

To a stirred solution of 3,4-diaminotoluene (0.302 g, 0.247 mmol, Aldrich) in 2 N HCl (4 mL, 8 mmol), oxalic acid dihydrate (0.330 g, 0.261 mmol, Fisher) was added in one portion. The resulting deep purple solution was refluxed for 13 h, to give a purple suspension. This was cooled to 25° C., filtered, washed with water (5 mL), and dried in vacuo (0.1 mm Hg) to give a blue-grey powder. This was taken up in 2 N NaOH (34 mL, 68 mmol), giving a brown solution, which was filtered. The brown filtrate was acidified to pH 1.0 by addition of 2 N HCl (42 mL, 84 mmol), resulting in a tan suspension. Filtration of the suspension and washing of the filter cake with water (mL) gave the title compound as a grey powder (225.5 mg, 43%); mp 318° C. (the block was preheated to 300° C.); $^1$H NMR (DMSO-d$_6$) δ 2.32 (s, 3 H), 6.90–6.99 (m, 3H), 11.22 (s, 1H), 11.90 (s, 1H).

Example 28

Preparation of 7-Methyl-5-nitro-1,4-dihydro-2,3-quinoxalinedione

5-Methyl-3-nitro-1,2-phenylenediamine. The procedure of Gillespie et al., *J. Org. Chem.* 25:942 (1960) was adopted as follows. A dark black solution of 4-methyl-2,6-dinitroaniline (0.100 g, 0.561 mmol, Aldrich, used as received) in 6.66% aq. (NH$_4$)$_2$S (3.3 mL, prepared from 20% aq.(NH$_4$)$_2$S solution supplied by Aldrich) and ethanol (3.5 mL) was refluxed for 45 min. It was then cooled to 28° C. and the solvents were removed as much as possible under vacuum (inside the hood to avoid the stench of ammonium sulfide). The slurry so obtained was diluted with water (10 mL) and the resulting red solid was filtered and dried under vacuum to obtain 0.072 g (85%) solid as a red powder, which was used as such for the next reaction. $^1$H NMR (acetone-d$_6$): 2.205 (s, 3H), 6.342 (br s, 2H), 6.622 (s, 1H), 7.571 (s, 1H).

7-Methyl-5-nitro-1,4-dihydro-2,3-quinoxalinedione. A suspension of 5-methyl-3-nitro-1,2-phenylenediamine (0.050 g, 0.30 mmol) and oxalic acid (0.038 g, 0.30 mmol) in 2N HCl (1.6 mL) was refluxed for 2.5 h during which time it first formed a solution and then a suspension. The suspension was then cooled to 28° C. and the precipitated solid was filtered, washed with water (5 mL), and dried under vacuum to afford 30 mg (45%) of product as a light yellow powder. It was purified by the base-acid treatment as follows. All of the crude product was taken up in 1N NaOH (3.3 mL) and swirled at 90° C. to dissolve most of the solid. It was then filtered hot and the filtrate was cooled in an ice-bath and acidified with concentrated HCl to pH~2. The precipitated solid was filtered and dried under vacuum to obtain 0.025 g (38%) of the pure title compound as a light yellow powder; m.p. 319°–323° C. (decomposed); $^1$H NMR (DMSO-d$_6$): 2.352 (s, 3H), 7.271 (s, 1H), 7.75 (s, 1H), 11.044 (s, 1H), 12.299 (s, 1H); elemental analysis for C$_9$H$_7$N$_3$O$_4$.0.35 H$_2$O calcd: C, 47.52%; H, 3.10%; N, 18.47%; found: C, 47.82%; H, 3.03%; N, 18.06%.

Example 29

Preparation of 7-Fluoro-6-methyl-5-nitro-1,4-dihydro-2,3-quinoxalinedione 2,5-Difluoro-nitrotoluene. To a stirred solution of 2,5-difluorotoluene (0.544 g, 4.25 mmol, Aldrich, used as received) in conc. H$_2$SO$_4$ (5.0 mL) at 0° C., KNO$_3$ (0.430 g, 4.25 mmol) was added in one portion. The resulting pale yellow solution was warmed to 28° C. and stirred at that temperature overnight. It was then poured into ice (25 g) and extracted with ethyl acetate (40 mL). The extract was dried over Na$_2$SO$_4$ and evaporated to afford 0.555 g (91%) of the title compound as a light red oil; $^1$H NMR (CDCl$_3$): 2.369 (d, 3H, J=1.8 Hz), 7.127 (dd, 1H, J$_1$=8.1 Hz, J$_2$=6.0 Hz), 7.734 (dd, 1H, J$_1$=8.4 Hz, J$_2$=6.3 Hz).

N-(4-Fluoro-5-methyl-2-nitrophenyl)glycine sodium salt. To a stirred solution of 2,5-difluoro-4-nitrotoluene (0.550 g. 3.18 mmol) in DMF (5.0 mL) was added dropwise a solution of sodium glycinate (0.308 g, 3.18 mmol, Aldrich, used as received) in water (1.0 mL). The resulting suspension was stirred at 28° C. overnight. The solid was filtered and dried under vacuum to give 0.168 g (23%) of crude product. It was purified as follows. 0.150 g material was boiled in ethyl acetate (5.0 mL) and filtered while hot to give 0.134 g (18%) of the pure ($^1$H NMR) title compound as a yellow powder. $^1$H NMR (DMSO-d$_6$): 2.213 (s, 3H), 3.428 (d, 2H, J=3.9 Hz), 6.765 (d, 1H, J=6.9 Hz), 7.700 (d, 1H, J=10.5 Hz), 8.728 (s, 1H).

7-Fluoro-3,4-dihydro-6-methylquinoxaline-2(1H)-one. A mixture of N-(4-fluoro-5-methyl-2-nitrophenyl)glycine sodium salt (0.125 g, 0.548 mmol) and tin (II) chloride dihydrate (0.370 g, 1.64 mmol, Aldrich, used as received) in ethanol (3.0 mL) was refluxed for 30 min. It was then cooled to room temperature and the solvent was removed under vacuum. The residue was diluted with water (4.0 mL) and basified with saturated NaHCO$_3$ to pH~8. The resulting suspension was extracted with ethyl acetate (30 mL). The extract was dried over Na$_2$SO$_4$ and evaporated to yield 0.032 g of the title compound as a yellow powder, which was used for the next reaction; $^1$H NMR (DMSO-d$_6$): 2.024 (s, 3H), 3.607 (s, 2H), 5.751 (s, 1H), 6.453 (d, 1H, J=9.9 Hz), 6.456 (d, 1H, J=8.1 Hz), 10.162 (s, 1H).

7-Fluoro-6-methyl-5-nitro-1,4-dihydro-2,3-quinoxalinedione. To a stirred solution of 7-fluoro-3,4-dihydro-6-methylquinoxaline-2(1H)-one (0.023g, 0.094 mmol) in CF$_3$COOH (0.30 mL), excess fuming HNO$_3$ (0.020 mL) was added and the resulting red suspension was stirred overnight at 28° C. The red solution so obtained was cooled in an ice bath and diluted with water (2.0 mL). The precipitate was filtered, washed with water (2.0 mL), and dried in a drying pistol (toluene reflux) to yield 0.020 g (66%) of the pure title compound as a yellow powder; m.p. 308–311° C.; $^1$H NMR (DMSO-d$_6$): 2.106 (s, 3H), 7.058 (d, 1H, J=9.9 Hz), 11.769 (bs, 1H), 12.172 (s, 1H).

Example 30

Preparation of 6-Chloro-5-cyano-7-nitro-1,4-dihydroquinoxaline-2,3-dione

To a stirred solution of 2,6-dichloro-3-nitrobenzonitrile (3.935 g, 18.13 mmol, Lancaster, used as received) in DMF (25 mL) at 70° C., an aqueous solution of sodium glycinate (1.760 g, 18.13 mmol, Aldrich, used as received) in water (25.0 mL) was added dropwise. The resulting solution was stirred at 70° C. for 48 h. The suspension was cooled to room temperature and the precipitated yellow solid was filtered, washed with chloroform (20 mL), and dried under vacuum to furnish 2.020 g (44%) of pure ($^1$H NMR) N-(3'-chloro-2'-cyano-6'-nitro)phenylglycine as a yellow powder. $^1$H NMR (DMSO-d$_6$): δ 3.888 (d, 2H, J=3.9 Hz), 6.857 (d, 1H, J=9.0 Hz). 8.283 (d, 1H, J=9.3 Hz), 9.572 (s, 1H).

A suspension of N-(3'-chloro-2'-cyano-6'-nitro) phenylglycine (2.000 g, 7.824 mmol, as prepared above) and tin (II) chloride dihydrate (6.000 g, 26.59 mmol, Aldrich, used as received) in ethanol (40 mL) was refluxed for 30 min. The resulting suspension was cooled to room temperature and the solid was filtered, washed with ethanol (20 mL), and dried under vacuum to give 1.261 g (78%) of pure ($^1$H NMR) 6-chloro-5-cyano-3,4-dihydroquinoxaline-2(1H)-one as a light yellow solid. $^1$H NMR (DMSO-d$_6$): δ 3.668 (s, 2H), 6.719 (d, 1H, J=8.4 Hz), 6.843 (d, 1H, J=8.1 Hz), 6.912 (s, 1H), 10.682 (s, 1H).

To a suspension of 6-chloro-5-cyano-3,4-dihydroquinoxaline-2(1H)-one (0.096 g, 0.46 mmol, as prepared above) in CF$_3$COOH (1.0 mL), fuming nitric acid (0.40 mL) was added so that it formed a dark red solution. (A lesser amount of fuming nitric acid created a suspension that gave a mixture of partially oxidized and fully oxidized products). The resulting solution was then stirred overnight at room temperature. The volatiles were removed under vacuum and the residue was diluted with water (3.0 mL). The yellow solid was filtered, washed with water (2.0 mL), and dried under vacuum to furnish 0.090 g (73%) of the pure ($^1$H NMR) title compound as a yellow powder; m.p. 327–331° C.; $^1$H NMR (DMSO-d$_6$): δ 7.950 (s, 1H), 12.381 (s, 1H); IR (KBr, cm$^{-1}$): 3501, 3452,3157, 2259, 1740, 1712, 1635, 1607, 1550, 1396, 1340; elemental analysis for C$_9$H$_3$ClN$_4$O$_4$ calcd: C, 40.55%; H, 1.13%; N, 21.02%; found C, 40.57%; H, 1.11%; N, 20.84%.

Example 31

Preparation of 5-Cyano-6,7-dichloro-1,4-dihydroquinoxaline-2,3-dione

A suspension of 6-chloro-5-cyano-7-nitroquinoxaline-2(1H),3(4H)-dione (0.100 g, 0.38 mmol, as prepared above) and tin (II) chloride dihydrate (0.508 g, 2.25 mmol, Aldrich) in ethanol (4.0 mL) was refluxed for 24 h. The resulting suspension was then cooled to room temperature and the yellow solid was filtered, washed with ethanol (2.0 mL), and dried under vacuum to obtain 0.078 g (88%) of 7-amino-6-chloro-5-cyanoquinoxaline-2(1H),3(4H)-dione as a yellow powder; $^1$H NMR (DMSO-d$_6$): δ 5.762 (br s, 2H), 6.818 (s, 1H), 11.69 (s, 1H), 12.03 (s, 1H).

To a stirred solution of 7-amino-6-chloro-5-cyanoquinoxaline-2(1H),3(4H)-dione (0.035 g, 0.15 mmol, as prepared above) in concentrated HCl (1.5 mL) at 0° C., an aqueous solution of NaNO$_2$ (0.060 g, 0.87 mmol) in water (0.20 mL) was added and the resulting turbid solution was stirred in an ice bath for 2 h. A solution of CuCl (0.100 g, 1.01 mmol) in concentrated HCl (1.0 mL) was added to it while cooling the flask in an ice bath. Instant evolution of N$_2$ ensued and the resulting dark green suspension was stirred at 0° C. for 2 h. Water (1.0 mL) was added to it followed by stirring overnight at room temperature. To the light green suspension so formed, water (4.0 mL) was added with further stirring at room temperature for 1 h. The precipitated solid was filtered, washed with water (2.0 mL), and dried under vacuum to furnish 0.029 g (77%) of the title compound as a cream colored solid; m.p. 327–335° C. (decomposed); $^1$H NMR (DMSO-d$_6$): δ 7.463 (d, 1H, J=1.2 Hz), 12.306 (s, 2H). The coupling of aromatic signal disappeared upon addition of 3 drops of methanol-d$_4$ indicating that the aromatic proton had coupled with peri N—H proton; IR (KBr, cm$^{-1}$); 3574, 3479, 2237, 1737, 1710, 1392, 1271, 1183.

Example 32

Preparation of 7-Chloro-6-methoxy-5-nitro-1,4-dihydroquinoxaline-2,3-dione

To a stirred solution of 7-Chloro-6-fluoro-5-nitroquinoxaline-2(1H),3(4H)-dione (0.100 g, 0.385 mmol, as prepared above) in DMSO (1.0 mL) at room temperature, sodium methoxide (0.125 g, 2.31 mmol, Mallinckrodt) was added in one portion. The resulting dark red solution was stirred overnight at room temperature. It was then diluted with water (5.0 mL) and acidified with concentrated HCl (6 drops) to pH~2. The precipitated solid was filtered, washed with water (5.0 mL), and dried under vacuum to obtain 0.116 g (110%) of pure ($^1$H NMR) title compound as a yellow powder; m.p. darkens at 316° C.; $^1$H NMR (DMSO-d$_6$): δ 3.821 (s, 3H), 7.275 (s, 1H), 12.079 (s, 1H) 12.121 (s, 1H). The NMR also indicates the presence. of DMSO (reaction solvent).

Example 33

Preparation of 6,7-Dimethoxy-1,4-dihydroquinoxaline-2,3-dione (10)

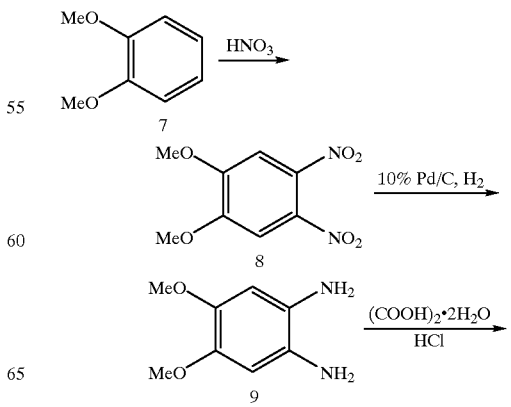

-continued

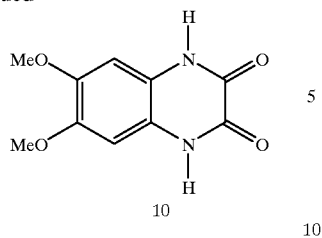

4,5-Dimethoxy-1,2-dinitrobenzene (8). The procedure of Wulfman and Cooper, *Synthesis* 924 (1978), was adopted for this reaction. 1,2-Dimethoxybenzene 7 (20.8 g, 0.15 mol; Aldrich) was added dropwise over 30 min. to vigorously stirred 70% nitric acid (175 mL) under nitrogen. The temperature was kept below 50° C. during the addition. Shortly after the addition was complete, a yellow solid precipitated. The mixture was then heated to 70–80° C. for about 2 h (until evolution of $NO_2$ ceased). The mixture was allowed to cool below 40° C., then poured into ice/water (1000 mL) and filtered by suction filtration. The yellow solid was slurried in saturated sodium bicarbonate (500 mL) overnight. The crude product was isolated by suction filtration and then purified by recrystallization from ethyl alcohol (1000 mL). The title compound was obtained as fine yellow needles (23 g, 67%). mp 128–130° C. (lit. mp 127–128° C.; Frisch and Bogert, *J. Org. Chem.* 8:331 (1943)) $^1$H NMR ($CDCl_3$, 300 MHz) δ 4.016 (s, 6H), 7.337 (s, 2H).

6,7-Dimethoxy-1,4-dihydroquinoxaline-2,3-dione (10). 4,5-Dimethoxy-1,2-dinitrobenzene 8 (912 mg, 4.00 mmol) was dissolved in ethyl acetate (30 mL). To this solution was added 10% Pd/C (228 mg, 20%; Aldrich). The mixture was then stirred at room temperature under a pressure of 40 psi ($H_2$) for 14 hr. The catalyst was removed through a column of Celite (5 g) and washed with ethyl acetate (3×15 mL) under nitrogen. The filtrates were combined and the solvent was removed to give the diamine 9 as a nearly colorless solid. The $^1$H NMR spectrum was consistent with the assigned structure. Diamine 9 was dissolved in 4 N hydrochloric acid (7 mL), and oxalic acid dihydrate (504 mg, 4.00 mmol; Fisher) was added to this solution in one portion with stirring under $N_2$. The mixture was refluxed at 130–5° C. (oil bath) for 3 hr. A yellow solid precipitated, which was collected by suction filtration and dried in vacuo overnight, giving 725 mg (82% based on compound 8) of the title compound as a pale yellow solid; mp 345–346° C.; $^1$H NMR ($CDCl_3$, 300 MHz) δ 3.677 (s, 3H), 6.681 (s, 2H), 11.695 (s, 2H). EIMS m/e 222 (100, M+). (HPLC purity 99%).

Example 34

Preparation of 6,7-Methylenedioxy-1,4-dihydroquinoxaline-2,3-dione (15)

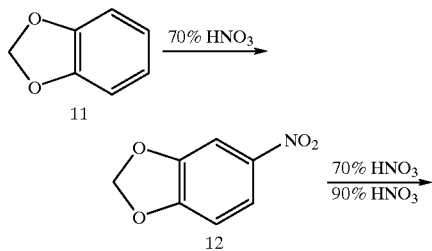

-continued

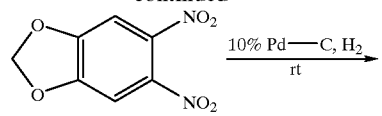

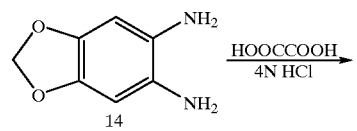

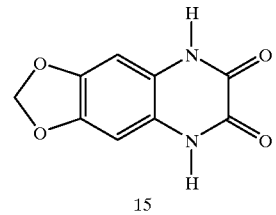

4,5-Methylenedioxynitrobenzene (12). 1,3-Benzodioxole (13.33 g, 109 mmol; Aldrich) was added dropwise to stirred, cold (−5–0° C.) concentrated nitric acid (150 mL) at a rate such that the temperature did not rise above 0° C. over 90 min. in an ice-salt bath. After the addition was complete, the mixture was stirred at 0° C. for another 3 hr and was then poured into ice/water (750 mL). The product was isolated by filtration, washed with cold water until the washings were no longer acidic (6×50 mL), and then with saturated aqueous sodium bicarbonate (50 mL), giving 17.23 g (95%) of the title compound as a yellow solid; mp 147–148° C. (lit. mp 147° C.; Perkin et al., *J. Chem. Soc.* 94:1979 (1909)); $^1$H NMR ($CDCl_3$, 300 MHz) δ 6.142 (s, 2H), 6.868 (d, 1H, J=8.4 Hz), 7.667 (d, 1H, J=1.5 Hz), 7.894 (d, 1H, J=6.9 Hz).

4,5-Methylenedioxy-1,2-dinitrobenzene (13). 4,5-Methylenedioxynitrobenzene 12 (17.23 g, 103 mmol) was ground to a fine powder and added in one portion to a stirred mixture of 70% (conc.) nitric acid (125 mL; Baker) and 90% (fuming) nitric acid (125 mL; Baker) at −15° C. Stirring was continued at −5° C. to 0° C. for another 3 hr. The mixture was then poured into ice/water (1250 mL). The product was isolated by filtration, washed with cold water until the washings are no longer acidic (6×50 mL), and then with saturated aqueous sodium bicarbonate (50 mL), giving 19.1 g (87%) of the title compound as a yellow solid. Mp 99–100° C. (lit. mp 101° C.; Hughes and Ritchie, *Aust. J. Chem.* 7:104 (1954)) $^1$H NMR ($CDCl_3$, 300 MHz) δ 6.270 (s, 2H), 7.303 (s, 2H).

6,7-Methylenedioxy-1,4-dihydroquinoxaline-2,3-dione (15). 4,5-Methylenedioxy-1,2-dinitrobenzene 13 (1.37 g, 6.47 mmol) was dissolved in ethyl acetate (20 mL). To this solution was added 10% Pd/C (343 mg, 20%; Aldrich). The mixture was then stirred at room temperature under a pressure of 40 psi ($H_2$) for 14 hr. The catalyst was removed through a column of Celite (5 g) and washed with ethyl acetate (3×15 mL) under nitrogen. The filtrates were combined and the solvent was removed to give the diamine 14 as a nearly colorless solid. The $^1$H NMR spectrum was consistent with the assigned structure. Diamine 14 was dissolved in 4 N hydrochloric acid (7 mL), and oxalic acid dihydrate (983 mg, 6.47 mmoL) was added to this solution in one portion with stirring under $N_2$. The mixture was refluxed at 130–5° C. (oil bath) for 3 hr. A yellow,solid precipitated, which was collected by suction filtration and dried in vacuo overnight, giving 1.18 g (88.7% based on compound 13) of the title compound as a brown solid;

mp>360° C.; ¹H NMR (DMSO-d₆, 300 MHz) δ 5.998 (s, 2H), 6.775 (s, 2H), 11.695 (s, 2H). EIMS m/e 206 (100, M+). (HPLC purity 98%).

Example 35

Preparation of 6,7-diethyl-5-nitro-1,4-dihydroquinoxaline-2,3-dione (26)

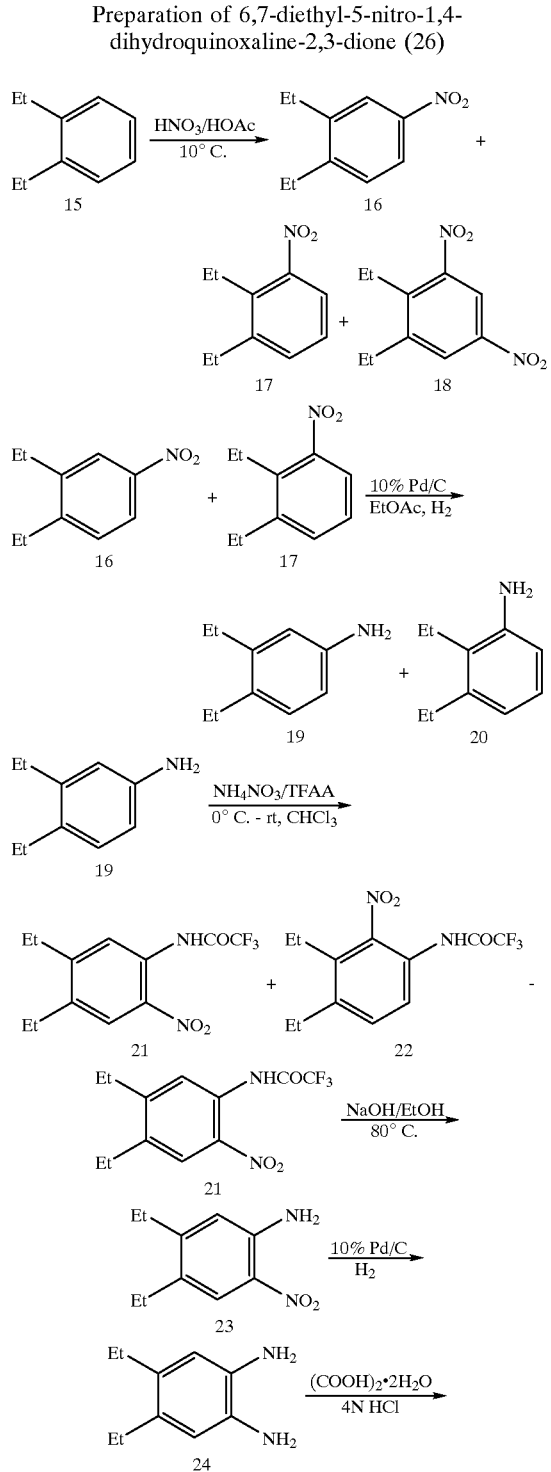

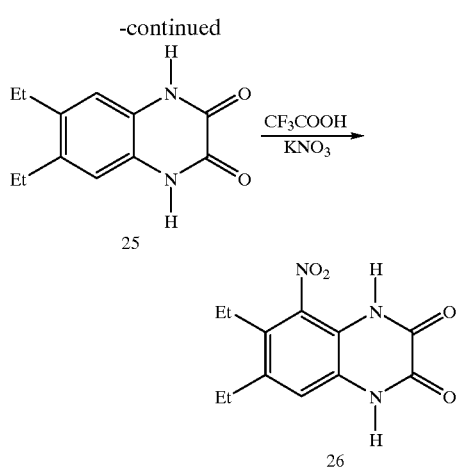

1,2-Diethyl-4-nitrobenzene (16), 1,2-Diethyl-3-nitrobenzene (17), and 4,5-Diethyl-1,3-dinitrobenzene (18). The procedure of Lambooy, J. P., *J. Am. Chem. Soc.* 71:3756 (1949) was adopted for this reaction. A mixture of fuming nitric acid (8.75 mL; Baker) and glacial acetic acid (4.5 mL) was cooled to 10° C. To this mixture, 1,2-diethylbenzene 15 (2.5 g, 18.6 mmol; Aldrich) was added dropwise at such a rate as to maintain the temperature at 10–20° C. with vigorous stirring over 30 min. After the addition was complete, the reaction was allowed to stir at 15° C. for another 1 h. The reaction mixture was then poured into ice-water (50 mL). The nitro compounds were extracted with ether (4×20 mL). The combined ether extract was washed with water (3×7.5 mL), 10% sodium hydroxide aqueous solution (2×8 mL), and water (2×7.5 mL). The ether extract was dried over sodium sulfate. The solvent was evaporated to give a residue, which was purified by preparative TLC (Hexanes: EtOAc=8:2), giving the mono-nitro compounds 16 and 17 (1.90 g, 57%) as a yellow oil ($R_f$=0.8), accompanied by the dinitro compound 18 (0.30 g, 7%) as a brown oil ($R_f$=0.5). ¹H NMR (CDCl₃, 300 MHz): δ (16): 1.220 (t, 6H, J=7 Hz), 2.725 (q, 4H, J=7 Hz), 7.728 (d, 1H, J=6 Hz), 7.986 (d, 1H, J=6 Hz), 8.034 (s, 1H). (17): 1.220 (t, 6H, J=7 Hz), 2.725 (q, 4H, J=7 Hz), 7.242 (m, 1H), 7.378 (d, 1H, J=7.5 Hz), 7.550 (d, 1H, J=7.5 Hz). (18): 1.231 (t, 6H, J=7 Hz), 2.655 (q, 4H, J=7 Hz), 8.044 (s, 1H), 10.636 (s, 1H).

3,4-Diethylaniline (19) and 2,3-Diethylaniline (20). A mixture of 1,2-diethyl-4-nitrobenzene (16) and 1,2-diethyl-3-nitrobenzene (17) (1.4 g, 7.82 mmol) was dissolved in ethyl acetate (20 mL). To this solution was added 10% Pd—C (350 mg, 20%; Aldrich). The mixture was agitated at room temperature under a pressure of 35 psi (H₂) for 10 h. The catalyst was removed through a column of Celite (5 g) and washed with ethyl acetate (3×15 mL). The filtrates were combined and evaporated in vacuo to give a residue, which was separated by preparative TLC (Hexanes: EtOAc=8:2), giving 3,4-diethylaniline (19) (0.822 g, 71%) as a pale yellow oil ($R_f$=0.7) and 2,3-diethylaniline (20) (0.219 g, 19%) as a brown oil ($R_f$=0.6). ¹H NMR (CDCl₃, 300 MHz): δ (19): 1.184 (t, 6H, J=7 Hz), 2.573 (q, 4H, J=7 Hz), 3.456 (br, s, 2H) 6.513 (m, 2H), 6.970 (d, 1H, J=7.8 Hz). (20): 1.215 (t, 6H, J=7 Hz), 2.617 (q, 4H, J=7 Hz), 6.570 (d, 1H, J=7.5 Hz), 6.650 (d, 1H, J=7.5 Hz), 6.973 (m, 1H).

4,5-Diethyl-2-nitrotrifluoroacetylanilide (21) and 3,4-diethyl-2-nitrotrifluoroacetylanilide (22). Into a 15-mL, single-necked, round-bottomed flask equipped with a magnetic stirrer, reflux condenser, and drying tube were added 3,4-diethylaniline 19 (0.822 g, 5.52 mmol), ammonium nitrate (0.456 g, 5.70 mmol; Baker), and trifluoroacetic anhydride (5 mL, 35.0 mmol; Sigma). To this mixture was added chloroform (10 mL) at 0° C. under $N_2$ with stirring. The mixture was allowed to stir at room temperature for 2.5 h. The mixture was poured into ice (20 g), extracted with chloroform (3×20 mL), and dried over sodium sulfate. The solvent was removed by aspirator to give a residue, which was separated by preparative TLC (Hexanes: EtOAc=8:2), giving 4,5-diethyl-2-nitrofluoroacetylanilide (21) (0.898 g, 56%) as a yellow solid; mp 58–60° C.; and 3,4-diethyl-2-nitrotrifluoroacetylanilide (22) (0.30 g, 18%) as a brown solid, mp 70–72° C.

$^1$H NMR (CDCl$_3$, 300 MHz): δ (21): 1.275 (m, 6H), 2.742 (m, 4H), 8.099 (s, 1H), 8.539 (s, 1H), 11.375 (s, 1H); (22): 1.262 (m, 6H), 2.661 (m, 4H), 7.420 (d, 1H, J=8.7 Hz), 7.915 (d, 1H, J=8.7 Hz), 8.742 (s, 1H).

4,5-Diethyl-2-nitroaniline (23). To a solution of 4,5-diethyl-2-nitrotrifluoroacetylanilide (21) (0.898 g, 3.1 mmol) in absolute alcohol (30 mL) was added 10% sodium hydroxide aqueous solution (10 mL). The solution was stirred at 80° C. (oil bath) for 4 h. Ethanol was evaporated in vacuo to leave an orange solid, which was collected by suction filtration, washed with water (3×15 mL), and dried in vacuo, giving 567 mg (95%) of the title compound 23 as an orange solid; mp 63–65° C. (lit. mp 64–65° C.; Lambooy, J. P., *J. Am. Chem. Soc.* 71:3756 (1949)); $^1$H NMR (CDCl$_3$, 300 MHz) δ 1.242 (m, 6H), 2.568 (m, 4H), 5.846 (br, s, 2H), 6.593 (s, 1H), 7.899 (s, 1H).

4,5-Diethyl-1,2-diaminobenzene (24). 4,5-Diethyl-2-nitroaniline (23) (567 mg, 2.92 mmol) was dissolved in ethyl acetate (20 mL). To this solution was added 10% Pd—C (142 mg, 20%; Aldrich). The mixture was agitated at room temperature under a pressure of 35 psi (H$_2$) for 5 h. The catalyst was removed through a column of Celite (5 g) and washed with ethyl acetate (3×20 mL). The filtrates were combined and evaporated in vacuo to give 4,5-diethyl-1,2-diaminobenzene 24 (459 mg, 96%) as a colorless solid; mp 114–116° C. (lit. mp 114–115° C.; Lambooy, J. P., *J. Am. Chem. Soc.* 71:3756 (1949)); $^1$H NMR (CDCl$_3$, 300 MHz) δ 1.158 (t, 6H, J=7.5 Hz), 2.498 (q, 4H, J=7.5 Hz), 2.908 (br, s, 4H), 6.555 (s, 2H).

6,7-Diethyl-1,4-dihydroquinoxaline-2,3-dione (25). 4,5-Diethyl-1,2-diaminobenzene 24 (459 mg, 2.80 mmol) was dissolved in 4 N hydrochloric acid (12 mL) at 90° C. Oxalic acid dihydrate (983 mg, 6.47 mmoL) was added to this solution in one portion with stirring under $N_2$. The mixture was refluxed at 130–5° C. (oil bath) for 3 h. A yellow solid precipitated, which was collected by suction filtration and dried in vacuo overnight, giving 538 mg (88%) of the title compound 25 as a brown solid; mp>360° C.; $^1$H NMR (DMSO-d$_6$, 300 MHz) δ 1.092 (t, 6H, J=7.5 Hz), 2.510 (q, 4H, J=7.5 Hz), 6.867 (s, 2H), 11.742 (s, 2H). EIMS m/e 218 (95, M$^+$), 203 (100, M$^+$—CH$_3$). (HPLC purity 100%).

5-Nitro-6,7-diethyl-1,4-dihydroquinoxaline-2,3-dione (26). 6,7-Diethyl-2,3-quinoxalinedione 25 (218 mg, 1.0 mmol) was added to trifluoroacetic acid (8 mL; Sigma). To this suspension was added potassium nitrate (121.2 mg, 1.2 mmol; Baker) in one portion with stirring under $N_2$. The reaction was stirred at room temperature for 48 h. Trifluoroacetic acid was evaporated in vacuo to give a residue. Water (10 mL) was added to this residue with vigorous stirring. A yellow solid precipitated, which was collected by suction filtration and dried in vacuo to give 182 mg (69%) of the title compound 26 as a yellow solid; mp 270–272° C. (dec.); $^1$H NMR (DMSO-d$_6$, 300 MHz) δ 1.137 (m, 6H), 2.622 (m, 4H), 7.088 (s, 1H), 11.762 (s, 1H), 12.028 (s, 1$^1$H). EIMS m/e 263 (100, M$^+$). (HPLC purity 100%).

Example 36

Preparation of 5-Nitrocyclopento[g]-1,4-dihydroquinoxaline-2,3-dione

5-Acetamidoindan. To a solution of 5.2 g (39 mmol) of 5-aminoindan in 15 mL of dioxane kept in an ice-bath was added dropwise 8 mL (8.6 g, 84 mmol) of acetic anhydride. The solution was stirred at room temperature for 16 h. It was diluted with 70 mL of water. The mixture was filtered, washed with water, and dried to leave a gray solid 6.21 g (91%). $^1$H NMR (CDCl$_3$), 2.069 (m, 2), 2.165 (s, 3), 2.879 (m, 4), 7.20 (mb, 1), 7.145 (s, 2), 7.441 (s, 1).

5-Acetamido-6-nitroindan. To a solution of 5.59 g (31.9 mmol) of 5-acetamidoindan in 55 mL of H$_2$SO$_4$ kept in an ice-bath was added portionwise 3.62 g of KNO$_3$ (35.8 mmol). The solution was stirred in the ice-bath for 2 h and at room temperature overnight. It was added to 500 mL of ice-water and stirred for 1 h. The precipitate was filtered, washed with water, and dried to leave a black solid, which was separated by chromatography (silica gel, eluted with hexane/ethyl acetate=10:1) to give 1.06 g (15%) of a yellow solid. $^1$H NMR (CDCl$_3$), 2.142 (m, 2), 2.279 (s, 3), 3.00 (m, 4), 8.44 (s, 1), 8.575 (s, 1), 10.389 (s, 1).

5-Amino-6-nitroindan. A mixture of 259 mg (1.16 mmol) of 5-acetamido-6-nitroindan in 4 mL of 2 N HCl was heated at 85° C. for 9 h and cooled to room temperature. The solid precipitate was filtered, washed with water, and dried to leave 201 mg (97%) of a crystalline yellow solid. $^1$H NMR (CDCl$_3$), 2.068 (m, 2), 2.843 (m, 4), 6.00 (sb, 2), 6.650 (s, 1), 7.942 (s, 1).

5,6-Diaminoindan. A solution of 200 mg (1.12 mmol) of 5-amino-6-nitroindan and 1.14 g (6.01 mmol) of SnCl$_2$ in 8 mL of ethanol was heated at 70° C. for 2 h. It was evaporated to remove the ethanol. The residue was treated with 40% aqueous NaOH to pH=12. The mixture was diluted with 4 mL of water and extracted with CHCl$_3$ (3×10 mL). The extract was dried (MgSO$_4$) and evaporated to leave a yellow crystalline solid (162 mg, 97%). $^1$H NMR (CDCl$_3$), 2.012 (m, 2), 2.773 (t, 4, J=7.25), 3.301 (sb, 4), 6.614 (s, 2).

Cyclopento[g]-1,4-dihydroquinoxaline-2,3-dione. A mixture of 162 mg (1.09 mmol) of 5,6-diaminoindan and 108 mg (1.20 mmol) of oxalic acid in 3 mL of 2N HCl was refluxed for 3 h and cooled to room temperature. The mixture was filtered, washed with water, and dried to leave an almost colorless solid (187 mg, 85%); mp>360° C.; $^1$H NMR (DMSO-d$_6$), 1.985 (m, 2), 2.808 (t, 4, J=7.28), 6.957 (s, 2), 11.833 (s, 2). MS, 202 (M$^+$, 100), 173 (90), 145 (10), 130 (20). HRMS, Calc. for C$_{11}$H$_{10}$N$_2$O$_2$ 202.0738, found 202.0747.

5-Nitro-cyclopento[g]-1,4-dihydroquinoxaline-2,3-dione. To a stirred mixture of 84 mg (0.41 mmol) of cyclopento [g]-1,4-dihydroquinoxaline-2,3-dione in 3 mL of CF$_3$CO$_2$H was added in one portion 44 mg (0.43 mmol) of KNO$_3$. The mixture was stirred at room. temperature for 14 h and the resulting red solution was evaporated. The residue was diluted with water (4 mL). The mixture was filtered, washed with water, and dried to leave a yellow solid (74 mg, 73%). $^1$H NMR (DMSO-d$_6$), 2.040 (m, 2), 2.926 (t, 2, J=7.5), 3.085 (t, 2, J=7.5), 7.259 (s, 1), 11.175 (s, 1), 12.233 (s, 1).

Example 37

Preparation of 7-Fluoro-6-(n-butoxy)-5-nitro-1,4-dihydroquinoxaline-2,3-done (28)

To a mixture of 25 mg (1.0 mmol) of NaH and 50 mg (0.67 mmol) of n-butanol was added 1.5 mL of DMSO and the mixture was stirred for 1 h. To the resulting solution was added 27 mg (0.11 mmol) of 6,7-difluoro-5-nitroquinoxaline-2,3-dione (27) and the solution was stirred at room temperature for 5 days. The solution was diluted with 3 mL of water and acidified with 2 N HCl to pH=1. The precipitate was filtered, washed with water, and dried to leave 11 mg (33%) of a yellow solid; mp 290–292° C.; $^1$H NMR (DMSO-d$_6$), 0.882 (t, 3, J=7.4), 1.360 (m, 2), 1.595 (m, 2), 4.084 (t, 2, J=6.3), 7.151 (1, d, J=11.54), 11.98 (m, 1), 12.12 (m, 1), MS, 297 (M$^+$, 20), 241 (100), 195 (20). HRMS, Calcd for C$_{12}$H$_{12}$FN$_3$O$_5$ 297.0755; found 297.0757.

Example 38

Preparation of 7-Fluoro-6-(3-phenylpropoxy)-5-nitro-1,4-dihydroquinoxaline-2,3-dione (29)

Compound 29 was prepared in a manner similar to that of compound 28. From 25 mg (1.0 mmol) of NaH, 61 mg (0.44 mmol) of 3-phenylpropanol and 28 mg (0.11 mmol) of 6,7-difluoro-5-nitroquinoxaline-2,3-dione (27) in 2 mL of DMSO was obtained 25 mg (63%) of a yellow solid; mp 280–282° C.; $^1$H NMR (DMSO-d$_6$), 1.923 (m, 2), 2.653 (t, 2, J=7.8), 4.103 (t, 2, J=6.1), 7.135–7.306 (m, 6), 11.98 (m, 1), 12.131 (s, 1). $^{19}$F NMR, -133.87 (mb). MS, 359 (M$^+$, 20), 243 (15), 119 (40), 91 (100). NRMS, Calcd for C$_{17}$H$_{14}$FN$_3$O$_5$ 359.0911; found 359.0927.

Example 39

Preparation of 6-Chloro-7-ethyl-5-nitro-1,4-dihydroquinoxaline-2,3-dione (37)

3-Ethyl-5-nitroanaline (30). To 160 mL of concentrated H$_2$SO$_4$ stirred at room temperature was added 24.5 g (0.20 mol) of 2-ethylaniline. The resulting solution was kept in an acetone-ice bath (−10 to −5° C.) and 10.5 mL (15.75 g, 0.225 mol) of fuming HNO$_3$ (d=150, >90% HNO$_3$) in 20 mL of concentrated H$_2$SO$_4$ was added dropwise. The solution was stirred in the acetone-ice bath for 30 min after addition of HNO$_3$ and then allowed to warm to room temperature. It was poured into 1,000 mL of ice, whereupon the mixture was neutralized by ammonium hydroxide (30%) to pH=8. The mixture was stirred for 1 h, filtered, washed with water, and dried to leave 32.2 g (97%) of red solid. Recrystallization with 100 mL of absolute alcohol yielded 25.8 g of a yellow solid; mp 60–61° C. (Lambooy & Lambooy, *J. Med. Chem.* 16:765–770 (1973): 63–64° C.); $^1$H NMR (CDCl$_3$), 1.128 (t, 3, J=7.5), 2.565 (q, 2, J=7.6), 3.915. (sb, 2), 7.177 (d, 1, J=8.2), 7.502 (d, 1, J=2.2), 7.582 (dd, 1, J=2.2, 8.3).

3-Chloro-4-ethylnitrobenzene (31). A mixture of 8.3 g (50 mmol) of 30 in 40 mL of concentrated HCl and 40 mL of H$_2$O was heated at 80° C. for 1 h. The mixture was cooled in an ice bath and a solution of 3.6 g (52 mmol) of NaNO$_2$ in 6 mL of H$_2$O was added dropwise. The solution was stirred in an ice bath for 1 h after addition of NaNO$_2$. The solution was added dropwise to a stirred solution of 10 g (102 mmol) of CuCl in 40 mL of concentrated HCl kept in an ice bath. The mixture was stirred in the ice bath for 1 h after addition of the diazonium solution and extracted with CHCl$_3$ (3×40 mL). The extract was dried (MgSO$_4$) and evaporated to leave 9.2 g (99%) of pale-red oil. $^1$H NMR (CDCl$_3$), 1.276 (t, 3, J=7.5), 2.851 (q, 2, J=7.5), 7.408 (d, 1, J=8.5), 8.064 (dd, 1, J=2.0, 8.4), 8.227 (d, 1, J=2.0).

3-Chloro-4-ethylaniline (32). A solution of 8.9 g (48 mmol) of 31 and 54.6 g (241 mmol) of SnCl$_2$.2H$_2$O in 100 mL of absolute alcohol was refluxed for 1 h. It was evaporated to remove most of the solvent and the residue was treated with 2N NaOH to pH=9. The mixture was filtered and the solid was washed with methanol (10 mL) and ethyl acetate (200 mL). The filtrate was separated and the aqueous phase was extracted with ethyl acetate (2×50 mL). The combined organic solution was dried (MgSO$_4$) and evaporated to leave 7.31 g (98%) of liquid. $^1$H NMR (CDCl$_3$), 1.178 (t, 3, J=7.5), 2.639 (q, 2, J=7.4), 6.532 (dd, 1, J=2.2, 8.1), 6.700 (d, 1, J=2.2), 6.996 (d, 1, J=8.2).

4-Chloro-5ethyl-2-trifluoracetamidonitrobenzene (33). To 25 mL of (CF$_3$CO)$_2$O kept in an ice bath was added dropwise 2.56 g (16.4 mL) of 32 and the resulting mixture was stirred at room temperature for 1 h. To the mixture, kept in the ice bath, was added in portion 1.72 g (17.0 mmol) of KNO$_3$ and the resulting solution was stirred in the ice bath for 1 h and at room temperature overnight. The solution was added to 100 mL of ice-water yielding a precipitate that was filtered, washed with water, and dried to give a pale-yellow solid. It was crystallized with absolute alcohol (30 mL) to give 2.55 g (52%) of a colorless solid; mp 82–83° C.; $^1$H NMR (CDCl$_3$), 1.293 (t, 3, J=7.5), 2.825 (q, 2, J=7.7), 8.197 (s, 1), 8.805 (s, 1), 11.35 (mb, 1).

3-Chloro-4-ethyl-6-nitroaniline (34). A mixture of 1.4 g (4.7 mmol) of 33 and 10 mL of 7% K$_2$CO$_3$ in methanol/H$_2$O (3:2) was stirred at room temperature for 2 h. It was diluted with 15 mL of water, filtered, washed with water, and dried to leave 691 mg (73%) of a yellow solid; mp 100–101° C.; (Lit. 104–106° C. Lambooy & Lambooy, supra). $^1$H NMR (CDCl$_3$), 1.228 (t, 3, J=7.5), 2.665 (q, 2, J=7.5), 5.957 (sb, 2), 6.859 (s, 1), 7.995 (s, 1).

Ethyl-N-(3-chloro-4-ethyl-6-nitrophenyl) Glycinate (35). A mixture of 200 mg (1.0 mmol) of 34, 140 mg of K$_2$CO$_3$, and 2 mL of ethyl bromoacetate was heated at 130° C. for 3 days. The mixture was cooled to room temperature, diluted with 10 mL of 1 N NaOH, and stirred at room temperature for 4 h. The mixture was acidified with 2 N HCl to pH=1, filtered, washed with water, and dried to leave 280 mg (97%) of a yellow solid. $^1$H NMR (DMSO-d$_6$), 1.144 (t, 3, J=7.4), 1.213 (t, 3, J=7.1), 2.620 (q, 2, J=7.4), 4.165 (q, 2, J=7.1), 4.271 (d, 2, J=5.8), 7.042 (s, 1), 8.034 (s, 1), 8.281 (s, 1).

6-Chloro-7-ethyl-3,4-dihydroquinoxaline-2-one (36). A solution of 280 mg (0.977 mmol) of 35, 950 mg (4.21 mmol) of SnCl$_2$.2H$_2$O, and 8 mL of absolute alcohol was refluxed for 4 h and cooled to room temperature. It was evaporated and the residue was treated with 1 N NaOH to pH=10. The mixture was filtered, washed with water, and dried to leave a solid. The solid was stirred with 15 mL of ethyl acetate and filtered. The filtrate was evaporated to leave 137 mg (66%) of solid. $^1$H NMR (DMSO-d$_6$), 1.080 (t, 3, J=7.4), 2.503 (q, 2, J=7.2), 3.700 (s, 2), 6.036 (s, 1), 6.632 (s, 6.662 (s, 1), 10.281 (s, 1).

6-Chloro-7-ethyl-5-nitro-1,4-dihydroquinoxaline-2,3-dione (37). To a solution of 137 mg (0.65 mmol) of 36 in 4 mL of CF$_3$CO$_2$H kept in an ice bath was added dropwise 0.4 mL of fuming HNO$_3$. The solution was stirred in the ice bath for 1 h and at room temperature overnight. It was evaporated and the residue was treated with 6 mL of water and stirred for 10 min. The mixture was filtered, washed with water, and dried to leave a yellow solid, 140 mg (80%); mp>330° C.; $^1$H NMR (DMSO-d$_6$), 1.161 (t, 3, J=7.4), 2.712 (q, 2, J=7.6), 7.192 (s, 1), 12.209 (mb, 2). MS, 269 (M$^+$, 100), 254 (12), 226 (15), 160 (20). HRMS, Cacld for C$_{10}$H$_8$ClN$_3$O$_4$ 269.0198; Found 269.0196.

Example 40

Preparation of 6-Chloro-7-ethyl-1,4-dihydroquinoxaline-2,3-dione (39)

1,2-diamino-4-chloro-5-ethylbenzene (38). A solution of 271 mg (1.35 mmol) of 34 and 1.24 g (5.49 mmol) of SnCl$_2$.2H$_2$O, in 5 mL of absolute alcohol was refluxed for 2 h. It was evaporated and the residue was treated with 1 N NaOH to pH=10. The mixture was extracted with CH$_2$Cl$_2$ (3×10 mL). The extract was dried (MgSO$_4$) and evaporated to leave 229 mg (99%) of a yellow solid. $^1$H NMR (CDCl$_3$), 1.165 (t, 3, J=7.5), 2.594 (q, 2, J=7.2), 6.560 (s, 1), 6.696 (s, 1).

6-Chloro-7-ethyl-1,4-dihydroquinoxaline-2,3-dione (39). A mixture of 228 mg (1.33 mmol) of 38 and 124 mg (1.38 mmol) of oxalic acid in 4 mL of aqueous 2N HCl was refluxed for 4 h. It was cooled to room temperature, filtered, and dried to leave 275 mg (92%) of a brown solid; mp>400° C.; $^1$H NMR (DMSO-d$_6$), 1.134 (t, 3, J=7.4), 2.635 (q, 2, J=7.4), 7.026 (s, 1), 7.107 (s, 1), 11.890 (s, 1), 11.927 (s, 1). MS, 224 (M$^+$, 100), 209 (45), 181 (80). HRMS, Cacld for C$_{10}$H$_9$ClN$_2$O$_2$ 224.0348; Found 224.0359.

Example 41

Preparation of 6-Chloro-7-ethyl-5-nitro-1,4-dihydroquinoxaline-2,3-dione (37) and 7-Chloro-6-ethyl-5-nitro-1,4-dihydroquinoxaline-2,3-dione (40)

To a mixture of 232 mg (103 mmol) of 39 in 6 mL of CF$_3$CO$_2$H kept in an ice bath was added 113 mg of KNO$_3$ portionwise. The mixture was stirred in the ice bath for 1 h and at room temperature overnight. To the solution was added 28 mg of KNO$_3$ and it was stirred overnight. It was evaporated and the residue was treated with 10 mL of water, filtered, washed with water, and dried to leave 227 mg (81%) of a yellow solid. $^1$H NMR (DMSO-d$_6$), (37): 1.14 (m, 3), 2.712 (q, 2, J=7.4), 7.193 (s, 1), 12.209 (mb, 2). and (40): 1.14 (m, 3), 2.582 (q, 2, J=7.4), 7.303 (s, 1), 12.0 (mb, 1), 12.17 (mb, 1). 37:40=1:1.

Example 42

Preparation of 6-Chloro-7-fluoro-5-trifluoromethyl-1,4-dihydroquinoxaline-2,3-dione (41)

A mixture of 25 mg (0.095 mmol) of 6-amino-7-fluoro-5-trifluoromethyl-quinoxaline-2,3-dione (29) in 1.0 mL of concentrated HCl was stirred in an ice-bath for 1 h. To the resulting solution was added dropwise a solution of 40 mg (0.58 mmol) of NaNO$_2$ in 0.1 ml of H$_2$O and the solution was stirred in an ice-bath for 4 h. To the solution was added dropwise a solution of 60 mg of CuCl in 0.3 mL of 6 N HCl. The resulting mixture was stirred in an ice-bath for 4 h and at room temperature overnight. The mixture was diluted with 1 mL of H$_2$O and stirred for 10 min. followed by another 1 mL of H$_2$O with stirring for another 10 min. It was filtered, washed with water, and dried to leave 21 mg (78%) of a pale-yellow solid; mp 323–325° C.; $^1$H NMR (DMSO-d$_6$), 7.337 (d, 1, J=9.34), 10.95 (mb, 1), 12.309 (s, 1). MS, 282 (M$^+$, 100), 254 (20), 234 (80), 207 (40). HRMS, Cacld for C$_9$H$_3$ClF$_4$N$_2$O$_2$ 281.9816; Found 281.9833.

Example 43

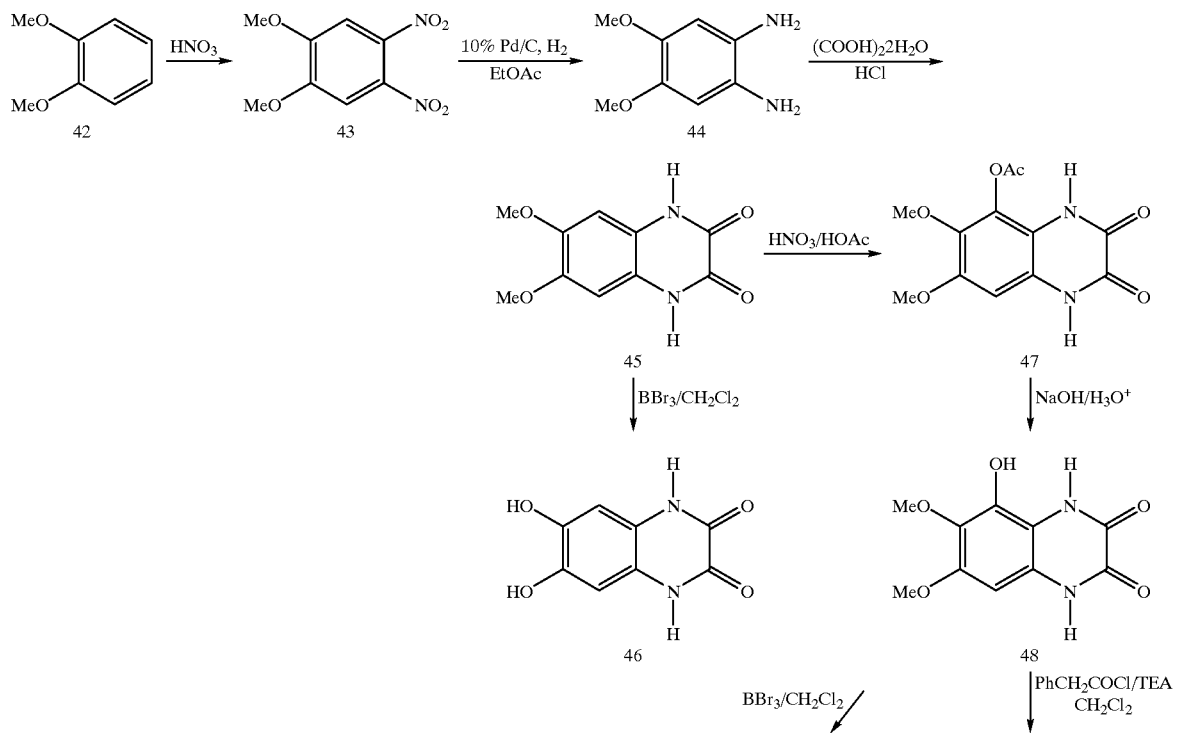

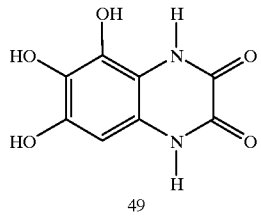

49

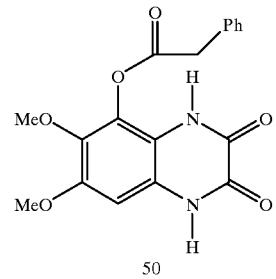

50

4,5-Dimethoxy-1,2-dinitrobenzene (43). The procedure of Wulfman and Cooper, Synthesis 1978:924 was adopted for this reaction. 1,2-Dimethoxybenzene 42 (20.8 g, 0.15 mol; Aldrich) was added dropwise over 30 min. to vigorously stirred 70% nitric acid (175 mL) under nitrogen. The temperature was kept below 50° C. during the addition. Shortly after the addition was complete, a yellow solid precipitated. The mixture was then heated to 70–80° C. for about 2 h (until evolution of $NO_2$ ceased). THe mixture was allowed to cool below 40° C. and was then poured into ice/water (1,000 mL) and filtered by suction filtration. The yellow solid was slurried in saturated sodium bicarbonate (500 ml) overnight. The crude product was isolated by suction filtration and then purified by recrystallization from ethyl alcohol (1,000 mL). The title compound was obtained as fine yellow needles (23 g, 67%); mp 128–130° C. (lit. mp 127–128° C.); $^1$H NMR (CDCl$_3$, 300 MHz) δ 4.016 (s, 6 H), 7.337 (s, 2 H).

6,7-Dimethoxy-2,3-quinoxalinedione (45) (from 43, two steps). 4-5-Dimethoxy-1,2-dinitrobenzene (43) (912 mg, 4.00 mmol) was dissolved in ethyl acetate (30 mL). To this solution was added 10% Pd/C (228 mg, 20%; Aldrich). The mixture was then stirred at room temperature under a pressure of 40 psi (H$_2$) for 14 hr. The catalyst was removed through a column of Celite (5 g) and washed with ethyl acetate (3×15 mL) under nitrogen. The extracts were combined and the solvent was removed to give the diamine (44) as a nearly colorless solid. The $^1$H NMR spectrum was consistent with the assigned structure. Diamine (44) was dissolved in 4 N hydrochloric acid (7 mL), and oxalic acid dihydrate (504 mg, 4.00 mmol; Fisher) was added to this solution in one portion with stirring under N$_2$. The mixture was refluxed at 130–5° C. (oil bath) for 3 hr. A yellow solid precipitated, which was collected by suction filtration and dried in vacuo overnight, yielding 725 mg (82% based on compound 43) of the title compound as a pale yellow solid; mp 345–346° C.; $^1$H NMR (DMSO-d$_6$, 300 MHz) δ 3.677 (s, 3 H), 6.681 (s, 2 H), 11.695 (s, 2 H). EIMS m/e 222 (100, M$^+$). (HPLC purity 99%).

6,7-Dihydroxy-2,3-quinoxalinedione (46). To a suspension of 6,7-dimethoxy-2,3-quinoxalinedione (45) (222 mg, 1.0 mmol) in 2 mL of methylene dichloride was added 5 mL of a solution of boron tribromide in methylene dichloride (1 M, Aldrich). The resulting mixture was stirred at room temperature for 24 hr. The mixture was then poured into ice-water (10 g) to form a suspension. Aquous sodium hydroxide (20%, 10 mL) was added to the suspension to form a red solution. The solution was acidified with 6 N HCl (10 mL) to pH=1. The suspension was centrifuged, washed with methanol, and dried in vacuo, giving 170 mg (88%) of the product as a brown solid; mp>350° C.; $^1$H NMR (DMSO-d$_6$, 300 MHz) δ 6.541 (s, 2 H), 8.989 (s, 2 H), 11.543 (s, 2 H). EIMS m/e 194 (100, M$^+$). (HPLC>99%).

5-Acetoxy-6,7-diethoxy-2,3-quinoxalinedione (47). 6,7-Dimethoxy-2,3-quinoxalinedione (45) (222 mg, 1.0 mmol) was dissolved in glacial acetic acid (10 mL) at 100° C. (oil bath). The oil bath was removed and fuming nitric acid (53 μL, 1.2 mmol; Baker) was added dropwise to the solution. The reaction mixture was then stirred at room temperature for 24 h. The mixture was filtered and washed with water to give a white solid, giving 150 mg (54%) of the title compound; mp 321–322° C.; $^1$H NMR (DMSO-d$_6$, 300 MHz) δ 2.300 (s, 3 H), 3.619 (s, 3 H), 3.746 (s, 3 H), 6.661 (s, 1 H), 11.700 (s, 1 H), 11.832 (s, 1 H). EIMS m/e 280 (M$^+$, 30), 238 (100). Anal. Calcd for $C_{12}H_{12}N_2O_6$: C, 51.43; H, 4.32; N, 10.00. Found: C, 51.29; H, 4.04; N, 9.90. (HPLC purity>99%).

5-Hydroxy-6,7-dimethoxy-2,3-quinoxalinedione (48). 5-Acetyloxy-6,7-dimethoxy-2,3-quinoxalinedione (47) (30 mg, 0.107 mmol) was added to a single-necked 15-mL flask. Sodium hydroxide aqueous solution (2 N, 1 mL) was added to the flask under nitrogen with stirring. The solution was then stirred at room temperature for 24 h. The solution was diluted with water (3 mL) and then acidified with HCl (4 N, 1 mL) to pH=2 to give a brown solid, which was collected by filtration and dried in vacuo, giving 23 mg (86%) of the title compound; mp 285–286° C. (dec); $^1$H NMR (DMSO-d$_6$, 300 MHz) δ 3.688 (s, 3 H), 3.694 (s, 3 H), 6.227 (s, 1 H), 9.769 (s, 1 H), 11.016 (s, 1 H), 11.658 (s, 1 H). EIMS m/e 238 (100, M$^+$), HPLC purity>96%.

5,6,7-Trihydroxy-2,3-quinoxalinedione (49). To a suspension of 5-hydroxy-6,7-dimethoxy-2,3-quinoxalinedione (48) (50 mg, 0.22 mmol) in 2 mL of methylene dichloride was added 2 mL of a solution of boron tribomide in methylene dichloride (1 M, Aldrich). The resulting mixture was stirred at room temperature for 12 hr. The mixture was poured into ice-water (5) to form a suspension. Aqueous sodium hydroxide (20%, 2 mL) was added to the suspension to form a red solution. Then the solution was acidified with 6 N HCl (5 mL) to pH=1. The suspension was centrifuged, washed with methanol, and dried in vacuo giving 37 mg (80%) of the product as a brown solid; mp>350° C.; $^1$H NMR (DMSO-d$_6$, 300 MHz) δ 6.149 (s, 1 H), 9.113 (s, 1 H), 9.190 (s, 2 H), 10.713 (s, 1 H), 11.501 (s, 1 H) (HPLC>98%).

5-(2-Phenylacetyloxy)-6,7-dimethoxy-2,3-quinoxalinedione (50). To a suspension of 5-hydroxy-6,7-dimethoxy-2,3-quinoxalinedione (48) (50 mg, 0.22 mmol) in 3 mL of methylene dichloride was added 0.14 mL of triethylamine and phenylacetyl chloride (77.5 mg, 0.5 mmol, Aldrich) at 0° C. The resulting mixture was stirred at room temperature for 12 hr. The reaction mixture was then poured into ice-water (5 g). A white solid precipitated and was collected by suction filtration, washed with water (3×5 mL) and ethyl acetate (3×2 mL), and dried in vacuo, giving 60 mg (77%) of the product as a white solid; mp 298–300° C.; $^1$H NMR (DMSO-d$_6$, 300 MHz) δ 3.405 (s, 3 H), 3.728 (s, 3 H), 4.024 (s, 2H), 6.653 (s, 1 H), 7.359 (m, 5 H), 11.773 (s, 1 H), 11.846 (s, 1 H). EIMS m/e 356 (25, M$^+$), 238 (100). (HPLC 100%).

Example 44

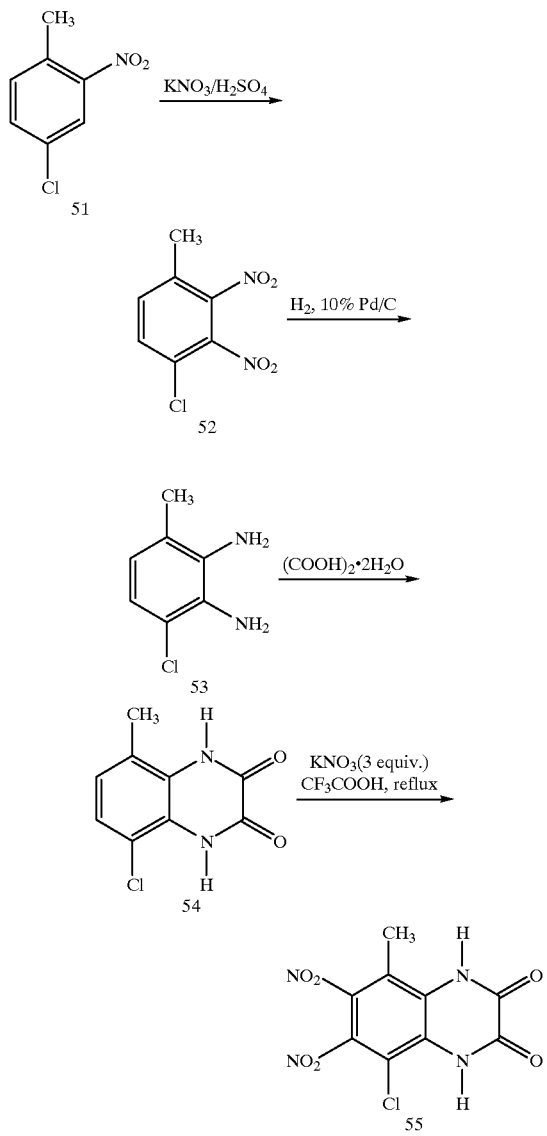

4-Chloro-2,3-dinitrotoluene (52). 4-Chloro-2-nitrotoluene 51 (1.716 g, 10 mmol; Aldrich) was dissolved in 10 mL of concentrated sulfuric acid. To this solution was added potassium nitrate (1.212 g, 12 mmol; Baker). The resulting mixture was stirred at 80° C. for 12 hr. The mixture was poured into ice-water (20 g). The precipitate was collected by suction filtration and dried in vacuo, giving 2 g of a mixture of three isomers. After flash chromatography, 0.519 g of the desired 4-chloro-2,3-dinitrotoluene (52) ($R_f$= 0.36 Hexanes: Ethyl acetate=7:3) was obtained in 24% yield; mp 78–80° C.; $^1$H NMR (CDCl$_3$, 300 MHz) δ 2.475 (s, 3 H), 7.445 (d, 1 H, J=8.4 Hz), 7.610 (d, 1 H, J=8.4 Hz).

5-Chloro-8-methyl-2,3-quinoxalinedione (54) (from 52 two steps). 4-Chloro-2,3-dinitrotoluene (52) (519 mg, 2.4 mmol) was dissolved in ethyl acetate (6 mL). To this solution was added 10% Pd/C (130 mg, 20%; Aldrich). The mixture was then stirred at room temperature under a pressure of 60 psi (H$_2$) for 8 hr. The catalyst was removed through a column of Celite (5 g) and washed with ethyl acetate (3×15 mL) under nitrogen. The extracts were combined and the solvent was removed to give the diamine 53 as a brown oil. The $^1$H NMR spectrum was consistent with the assigned structure. Diamine 53 was dissolved in 4 N hydrochloric acid (8 mL), and oxalic acid dihydrate (260 mg, 2.05 mmol; Fisher) was added to this solution in one portion with stirring under N$_2$. The mixture was refluxed at 130–5° C. (oil bath) for 6 hr. A brown solid came out that was collected by suction filtration and dried in vacuo overnight, giving 320 mg (63% based on compound 53) of the title compound as a brown solid; mp>350° C.; $^1$H NMR (DMSO-d$_6$, 300 MHz) δ 2.288 (s, 3 H), 6.915 (d, 1 H, J=8.4 Hz), 7.080 (d, 1 H, J=8.4 Hz), 11.230 (s, 1 H), 11.277 (s, 1 H). EIMS m/e 210 (100, M$^+$). (HPLC purity 96%).

5-Chloro-6,7-dinitro-8-methyl-2,3-quinoxalinedione (55). To the suspension of 5-chloro-8-methyl-2,3-quinoxalinedione (54) (180 mg, 0.855 mmol) in trifluoroacetic acid (4 mL) was added potassium nitrate (259 mg, 2.56 mmol). The resulting mixture was allowed to reflux for 24 hr. Trifluoroacetic acid was evaporated in vacuo. Water (3 mL) was added and the solid was collected by suction filtration and dried in vacuo, giving 200 mg (78%) of the product as a pale yellow solid; mp 346–348° C.; $^1$H NMR (DMSO-d$_6$, 300 MHz) δ 2.340 (s, 3 H), 11.898 (s, 1 H), 12.070 (s, 1 H). EIMS m/e 300 (20, M$^+$, $^{35}$Cl), 149 (100). (HPLC>97%).

Example 45

Preparation of 6-Chloro-1,4-dihydro-7-fluoro-5-nitroquinoxaline-2,3-dione

1-Chloro-2,5-difluoro-4-nitrobenzene. To a stirred solution of 1-chloro-2,5-difluorobenzene (0.770 g, 5.18 mmol) in concd H$_2$SO$_4$ (8.0 mL) at 0° C., KNO$_3$ (0.525 g, 5.19 mmol) was added in one lot. The resulting yellow solution was allowed to warm to room temperature and stirred overnight at room temperature. It was then poured into ice (80 g) and extracted with ethyl acetate (75 mL). The ethyl acetate was dried over anhydrous Na$_2$SO$_4$, removed under vacuum and the residue was dried further under vacuum to afford 0.845 g (85%) of title compound as a yellow liquid; $^1$H NMR (CDCl$_3$) δ 7.43 (dd, 1 H, J$_1$=9.6 Hz, J$_2$=6.0 Hz), 7.93 (t, 1 H, J=7.2 Hz).

N-(5'-chloro-4'-fluoro-2'-nitrophenyl)glycine sodium salt. To a stirred solution of 1-chloro-2,5-difluoro-4-nitrobenzene (0.825 g, 4.26 mmol) in ethanol (8.0 mL), was added a solution of sodium glycinate (0.415 g, 4.27 mmol) in water (1.5 mL). The resulting suspension was refluxed for 60 h. The solution was cooled to room temperature and the precipitated bright orange solid was filtered, washed with cold ethanol (5 mL), and dried under vacuum to give 0.673 g (64%) title compound as a bright orange powder; $^1$H NMR (DMSO-d$_6$) δ 3.50 (d, 2H, J=3.6 Hz), 7.04 (d, 1H, J=6.6 Hz), 8.01 (d, 1H J=9.9 Hz), 8.74 (s, 1H). The unreacted 1-chloro-2,5-difluoro-4-nitrobenzene was recovered almost quantitatively from the filtrate.

6-Chloro-3,4-dihydro-7-fluoro-quinoxaline-2(1H)-one. A suspension of N-(5'-chloro-4'-fluoro-2'-nitrophenyl)glycine sodium salt (0.650 g, 2.61 mmol) and tin (II) chloride dihydrate (1.770 g, 7.845 mmol) in ethanol (10.5 mL) was refluxed for 1 h. It was then cooled to room temperature and ~5 mL ethanol was removed under vacuum. The precipitated solid was collected by filtration under vacuum, washed with ethanol (3 mL) and dried to obtain 0.311 g (59%) title compound as an off-white powder; $^1$H NMR (DMSO-d$_6$) δ 3.69 (s, 2H), 6.08 (s, 1H), 6.65 (d, 1H, J=9.9 Hz), 6.71 (d, 1H, J=7.2 Hz), 10.39 (s, 1H). The solvent from the filtrate was removed under vacuum. The residue was diluted with water (15.0 mL) and the pH was adjusted with 10% Na$_2$CO$_3$ to ~9. The resulting suspension was extracted with ethyl acetate (50 mL). The ethyl acetate was dried over anhydrous Na$_2$SO$_4$ and removed under vacuum to yield further 0.118 g (22%) of pure ($^1$H NMR) title compound for a combined yield of 81%.

6-Chloro-1,4-dihydro-7-flouro-5-nitroquinoxaline-2,3-dione. To a stirred suspension of 6-chloro-3,4-dihydro-7-flouro-quinoxaline-2(1H)-one (0.140 g, 0.698 mmol) in TFA (3.0 mL), excess fuming HNO$_3$ (0.20 mL) was added and the resulting red solution was stirred overnight at room temperature. The resulting yellow suspension was poured into ice-water (15.0 mL). The precipitated solid was collected by vacuum filtration, washed with water (5.0 mL) and dried in a drying pistol (toluene reflux) to yield 0.124 g (69%) pure (HPLC) title compound as a yellow powder; $^1$H NMR (DMSO-d$_6$) δ 7.21 (d, 1H, J=9.3 Hz), 12.20 (s, 1H), 12.30 (s, 1H).

Example 46

Preparation of 7-Chloro-1,4-dihydro-6-ethyl-5-nitroquinoxaline-2,3-dione 2,5-Dichloro-1-ethylbenzene. A suspension of mossy zinc (10 g) and mercuric chloride (0.5 g) in concd HCl (0.5 mL) and water (5 mL) was shaken for ~5 min. The aqueous layer was then decanted. To the residue was added coned HCl (7.5 mL) and water (7.5 mL) followed by 2',5'-dichloroacetophenone (3.106 g, 16.43 mmol) and the suspension was refluxed for 4 h during which time, hourly addition of concd HCl (90.5 mL) was carried out. The resulting suspension was cooled to room temperature and the aqueous layer was decanted. The residual solid was washed with ether (3×30 mL). The aqueous layer was extracted with ether (3×50 mL). The combined ether layer was washed with brine, dried over anhydrous Na$_2$SO$_4$, and removed under vacuum. The residue was dried further under vacuum to obtain 2.664 g crude product, which was purified on silica gel (hexane) to obtain 0.813 g (28%) pure ($^1$H NMR) title compound as a colorless liquid; $^1$H NMR (DMSO-d$_6$) δ 1.23 (t, 3H, J=7.5 Hz), 2.73 (q, 2H, J=7.5 Hz), 7.09–7.27 (m, 3H).

2,5-Dichloro-4-ethyl-1-nitrobenzene. To a stiffed solution of 2,5-dichloro-1-ethylbenzene (0.795 g, 4.68 mmol) in concd H$_2$SO$_4$ (4.5 mL) at 0° C., KNO$_3$ (0.473 g, 4.68 mmol) was added in one portion. The resulting pale yellow solution was allowed to warm to room temperature and was stirred overnight at room temperature. It was then poured into ice (80 g) and extracted with ether (3×30 mL). The ether was dried over anhydrous Na$_2$SO$_4$, removed under vacuum, and the resulting oil was dried further under vacuum to obtain 0.943 g (92%) title compound as an oil; $^1$H NMR (CDCl$_3$) δ 1.27 (t, 3H, J=7.5 Hz), 2.80 (q, 2H, J=7.5 Hz), 7.42 (s, 1H), 7.94 (s, 1H).

N-(4'-Chloro-5'-ethyl-2'-nitrophenyl)glycine sodium salt. To a solution of 2,5-dichloro-1-ethylbenzene (0.585 g, 2.66 mmol) in ethanol (10.0 mL) at room temperature was added a solution of sodium glycinate (0.260 g, 2.68 mmol) in water (2.5 mL) and the resulting suspension was refluxed for 2 days. The solution was then cooled to room temperature and the precipitated red solid was filtered, washed with ethanol (4 mL), and dried under vacuum to give 0.086 g (13%) pure ($^1$H NMR) title compound as a red powder; $^1$H NMR (DMSO-d$_6$) δ 1.15 (t, 3H, J=7.2 Hz), 2.63 (q, 2H, J=7.2 Hz), 3.47 (d, 2H, J=3.0 Hz), 6.77 (s, 1H), 7.97 (s, 1H), 8.77 (s, 1H). The unreacted 2,5-dichloro-4-ethyl-1-nitrobenzene was recovered almost quantitatively from the filtrate.

7-Chloro-3,4-dihydro-6ethylquinoxaline-2(1H)-one. A suspension of N-(4'-Chloro-5'-ethyl-2'-nitrophenyl)glycine sodium salt (0.082 g, 0.31 mmol) and tin (II) chloride dihydrate (0.215 g, 0.953 mmol) in ethanol (1.0 mL) was refluxed for 45 min. It was then cooled to room temperature and the precipitated solid was filtered, washed with ethanol (1.0 mL), and dried under vacuum to yield 0.048 g (72%) pure ($^1$H NMR) title compound as a light yellow powder; $^1$H NMR (DMSO-d$_6$) δ 1.05 (t, 3H, J=7.2 Hz), 2.52 (d, 2, J=7.2), 3.67 (s, 2H), 6.04 (s, 1H), 6.54 (s, 1H), 6.67 (s, 1H), 10.25 (s, 1H).

7-Chloro-1,4-dihydro-6-ethyl-5-nitroquinoxaline-2,3-dione. To a stirred suspension of 7-chloro-3,4-dihydro-6-ethylquinoxaline-2(1H)-one (0.020 g, 0.095 mmol) in TFA (0.4 mL), excess fuming HNO$_3$ (0.04 mL) was added and the resulting red solution was stirred overnight at room temperature. The resulting suspension was diluted with water (4 mL) and the precipitated solid was filtered, washed with water (2 mL), and dried under vacuum to yield 0.024 g (94%) pure (HPLC) title compound as a light yellow powder; $^1$H NMR (DMSO-d$_6$) δ 1.09 (t, 3H, J=7.2 Hz), 2.52 (q, 2H, J=7.2 Hz), 7.27 (s, 1H), 11.99 (s, 1H), 12.15 (s, 1H).

Example 47

Preparation of 5-Amino-7-chloro-1,4-dihydro-6-methylquinoxaline-2,3-dione

7-Chloro-1,4-dihydro-6-methyl-5-nitroquinoxaline-2,3-dione. To a stirred suspension of 7-chloro-3,4-Dihydro-6-methyl-quinoxaline-2(1H)-one (0.100 g, 0.51 mmol) in TFA (3.0 mL) prepared as in Example 8, excess fuming HNO$_3$ (0.30 mL) was added and the resulting red solution was stirred overnight at room temperature. The solvent was removed under vacuum and the residue diluted with water (4.0 mL). The precipitated solid was filtered and dried under vacuum to yield 0.067 g (52%) pure (HPLC) title compound as a light yellow powder; mp-darkens at 340° C.; $^1$H NMR (DMSO-d$_6$) δ 2.184 (s, 3H), 7.263 (s, 1H), 11.948 (s, 1H), 12.144 (s, 1H); Anal for C$_9$H$_6$ClN$_3$O$_4$•H$_2$O calcd C, 40.85; H, 2.28; N, 15.87, found C, 40.63; H, 2.05; N, 15.75.

5-Amino-7-chloro-1,4-dihydro-6-methylquinoxaline-2,3-dione. A suspension of 7-chloro-1,4-dihydro-6-methyl-5-nitroquinoxaline-2,3-dione (0.050 g, 0.20 mmol) and tin (II) chloride dihydrate (0.133 g, 0.60 mmol) in ethanol (1.0 mL) was refluxed for 6 h. The suspension was then cooled to room temperature and the solid was collected by vacuum filtration, washed with ethanol (1 mL), and dried further under vacuum to obtain 0.036 g (82%) pure (HPLC) title compound as an off-white solid; mp-darkens at 323° C.; $^1$H NMR (DMSO-d$_6$) δ 2.09 (s, 3H), 5.47 (s, 2H), 6.46 (s, 1H), 11.15 (s, 1H), 11.72 .(s, 1H).

Example 48

Preparation of 7-Chloro-1,4-dihydro-6-ethylthio-5-nitroquinoxaline-2,3-dione

1-Chloro-2,4-difluoro-5-nitrobenzene. To a stirred solution of 1-chloro-2,4-difluorobenzene (0.829 g, 5.58 mmol) in concd H$_2$SO$_4$ (8.0 mL) at 0° C., KNO$_3$ (0.565 g, 5.59 mmol) was added in one portion. The resulting solution was allowed to warm to room temperature and stirred overnight at room temperature. It was then poured into ice (80 g) and extracted with ethyl acetate (75 mL). The ethyl acetate was dried over anhydrous $Na_2SO_4$, removed under vacuum, and the resulting oil was dried further under vacuum to afford 1.007 g (93%) pure ($^1$H NMR) title compound as a light red oil; $^1$H NMR (CDCl$_3$) δ 7.17 (dd, 1H, $J_1$=9.9 Hz, $J_2$=8.4 Hz), 8.24 (t, 1H, J=7.5 Hz).

N-(4'-chloro-5'-fluoro-2'-nitrophenyl)glycine and N-(2'-chloro-5'-fluoro-4'-nitrophenyl)glycine sodium salt. To a stirrd solution of 1-chloro-2,4-difluoro-5-nitrobenzene (1.000, 5.167 mmol) in DMF (10.0 mL), was added dropwise, a solution of sodium glycinate (0.502 g, 5.17 mmol) in water (2.0 mL). The solution was stirred at 70° C. for 16 h. The resulting suspension was then cooled to room temperature and the precipitated solid was filtered, washed with acetone (10 mL), and dried under vacuum to give 0.438 g (38%) red solid as a mixture of title compounds in a ratio of 3:1 ($^1$H NMR); $^1$H NMR (DMSO-d$_6$) δ 3.474 (d, 2H, J=4.5 Hz), 3.523 (d, 2H, J=3.9 Hz), 6.535 (d, 1H, J=14.7 Hz), 6.871 (d, 1H, J=12.3 Hz), 6.976 (s, 1H), 8.068 (d, 1H, J=7.8 Hz), 8.168 (d, 1H, J=7.8 Hz), 8.867 (s, 1H). The separation of the mixture was not feasible at this stage; hence, it was used as such for the next reaction.

7-Chloro-3,4-dihydro-6-fluoro-quinoxaline-2(1H)-one. A suspension of N-(4'-chloro-5'-fluoro-2'-nitrophenyl)glycine sodiumsaltand N-(2'-chloro-5'-fluoro-4'-nitrophenyl)glycine sodium salt (0.175 g, 0.704 mmol) and tin (II) chloride dihydrate (0.475 g, 2.11 mmol) in ethanol (3.5 mL) was refluxed for 30 min. It was then cooled to room temperature and the solvent was removed under vacuum. The residue was diluted with water (10 mL) and the pH was adjusted with saturated NaHCO$_3$ (3.0 mL) to pH~8. The resulting white suspension was extracted with ethyl acetate (30 mL). The ethyl acetate was dried over anhydrous $Na_2SO_4$ and removed under vacuum to yield 0.041 g (29%) pure ($^1$H NMR) title compound as a light yellow powder; mp 217–219° C. (dec); $^1$H NMR (DMSO-d$_6$) δ 3.75 (s, 2H), 6.37 (s, 1H), 6.59 (d, 1H, J=10.5 Hz), 6.74 (d, 1H, J=7.2 Hz), 10.33 (s, 1H).

7-Chloro-1,4-dihydro-6-fluoro-5-nitroquinoxaline-2,3-dione. To a stirred solution of 7-chloro-3,4-dihydro-6-fluoro-quinoxaline-2(1H)-one (0.024 g, 0.12 mmol) in TFA (0.40 mL), excess fuming HNO$_3$ (0.020 mL) was added and the resulting red solution was stirred overnight at room temperature. The solvent was removed under vacuum and the residue was diluted with water (2.0 mL). The precipitated solid was filtered, washed with water (1.0 mL), and dried in a drying pistol (toluene reflux) to yield 0.023 g (74%) pure ($^1$H NMR) tide compound as a light yellow powder; mp 308–310° C.; $^1$H NMR (DMSO-d$_6$) δ 7.37 (d, 1H, J=6.9 Hz), 12.02 (br s, 1H), 12.22 (s, 1H); Anal for $C_8H_3ClFN_3O_4 \cdot H_2O$ calcd C, 34.61; H, 1.09; N, 15.1, found C, 34.66; H, 1.09; N, 15.16%.

7-Chloro-1,4-dihydro-6-ethylthio-5-nitroquinoxaline-2,3-dione. A solution of 7-Chloro-1,4-dihydro-6-fluoro-5-nitroquinoxaline-2,3-dione (0.100 g, 0.385 mmol) and ethanethiol, sodium salt (0.130 g, 1.55 mmol) in DMSO (1.0 mL) was stirred at room temperature for 24 h. The resulting solution was diluted with water (5 mL) and acidified with concd HCl (4–5 drops) to pH~5. The precipitated solid was collected by filtration under vacuum, washed with water (10 mL), and dried under vacuum. to obtain 0.098 g (84%) pure (HPLC) title compound as a yellow powder; mp darkens at 323° C.; $^1$H NMR (DMSO-d$_6$) δ 1.04 (t, 3H, J=7.2 Hz), 2.82 (q, 2H, J=7.5 Hz), 7.34 (s, 1H), 12.20 (s, 1H), 12.25 (s, 1H).

Example 49

Preparation of 7-Chloro-6-methyl-5-nitroquinoxaline-2(1H), 3(4H)-dione

2-Chloro-5-fluoro-4-nitrotoluene. To a stirred solution of 2-chloro-5-fluorotoluene (10.356 g, 71.628 mmol, Lancaster, used as received) in conc. $H_2SO_4$ (70 mL) at 0° C., KNO$_3$ (7.252 g, 71.72 mmol) was added in four equal portions. The resulting pale yellow solution was allowed to warm to room temperature and was stirred overnight at room temperature. It was then poured into ice water (350 g) and extracted with ether (3×100 mL). Ether was dried over anhydrous $Na_2SO_4$, removed under vacuum, and the resulting oil was dried further under vacuum to afford 12.277 g (90%) of the title compound as an oil, which was used as such for the next reaction; $^1$H NMR (CDCl$_3$); δ 2.459 (s, 2H), 7.193 (d, 1H, $J_1$=11.1 Hz), 8.083 (d, 1H, $J_1$=6.6 Hz).

N-4(4'-Chloro-5'-methyl-2'-nitrophenyl)glycine potassium salt. A suspension of 2-chloro-5-fluoro-4-nitrotoluene (11.200 g, 59.078 mmol), glycine (4.500 g, 59.94 mmol), and $K_2CO_3$ (8.300 g, 60.05 mmol) in ethanol (55 mL) and water (30 mL) was refluxed for 7 h. The resulting bright orange solid was cooled to room temperature. The solid was collected by vacuum filtration, washed with water (50 mL), and dried in vacuo. It was then taken up in acetate (150 mL), refluxed for 1 h, and cooled to room temperature. The orange solid was vacuum filtered and dried in vacuo to give 11.37 g (72%) pure ($^1$H NMR) title compound as a red powder; $^1$H NMR (DMSO-d$_6$): δ 2.276 (s, 3H), 3.431 (d, 2H, J=4.2 Hz), 6.848 (s, 1H), 7.963 (s, 1H), 8.773 (s, 1H).

7-Chloro-3,4-dihydro-6-methylquinoxaline-2(1H)-one. To a stirred bright orange solution of N-(4'-chloro-5'-methyl-2'-nitrophenyl)glycine potassium salt (0.097 g, 0.36 mmol) in water (5.0 mL) at 80° C., sodium dithionite (0.500 g, 2.87 mmol) was added in two equal portions. It instantly formed a white suspension, which was stirred at 80° C. for 1 h. It was then cooled at room temperature and the solid was vacuum filtered, washed with water (5.0 mL), and dried in vacuo to yield 0.062 g (86%) of the title compound as a white powder; $^1$H NMR (DMSO-d$_6$): δ 2.10 (s, 3H), 3.66 (s, 2H, J=1.2 Hz), 5.98 (s, 1H), 6.53 (s, 1H), 6.67 (s, 1H), 10.20 (s, 1H).

7-chloro-6-methyl-5-nitroquinoxaline-2(1H),3(4H)-dione. To a stirred suspension of 7-chloro-3,4-dihydro-6-methyl-quinoxaline-2(1H)-one (0.040 g, 020 mmol) in TFA (0.50 mL), excess fuming $H_2SO_3$ (0.040 mL) was added and the resulting yellow suspension was stirred overnight at room temperature. It was poured into ice water (3 mL) and the precipitated solid was vacuum filtered, washed with water (5 mL), and dried in vacuo to yield 0.048 g (92%) pure ($^1$H NMR) of the title compound as a light yellow powder; $^1$H NMR (DMSO-d$_6$): δ 2.184 (s, 3H), 7.263 (s, 1H), 11.948 (s, 1H), 12.144 (s, 1H).

Example 50

Evaluation of the antinociceptive Effect of 5-nitro-6,7-dimethylquinoxalinedione (NDMQX) in the Formalin Test in Swiss Webster Mice Introduction The co-existence of glutamate with substance P in dorsal root ganglion neurons (Battaglia & Rustioni, *J. Comp. Neurol.* 277:302–312 (1988)) and the involvement of the N-methyl-D-aspartate (NMDA) receptor in "wind up" phenomenon in the dorsal horn nociceptive neurons (Davies & Lodge, *Brain Res.* 424:402–406 (1987); Dickenson & Sullivan, *Brain Res.* 506:31–39 (1990); Haley, J. E. et al., *Brain Res.* 518:218–226 (1990)) suggest that excitatory amino acids are involved in nociceptive transmission. There is a great deal of evidence that demonstrates the analgesic effect of the NMDA receptor antagonists in different animal models of pain (Cahusac, P. M. et al., *Neuropharmacol.* 23:719–724 (1984); Murray, C. W. et al., *Pain* 44:179–185

(1991); Elliott, K. J. et al., *Neurosci. Abs.* 17588 (1991); Nasstrom, J. et al., *Eur. J. Pharmacol.* 212:21–29 (1992); Coderre & Melzack, *J. Neurosci.* 12:3665–3670 (1992); Yamamoto & Yaksh, *Anesthesiol.* 77:757–763 (1992); Vaccarino, A. L. et al., *Brain Res.* 615:331–334 (1993); Milan & Seguin, *Eur. J. Pharmacol.* 238:445447 (1993)). However, the lack of access to the brain and/or the PCP-like side effects are disadvantages to the use of some of these compounds.

It is well known that activation of the glycine modulatory site associated with the NMDA receptor is required for the activation of the NMDA receptor (Johnson & Ascher, *Nature* 325:529–531 (1987); Kleckner & Dingledine, *Science* 241:835–837 (1988); Thomson, A. M. et al., *Nature* 338:422424 (1989); Mayer, M. L. et al., *Nature* 338:425–427 (1989)). It has been shown that 7-chloro-kynurenate (7CK), the antagonist for the glycine modulatory site coupled to NMDA receptor blocked the "wind up" phenomenon (Dickenson & Ayder, *Neurosci. Let.* 121:263–266 (1991)). Thus, another approach to produce analgesia would be to antagonize the glycine modulatory site on the NMDA receptor.

Pain in clinical situations usually is prolonged and inflammatory in nature. Thus, the use of animal models of persistent pain appears to be more appropriate to evaluate the potential clinical use of novel analgesic drugs. The present study was designed to evaluate the analgesic effect of NDMQX, a novel and systemically active glycine/NMDA receptor antagonist in the formalin-induced pain in Swiss Webster mice.

Methods

Subjects

Male Swiss Webster mice (25–35 g) obtained from Simonsen Laboratories, Inc. (Gilroy, Calif.) were used in all experiments. Mice were maintained 4–6 per cage with free access to food and water under a 12/12 hr light/dark cycle. Mice were housed for at least 5 days prior to experimentation and used only once. All experiments were conducted during the light cycle in a blind manner in which the observers were not informed about the various treatments.

1. Effect of NDMQX in the Formalin Test

The formalin test performed was a modification of the method of Hunskaar et al. (Hunskaar, S. et al., *J. Neurosci. Meth.* 14:69–76 (1985)). Briefly, after a 60 minute accommodation period in plexiglass jars, mice were weighed and injected intraperitoneally (i.p.) with NDMQX (1–20 mg/kg; N=6–10 mice/dose). Controls were injected with DMSO (1 mL/kg, i.p.). Thirty min later, mice were injected with formalin (20 µl of 5% solution) just under the skin of the right hind paw, transferred to the plexiglass jars, and immediately observed for licking or biting of the injected paw for 1 hr. The amount of time that each mouse spent licking the injected paw was measured at 0–5 min (early phase) and 15–50 min (late phase).

Results

1. Effect of NDMQX in the Formalin Test

Figure 2:
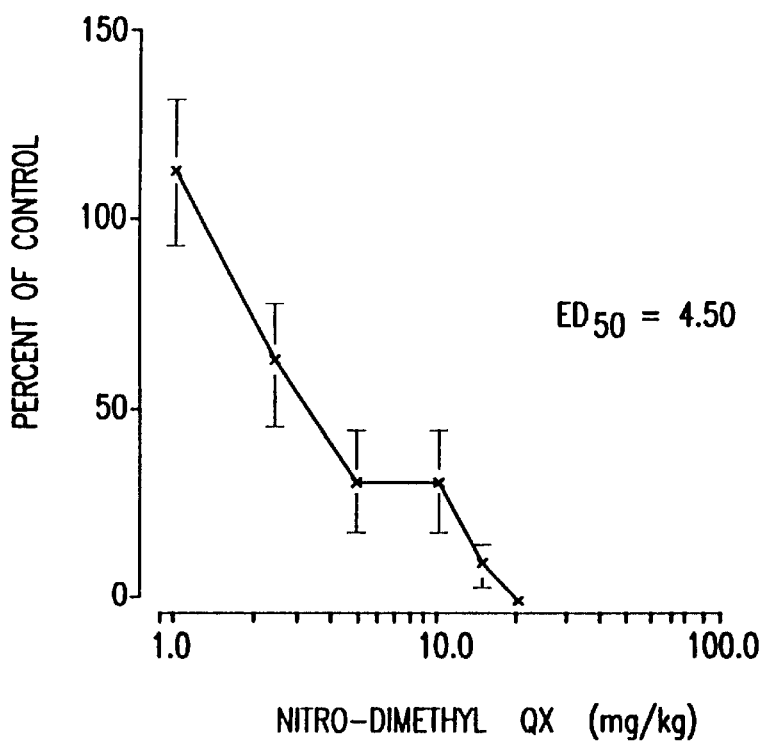
FIG. 2 depicts a graph showing the effect of NDMQX on the late phase of the formalin test for pain.
Figure 3:
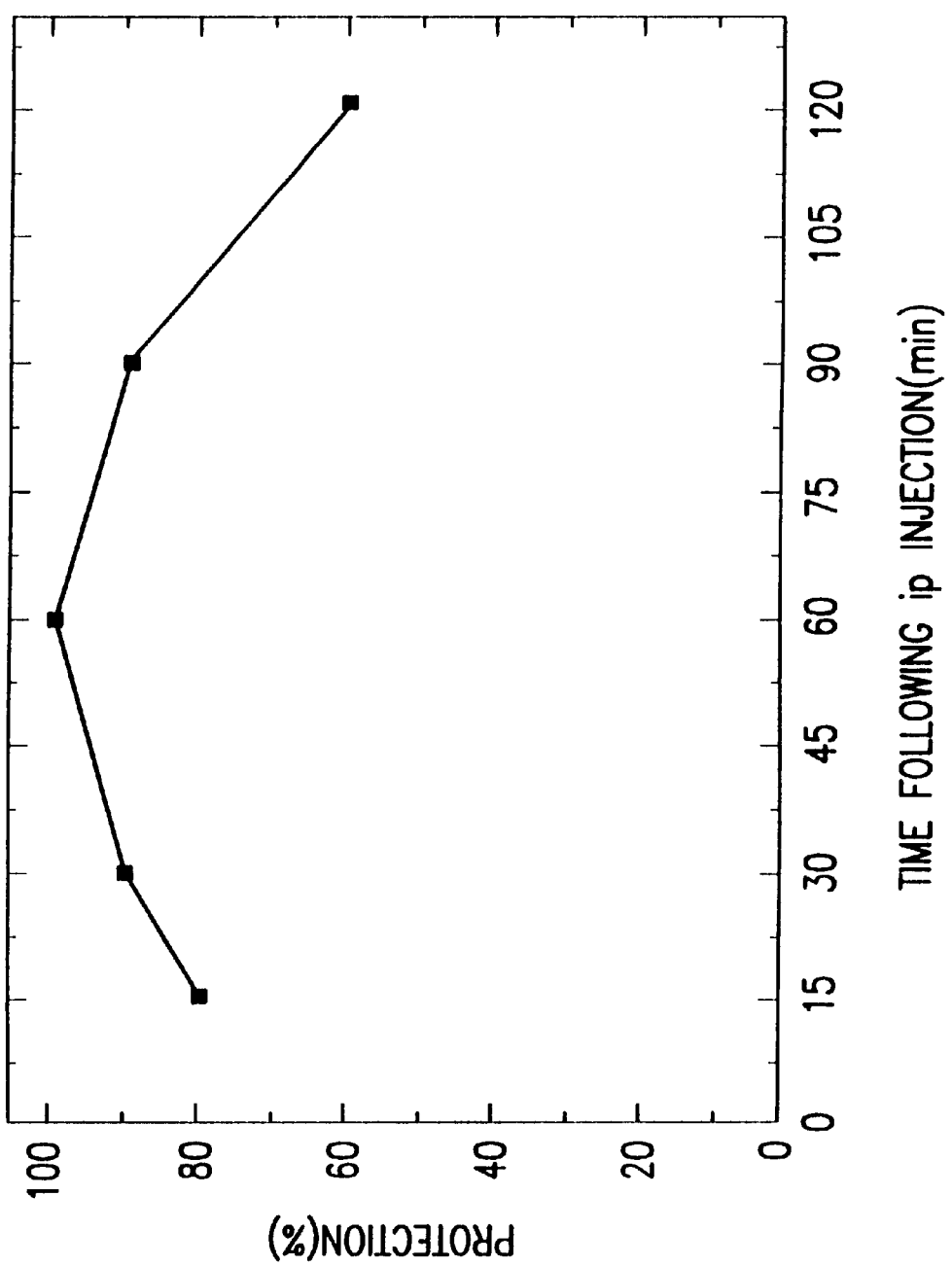
FIG. 3 depicts a graph showing the time course of 7-chloro-6-methyl-5-nitro-1,4-dihydroquinoxaline-2,3-dione (NMCQX) {7.5 mg/kg (Tris 0.05 M)} in the MES test for anti-convulsant effect.
Figure 4:
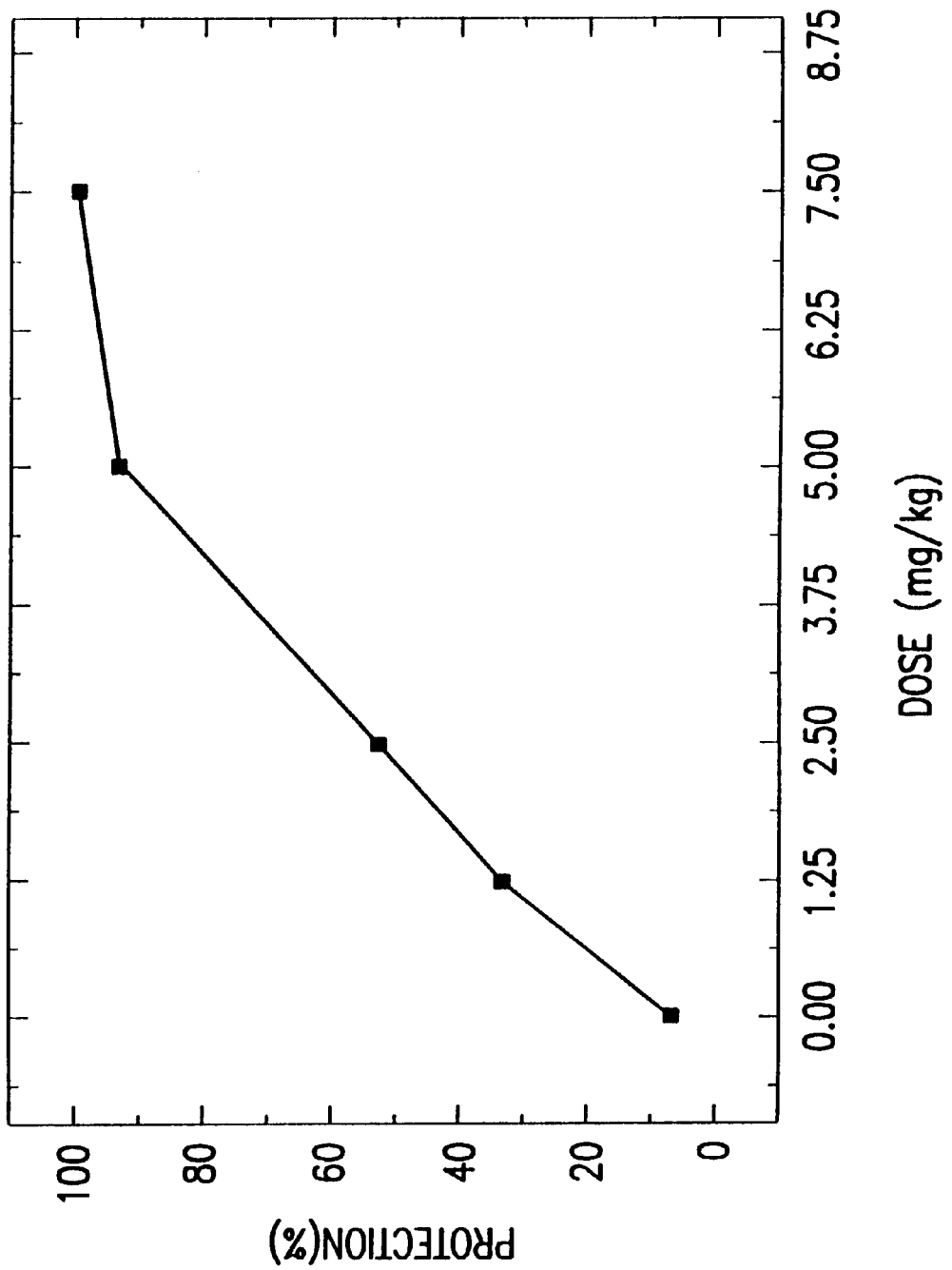
FIG. 4 depicts a graph showing the dose response of NMCQX, 60 minutes following i.p. injection in the MES test for anti-convulsant effect.
Figure 5:
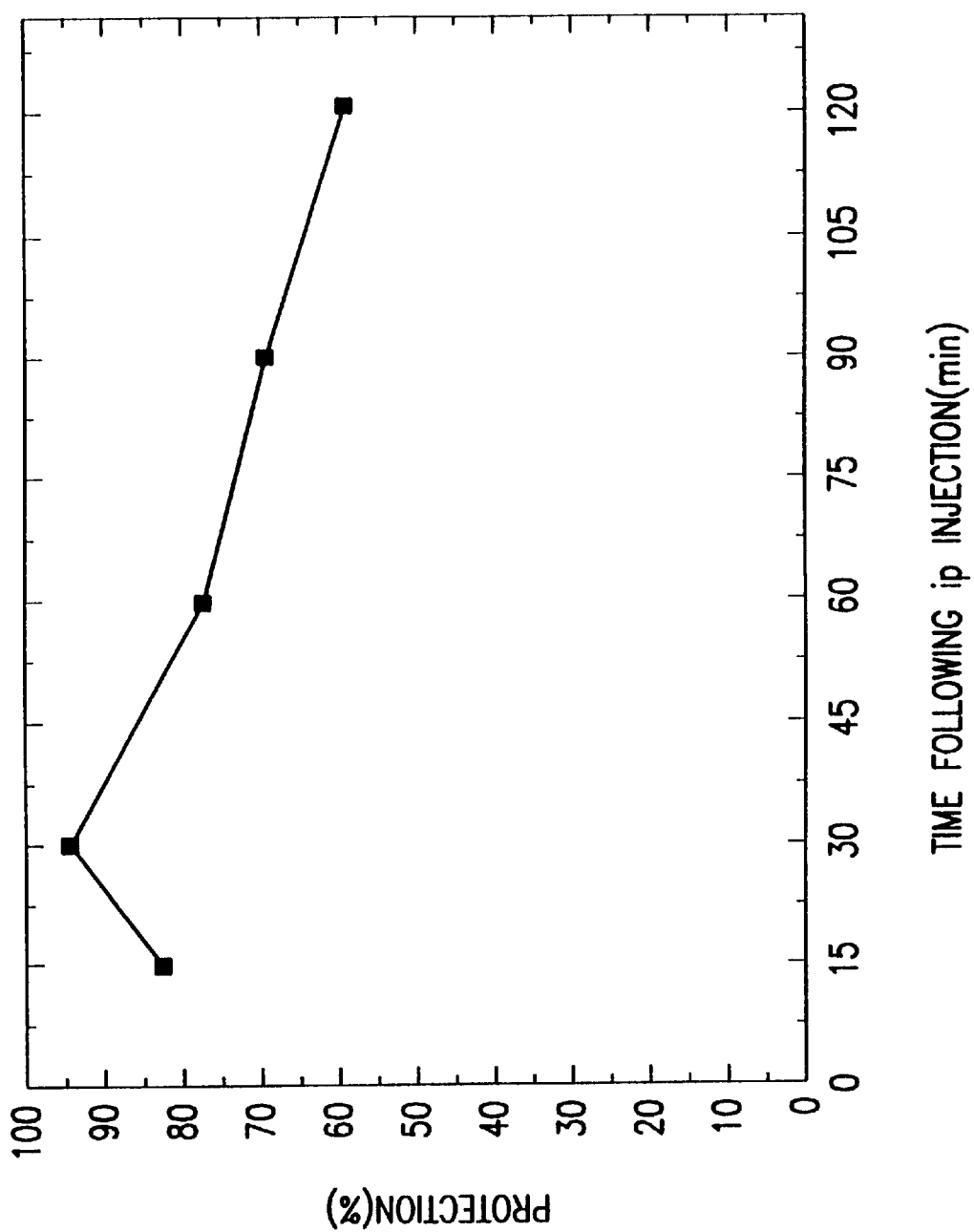
FIG. 5 depicts a graph showing the time course of NDMQX {15 mg/kg (Argenite 0.1 M)} in the MES test for anti-convulsant.
Figure 6:
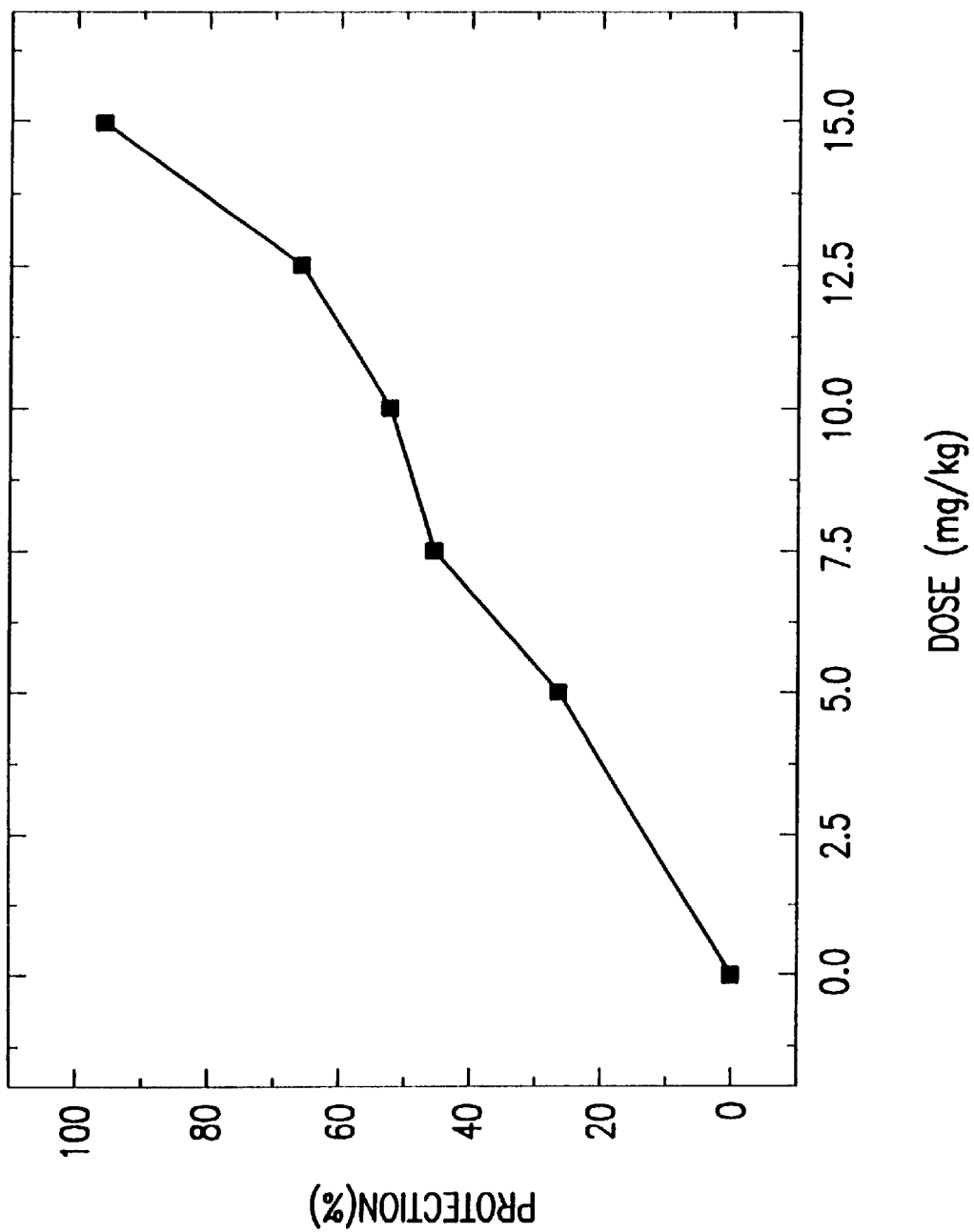
FIG. 6 depicts a graph showing the dose response of NDMQX in the MES test {$O_2p<0.03$;*, $p<0.05$} for anti-convulsant effect.

Systemic administration (i.p.) of NDMQX attenuated the mean time spent licking in a dose-dependent manner in both phases of the formalin test in Swiss Webster mice (FIGS. 1 and 2, and Table V).

Conclusion

NDMQX produced a significant analgesic effect in both phases of the formalin-induced tonic pain in Swiss Webster mice demonstrating that the compound has potential as an analgesic for conditions of tonic pain.

TABLE V

Effect of NDMQX on the time spent licking in the formalin test

| Treatment | Early Phase (0.5 min) (mean ± s.e.m.) (sec per 5 min period) | Late Phase (15–50 min) (mean ± s.e.m.) (sec per 5 min period) |
| --- | --- | --- |
| DMSO | 86.70 ± 8.65 | 33.00 ± 3.78 |
| NDMQX (1.0 mg/kg) | 72.57 ± 14.2 | 37.59 ± 5.37 |
| NDMQX (2.5 mg/kg) | 78.50 ± 10.0 | 26.38 ± 5.43 |
| NDMQX (5 mg/kg) | 32.83 ± 8.28 | 10.24 ± 2.66 |
| NDMQX (10 mg/kg) | 29.17 ± 14.9 | 10.19 ± 2.44 |
| NDMQX (15 mg/kg) | 6.83 ± 1.85 | 3.19 ± 1.37 |
| NDMQX (20 mg/kg) | 4.33 ± 2.85 | 0.05 ± 0.05 |

Example 51

The Anti-convulsant Effect and Antinociceptive Effect of 5-nitro-6-methyl-7chloro-2,3-quinoxalinedione (NMCQX) and 5-nitro-6,7-dimethyl-2,3-quinoxalinedione (NDMQX) in the MES and Formalin Test The anti-convulsant and antinociceptive effect of NMCQX and NDMQX in the MES and in the formalin test in Swiss Webster mice were evaluated.

In the MES test, mice were injected i.p. with NMCQX (1.25–7.50 mg/kg) or NDMQX (5.00–15.00 mg/kg). Control mice were injected with Tris (0.05 M) or Arginine (0.1 M), respectively. Seizures were then induced by applying a rectangular pulse, 50 mA, 60 pulses/sec, 0.8 msec pulse width, and 0.2 sec train length, at the time of the drugs' peak effect. Both compounds dose-dependently protected mice from generalized clonic-tonic seizures induced by electroshock. Experimental results are shown in FIGS. 3–6.

In the formalin test, following a 1 hr accommodation period, mice were injected i.p. with NMCQX (1.00–10.00 mg/kg, N=7–13 mice/dose) or NDMQX (0.5–20.00 mg/kg, N=8–9 mice/dose). Control mice were injected with Tris (0.5 M) or Bis-Tris (0.2 M), respectively. Mice were then injected with formalin. A s.c. injection of formalin produced a biphasic nociceptive response, i.e., an early phase (0–5 min) followed by a tonic late phase (15–50 min). Both compounds produced a dose-dependent antinociceptive effect in both phases of the formalin test. The amount of time that each mouse spent licking and/or biting the injected paw was recorded for 1 hr.

The data suggest a modulatory role for the NMDA receptor in MES-induced seizures and in formalin-induced nociception.

Example 52

Blockade of Morphine Tolerance by 5-nitro-6,7-dimethyl-2,3-quinoxalinedione (NDMQX)

Introduction

Opioid analgesics are used for the management of pain. However, the development of tolerance to opioid analgesics impedes the therapeutic use of these drugs. Seeking alternative drugs to produce analgesia without development of tolerance or as an adjunct therapy to block tolerance without interference with analgesia is an active area of research. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). The results of recent studies have suggested a modulatory role for N-methyl-D-aspartate (NMDA) receptor in morphine tolerance (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993).

Glycine is required for activation of the NMDA receptor (Johnson et al., Nature 325:529–533 (1987); Kleckner et al., Science 241:835–837 (1988); Mayer et al., Nature 338:425427 (1989); Thomson et al., Nature 338:422–424 (1989)). Thus, another approach to block the NMDA receptor, and consequently block tolerance would be to antagonize the glycine modulatory site of the NMDA receptor. This example shows the use of 5-nitro-6,7-di-methyl-1,4-dihydro-2,3-quinoxalinedione (NDMQX) to test the hypothesis that inhibition at the NMDA receptor/glycine site might be a viable means of blocking morphine tolerance.

Materials and Methods

Subjects

Male Swiss Webster mice, weighing 25–35 g, obtained from Simonsen Laboratories, Inc. (Gilroy, Calif.) were used in all experiments. Mice were maintained 4–6 to a cage with free access to food and water under a 12-hr light/12-hr dark cycle. Mice were housed for at least 5 days prior to experimentation and used only once. All experiments were conducted during the light cycle in a blind manner in which the observers were unaware of different treatments.

Formalin Test

A modification of a previously described method was used (Hunskaar et al., J. Neurosci. Meth. 14:69–76 (1985)). Briefly, mice were placed in Plexiglas jars for at least 1 hr for accommodation to the experimental condition. Formalin (20 μl of 5% formaldehyde solution in saline) was injected into the dorsal surface of the right hind paw using a microsyringe (Hamilton Co., Reno, Nev.) with a 27-gauge needle. Mice were then transferred to the Plexiglas jars and immediately observed for licking or biting of the injected paw for 1 hr. The amount of time that each mouse spent licking or biting the injected paw was recorded for every 5-min period for a 1 hr observation period.

1. Effect of NDMQX on Morphine Tolerance in the Formalin Test

Mice were injected daily for a period of 8 days with either vehicle (Bis-Tris; 0.2 M) or NDMQX (1, 20 and 40 mg/kg, i.p.; N=9–12 mice/group). Mice were immediately, within a minute, injected with either saline or morphine (20 mg/kg, s.c.). On day 9, mice were weighed and after a 1-hr accommodation period-injected with morphine (4 mg/kg, s.c.). Thirty min later, all mice were tested in the formalin test (see above).

2. Effect of NDMQX on Morphine Antinociception in the Formalin Test

Mice were injected daily for a period of 8 days with either vehicle (Bis-Tris; 0.2 M) or NDMQX (40 mg/kg, i.p.; N=7 mice/group). One group of mice (N=11) was left untreated.

On day 9, mice were weighed and after a 1-hr accommodation period injected with morphine (4 mg/kg, s.c.). The untreated group was divided into two subgroups; half of which received saline while the other half was injected with morphine (4 mg/kg). Thirty min later, all mice were tested in the formalin test (see above).

Results

1. Effect of NDMQX on Morphine Tolerance in the Formalin Test

Figure 7:
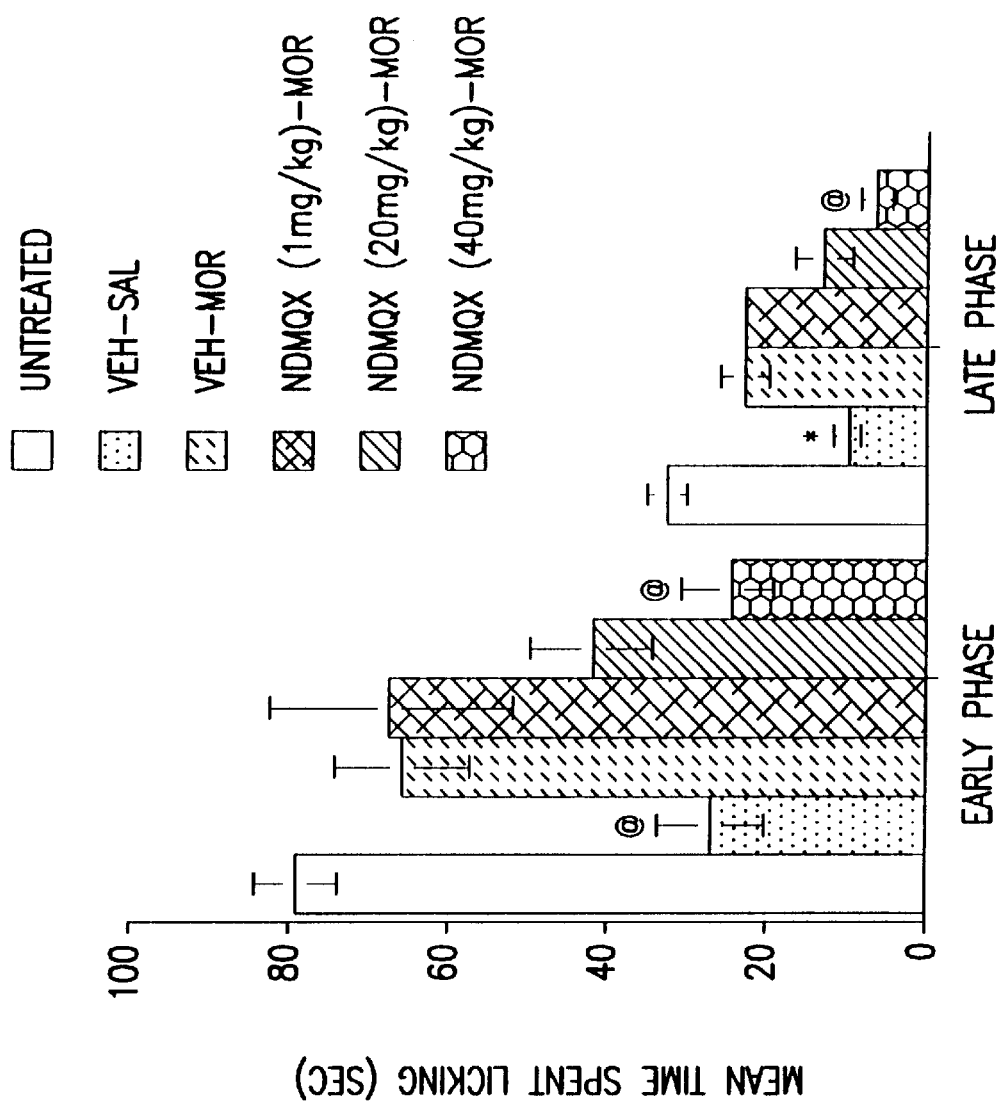
FIG. 7 depicts a graph showing the effect of chronic (8 days) NDMQX on morpine tolerance in the formalin test.

Morphine administration for 8 days produced tolerance in early and late 15 phases of the formalin test (FIG. 7). A one-way ANOVA followed by Newman-Keul test revealed a statistically significant tolerance in mice treated chronically with morphine ($F_{4,47}=4.20$ and $F_{4,47}=3.93$ for the early and late phases, respectively; $p<0.05$ or better). Tolerance did not develop in mice treated with NDMQX followed by morphine. The inhibitory effect of NDMQX on morphine tolerance was dose-dependent. NDMQX had no effect on morphine tolerance at 2 mg/kg; at higher doses it either attenuated (at 20 mg/kg) or completely abolished (at 40 mg/kg) morphine tolerance (FIG. 7).

2. Effect of NDMQX on Morphine Antinociception in the Formalin Test

Figure 8:
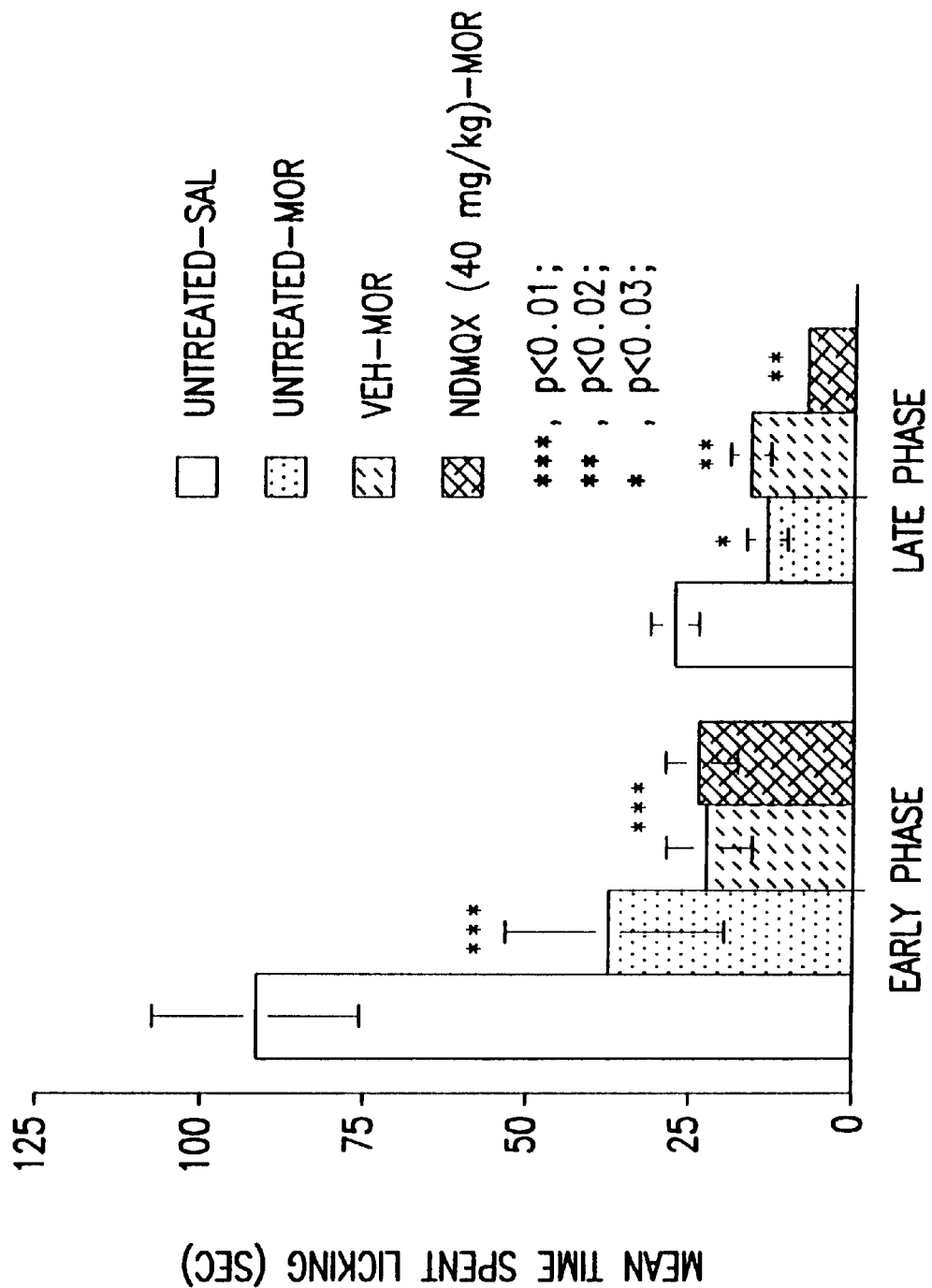
FIG. 8 depicts a graph showing the effect of chronic (8 days) NDMQX on morphine-induced antinociception in the formalin test.

It was found that chronic administration of NDMQX for 8 days did not alter the antinociceptive effect of morphine in the formalin test (FIG. 8). There was no significant difference in morphine-induced antinociception between NDMQX-pretreated and control (vehicle-pretreated) groups ($p>0.05$). In addition, the level of antinociception produced by morphine in these two groups was not significantly different from that of untreated (naive) mice.

Conclusion

NDMQX, a novel NMDA receptor/glycine site antagonist, blocked morphine tolerance in both phases of the formalin test. The blockade of tolerance by NDMQX was not due to potentiation of morphine-induced antinociception in the formalin test. These data suggest that the NMDA receptor is involved in modulation of morphine tolerance in an animal model of tonic pain. The blockade of morphine tolerance by NMDQX in the formalin test suggests that antagonism at the glycine modulatory site associated with the NMDA receptor is a viable means to inhibit NMDA receptor and block morphine tolerance. Therefore, the antagonism at the glycine modulatory site associated with the NMDA receptor appears to be a potential site for the development of new drugs that could be used with morphine as adjunct therapy in the management of pain and prevention of tolerance.

Example 53

The Neuroprotective Effect of NDMQX in a Rat Model of Permanent Focal Cerebral Ischemia Using Continuous Intravenous Drug Infusion The N-methyl-D-aspartate (NMDA) subtype of excitatory amino acid receptors appears to play a crucial role in neuronal degeneration induced by focal cerebral ischemia. A number of competitive and non-competitive NMDA receptor antagonists have been shown to provide significant protection against neuronal degeneration in different animal models of focal ischemia (see Bullock et al., J. Neurotrauma 9 (Supp. 2):S443S462 (1992)). In this example, the neuroprotective effect of the NMDA receptor glycine site antagonist NDMQX in the rat model of the focal ischemia is described.

Methods

1. Induction of Focal Ischemia

Male Sprague-Dawley rats (290–320 g) were incubated and maintained under anesthesia with ±2% of halothane. Body temperature was maintained at 37.5° C. during surgery by means of a warming pad and a rectal probe connected to the control unit. The common carotid arteries (CCA) were isolated, and a loose silk ligature was placed around each CCA. A vertical skin incision was made between the left orbit and the auditory canal, posterior part of zygoma removed and small opening (2.0/2.5 mm) drilled dorso-rostrally to the foramen ovale under constant saline irrigation. The dura was opened with a microsurgical hook and the brain gently retracted with a fine spatula to expose the bifurcation of the internal carotid artery and the middle cerebral artery. The ipsilateral CCA was ligated and the MCA coagulated from its origin to the olfactory tract. Two hours after MCA occlusion, the clip from the contralateral CCA was removed.

2. Drug Administration

NDMQX was dissolved in 0.1 M L-arginine and 5% glucose and infused as a slow 10 mg/kg i.v. bolus (immediately after MCA occlusion) followed by 7 mg/kg/h infusion for 22 hours.

3. Histology

Brains were sliced into 2 mm blocks and stained with tetrazolium red (2,3,5-triphenyl tetrazolium chloride). The areas of brain damage were assessed using an image analyzer (Image-1, Universal Imaging Corporation, Pa.) to determine the volume of cortical and subcortical infarction by integration of areas and the distance between each level.

Results

Figure 9:
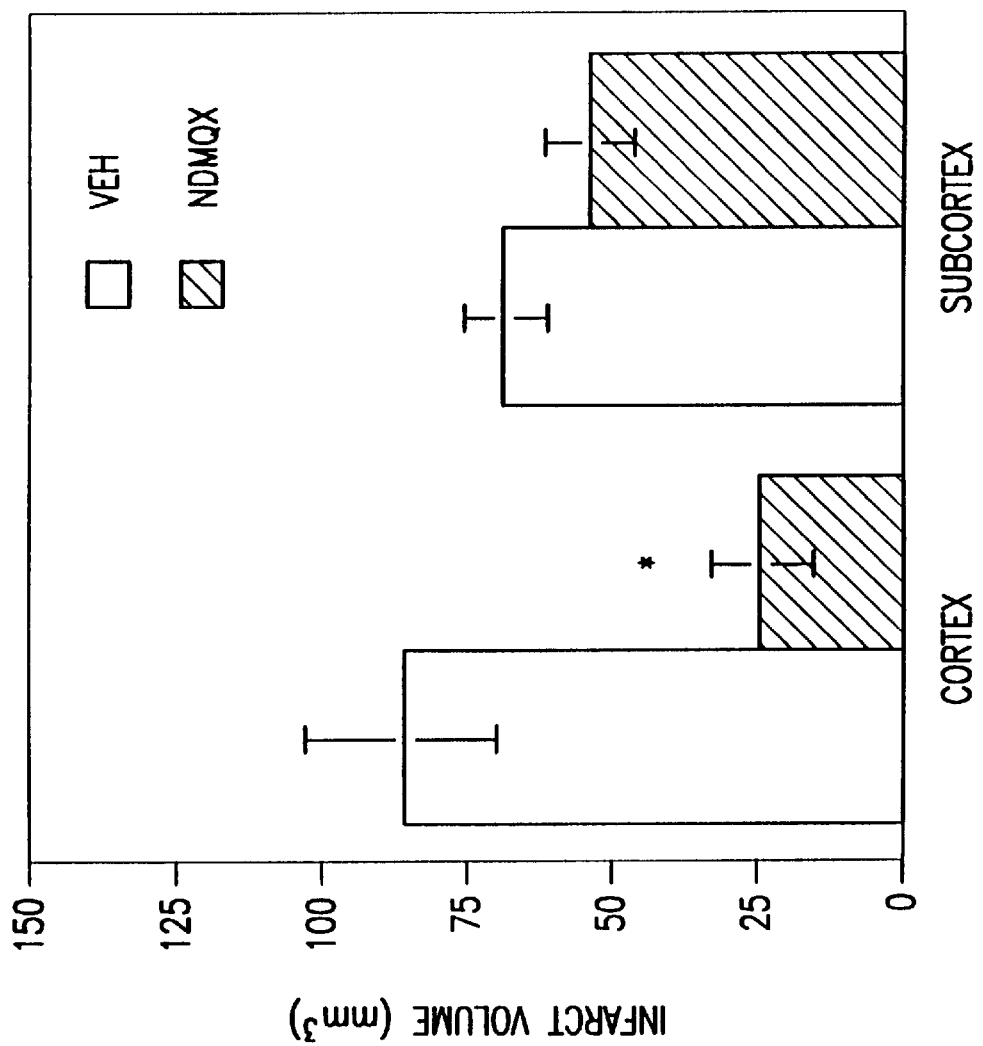
FIG. 9 depicts a graph showing the effect of NDMQX on cortical and subcortical infarct volume.

NDMQX produced significant reduction (71%, $F_{1,19}$=11.57, p<0.05, ANOVA) in cortical infarct volume. See FIG. 9.

Conclusion

NDMQX provided significant neuroprotection in a rat model of focal ischemia.

Example 54

Neuroprotective Effect of NMCQX in a Rat Model of Permanent Focal Cerebral Ischemia Using Continuous Intravenous Drug Infusion Example 52 was repeated, except that NMCQX was substituted for the NDMQX employed therein. For the drug administration, the NMCQX was dissolved in 0.05 Tris and 5% glucose. It was infused as a slow 2 mg/kg i.v. bolus (immediately after MCA occlusion) followed by 1.4 mg/kg/h infusion for 22 hours.

Figure 10:
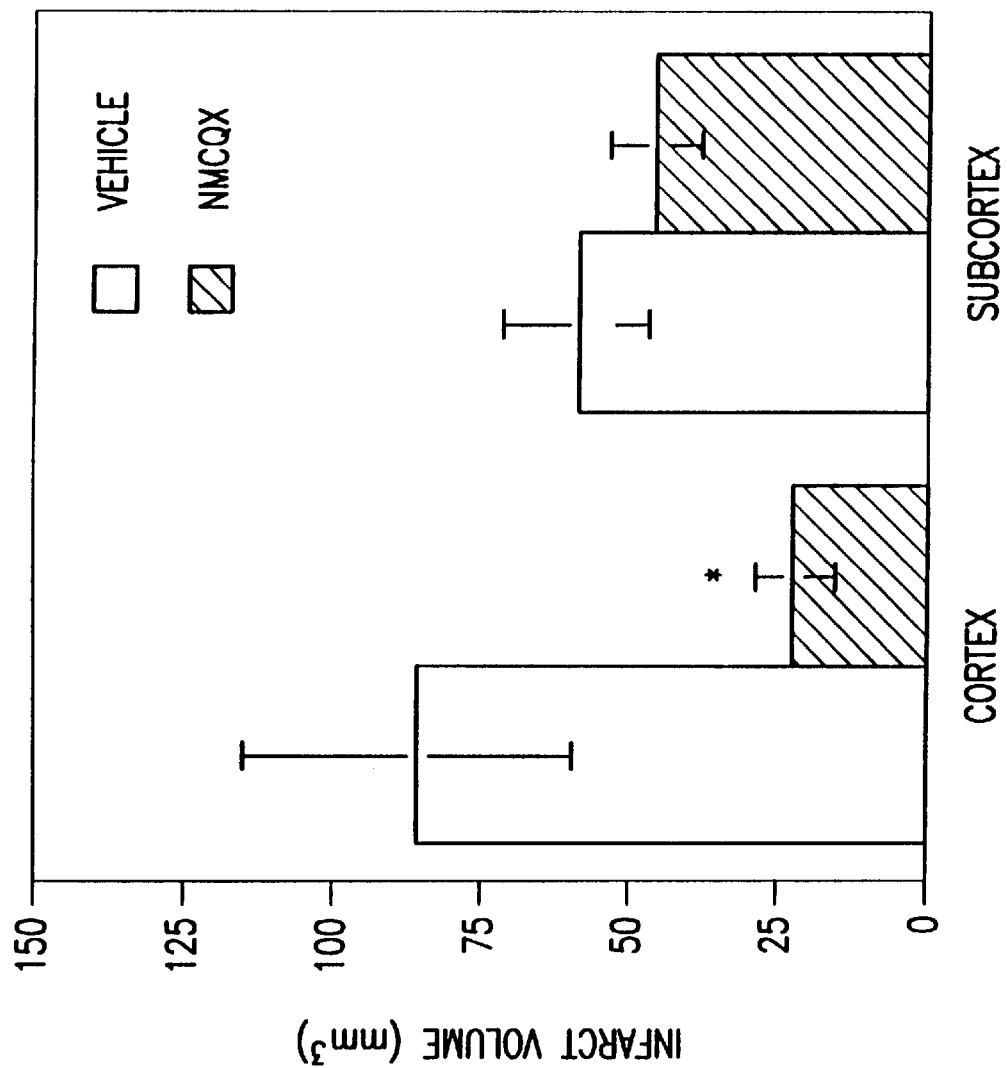
FIG. 10 depicts a graph showing the effect of NMCQX on cortical and subcortical infarct volume.

NMCQX produced a significant reduction (75%, $F_{1,18}$=5.24, p<0.05, ANOVA) in cortical infarct volume. See FIG. 10.

Thus, NMCQX also provided significant neuroprotection in a rat model of focal ischemia.

Having now fully described this invention, it will be understood by those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of treating chronic pain, treating or preventing anxiety, treating or preventing convulsions, inducing anesthesia, treating or preventing NMDA receptor-ion channel psychosis, inducing a hypnotic effect, or treating or preventing opiate tolerance, comprising:

administering to an animal in need of such treatment an effective amount of a compound having the Formula:

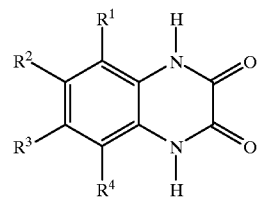

or a tautomer or a pharmaceutically acceptable salt thereof; wherein $R^1$ is alkyl, azido, alkoxy, hydroxy, haloalkyl, halo, nitro, cyano or alkanoylamino;

$R^2$ is alkyl, azido, alkoxy, aralkoxy, cyano, haloalkyl, halo, hydroxy or nitro;

$R^3$ is alkyl, azido, alkoxy, cyano, halo, haloalkyl or hydroxy;

$R^4$ is hydrogen or fluoro;

provided that (a) at least one of $R^1$, $R^2$ or $R^3$ is hydroxy or azido, or (b) at least one of $R^2$ or $R^3$ is alkyl or alkoxy, or (c) $R^1$ is cyano.

2. The method of claim 1, wherein said compound is 6,7-dimethyl-5-nitro-1,4-dihydroquinoxaline-2,3-dione, 7-fluoro-6-methyl-5-nitro-1,4-dihydroquinoxaline-2,3-dione, 7-chloro-6-methyl-5-nitro-1,4-dihydroquinoxaline-2,3-dione, 7-bromo-6-methyl-5-nitro-1,4-dihydroquinoxaline-2,3-dione, 6-chloro-7-methyl-5-nitro-1,4-dihydroquinoxaline-2,3-dione, 6,7-diethel-5-nitro-1,4-dihydroquinoxaline-2,3-dione, 5-cyano-6,7-dichloro-1,4-dihydroquinoxaline-2,3-dione, or 5-azido-6,7-dichloro-1,4-dihydroquinoxaline-2,3-dione.

3. The method of claim 1, wherein said compound is 7-chloro-6-methyl-5-nitro-1,4-dihydroquinoxaline-2,3-dione.

4. The method of claim 1, wherein said compound is 5-cyano-6,7-dichloro-1,4-dihydroquinoxaline-2,3-dione.

5. A method of treating chronic pain, treating or preventing anxiety, treating or preventing convulsions, inducing anesthesia, treating or preventing NMDA receptor-ion channel psychosis, inducing a hypnotic effect, or treating or preventing opiate tolerance, comprising:

administering to an animal in need of such treatment an effective amount of a compound having the Formula:

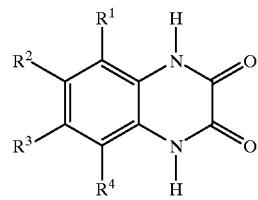

or a tautomer or a pharmaceutically acceptable salt thereof; wherein $R^1$ is nitro, cyano, $CF_3$, carboxy, or alkanoyl;

$R^2$ is alkoxy, aralkoxy, thioalkyl, hydroxy, mercaptoalkyl, or azido;

$R^3$ is halo, haloalkyl, nitro, alkyl, alkoxy, azido, or cyano; and $R^4$ is hydrogen.

6. The method of claim 5, wherein said compound is selected from the group consisting of 6-azido-7-fluoro-5-nitro-1,4-dihydroquinoxaline-2,3-dione, 7-fluoro-6- methoxy-5nitro-1,4-dihydroquinoxaline-2,3-dione, 7-chloro-6-methoxy-5-nitro-1,4-dihydroquinoxaline-2,3-dione, 7-chloro-6-ethylthio-5-nitro-1,4-dihydroquinoxaline-2,3-dione and 7-fluoro-6-ethoxy-5-nitro-1,4-dihydroquinoxaline-2,3-dione.

7. The method of claim 1, wherein said compound is administered as an ammonium salt comprising said compound and an amino compound.

8. The method of claim 7, wherein said amino compound is one of choline, TRIS, bis-tris-propane, N-methylglucamine or arginine.

9. A pharmaceutical composition, comprising:
(a) a pharmaceutically acceptable carrier; and
(b) a compound having the Formula:

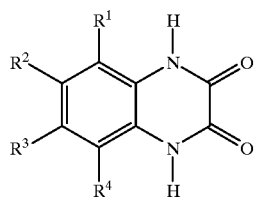

or a tautomer or a pharmaceutically acceptable salt thereof; wherein $R^1$ is alkyl, azido, alkoxy, hydroxy, haloalkyl, halo, nitro, cyano or alkanoylamino;

$R^2$ is alkyl, azido, alkoxy, aralkoxy, cyano, haloalkyl, halo, hydroxy or nitro;

$R^3$ is alkyl, azido, alkoxy, cyano, halo, haloalkyl or hydroxy;

$R^4$ is hydrogen or fluoro;

provided that (a) at least one of $R^1$, $R^2$ or $R^3$ is hydroxy or azido, or (b) at least one of $R^2$ or $R^3$ is alkyl or alkoxy, or (c) $R^1$ is cyano.

10. A pharmaceutical composition, comprising:
(a) a pharmaceutically acceptable carrier; and
(b) a compound having the Formula:

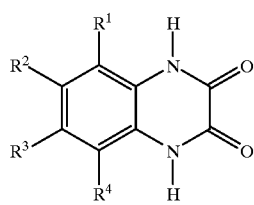

or a tautomer or a pharmaceutically acceptable salt thereof; wherein $R^1$ is nitro, cyano, $CF_3$, carboxy, or alkanoyl;

$R^2$ is alkoxy, aralkoxy, thioalkyl, hydroxy, mercaptoalkyl, or azido;

$R^3$ is halo, haloalkyl, nitro, alkyl, alkoxy, azido, or cyano; and $R^4$ is hydrogen.

11. A method of antagonizing excitatory amino acids at the NMDA receptor complex, comprising administering to an animal in need thereof an effective amount of a compound of the Formula

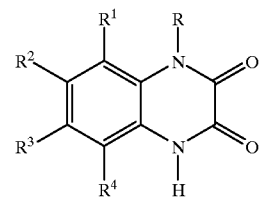

or a tautomer or a pharmaceutically acceptable salt thereof; wherein

R is hydrogen;

$R^1$ is alkyl, azido, alkoxy, hydroxy, haloalkyl, halo, nitro, cyano or alkanoylamino;

$R^2$ is alkyl, azido, alkoxy, aralkoxy, cyano, haloalkyl, halo, hydroxy or nitro;

$R^3$ is alkyl, azido, alkoxy, cyano, halo, haloalkyl or hydroxy;

$R^4$ is hydrogen or fluoro;

provided that (a) at least one of $R^1$, $R^2$ or $R^3$ is hydroxy or azido, or (b) at least one of $R^2$ or $R^3$ is alkyl or alkoxy, or (c) $R^1$ is cyano.

12. The method of claim 11, wherein said compound is 6,7-dimethyl-5-nitro-1,4-dihydroquinoxaline-2,3-dione, 7-fluoro-6-methyl-5-nitro-1,4-dihydroquinoxaline-2,3-dione, 7-chloro-6-methyl-5-nitro-1,4-dihydroquinoxaline-2,3-dione, 7-bromo-6-methyl-5-nitro-1,4-dihydroquinoxaline-2,3-dione, 6-chloro-7-methyl-5-nitro-1,4-dihydroquinoxaline-2,3-dione, 6,7-diethel-5-nitro-1,4-dihydroquinoxaline-2,3-dione, or 5-azido-6,7-dichloro-1,4-dihydroquinoxaline-2,3-dione.

13. A method of antagonizing excitatory amino acids at the NMDA receptor complex, comprising administering to an animal in need thereof an effective amount of a compound having the Formula

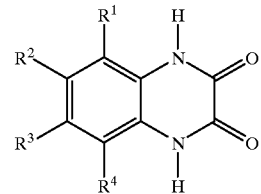

or a tautomer or a pharmaceutically acceptable salt thereof; wherein $R^1$ is nitro, cyano, $CF_3$, carboxy, or alkanoyl;

$R^2$ is alkoxy, aralkoxy, thioalkyl, hydroxy, mercaptoalkyl, or azido;

$R^3$ is halo, haloalkyl, nitro, alkyl, alkoxy, azido, or cyano; and $R^4$ is hydrogen.

14. The method of claim 13, wherein said compound is selected from the group consisting of 6-azido-7-fluoro-5-nitro-1,4-dihydroquinoxaline-2,3-dione, 7-fluoro-6-methoxy-5-nitro-1,4-dihydroquinoxaline-2,3-dione, 7-chloro-6-methoxy-5-nitro-1,4-dihydroquinoxaline-2,3-dione, and 7-fluoro-6-ethoxy-5-nitro-1,4-dihydroquinoxaline-2,3-dione.

* * * * *